(12) United States Patent
Collins

(10) Patent No.: US 11,807,842 B2
(45) Date of Patent: Nov. 7, 2023

(54) FLUIDIC ARRAY SYSTEMS AND TESTING FOR CELLS, ORGANOIDS, AND ORGAN CULTURES

(71) Applicant: John Collins, Irvine, CA (US)

(72) Inventor: John Collins, Irvine, CA (US)

(73) Assignee: Biopico Systems Inc, Irvine, CA (US)

( * ) Notice: Subject to any disclaimer, the term of this patent is extended or adjusted under 35 U.S.C. 154(b) by 411 days.

(21) Appl. No.: 16/948,734

(22) Filed: Sep. 30, 2020

(65) Prior Publication Data

US 2021/0095235 A1    Apr. 1, 2021

Related U.S. Application Data

(60) Provisional application No. 62/908,201, filed on Sep. 30, 2019.

(51) Int. Cl.
| | |
|---|---|
| *C12M 3/00* | (2006.01) |
| *B01L 3/00* | (2006.01) |
| *C12M 3/06* | (2006.01) |
| *C12M 1/32* | (2006.01) |

(52) U.S. Cl.
CPC ......... *C12M 23/16* (2013.01); *B01L 3/50273* (2013.01); *B01L 3/502715* (2013.01); *B01L 3/502746* (2013.01); *B01L 3/502761* (2013.01); *C12M 23/12* (2013.01); *B01L 2300/0829* (2013.01); *B01L 2300/0848* (2013.01); *B01L 2300/0883* (2013.01); *B01L 2400/0406* (2013.01); *B01L 2400/086* (2013.01)

(58) Field of Classification Search
CPC .............. C12M 23/16; B01L 3/502715; B01L 2400/0457
See application file for complete search history.

(56) References Cited

U.S. PATENT DOCUMENTS

| | | | |
|---|---|---|---|
| 10,525,472 B1* | 1/2020 | Pandey | B01L 3/502792 |
| 2009/0205201 A1* | 8/2009 | Xu | C12M 41/36 |
| | | | 219/121.69 |
| 2010/0144022 A1* | 6/2010 | Surapaneni | C12M 23/48 |
| | | | 435/289.1 |
| 2012/0003732 A1* | 1/2012 | Hung | C12M 23/34 |
| | | | 435/289.1 |
| 2014/0065661 A1* | 3/2014 | Baumgartner | B01L 3/50255 |
| | | | 422/552 |
| 2018/0345280 A1* | 12/2018 | Vulto | B01L 9/527 |
| 2020/0024563 A1* | 1/2020 | Horst | C12M 29/18 |
| 2020/0070165 A1* | 3/2020 | Shuler | C12M 23/16 |
| 2020/0139364 A1* | 5/2020 | Kim | B01L 3/50273 |

(Continued)

OTHER PUBLICATIONS

Zhang et al. Well Plate-Based Perfusion Culture Device for Tissue and Tumor Microenvironment Replication. Lap Chip, 2015, 15, 2854-63 (Year: 2015).*

*Primary Examiner* — Nathan A Bowers

(57) ABSTRACT

A system and method for array system for cells, organoids and organs culture and testing. The system includes a disposable chips and systems with actuators, sensors, software/firmware and smart device App. The disposable includes standard well plates, custom well plates, T-flasks, microfluidic chips. The system includes vascular fluidics using gravity-driven flow and pneumatic flow, media, reagents, protein and collagen dispensers in wells or surfaces, manufacturing techniques for multi-layer chips and plates and culture system with gas and media control.

16 Claims, 55 Drawing Sheets

(56) References Cited

U.S. PATENT DOCUMENTS

| | | | |
|---|---|---|---|
| 2020/0181551 A1* | 6/2020 | Lee | C12M 23/20 |
| 2020/0408751 A1* | 12/2020 | Lionberger | G01N 33/54366 |
| 2021/0072267 A1* | 3/2021 | Saiki | B01F 31/10 |

* cited by examiner

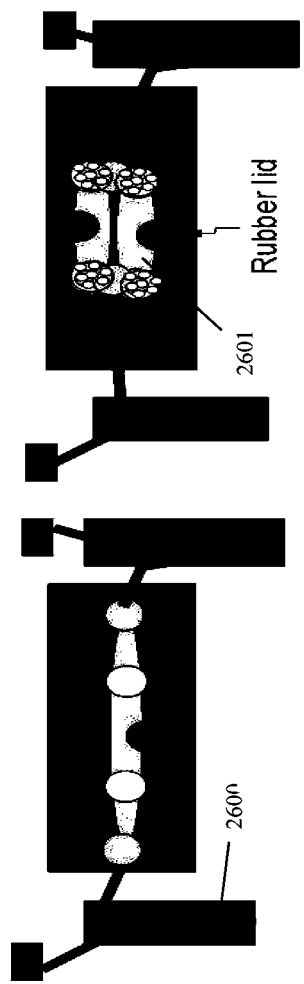
FIG. 26A
FIG. 26B
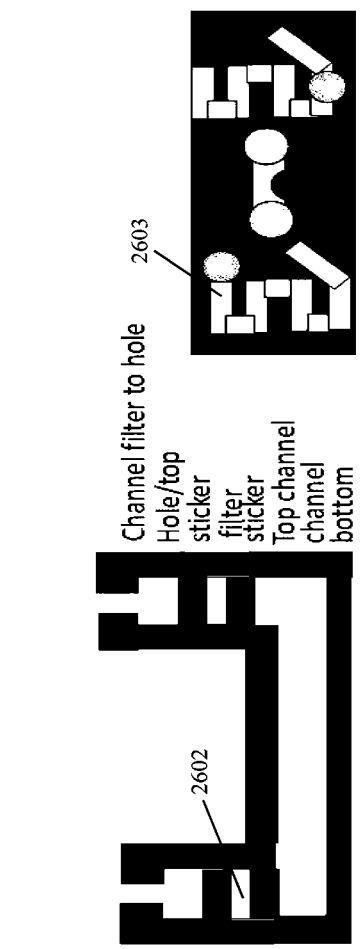
FIG. 26C
FIG. 26D

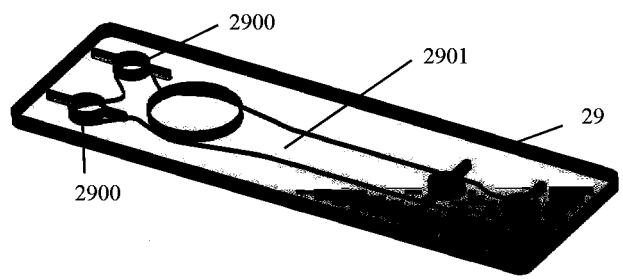
FIG. 29A
FIG. 29B
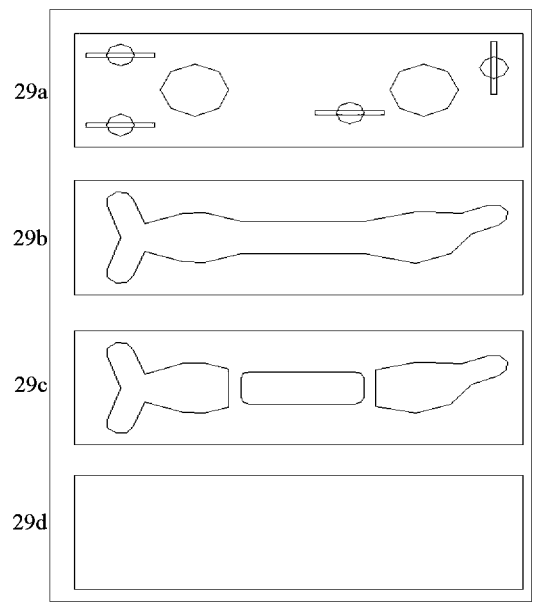
FIG. 29C

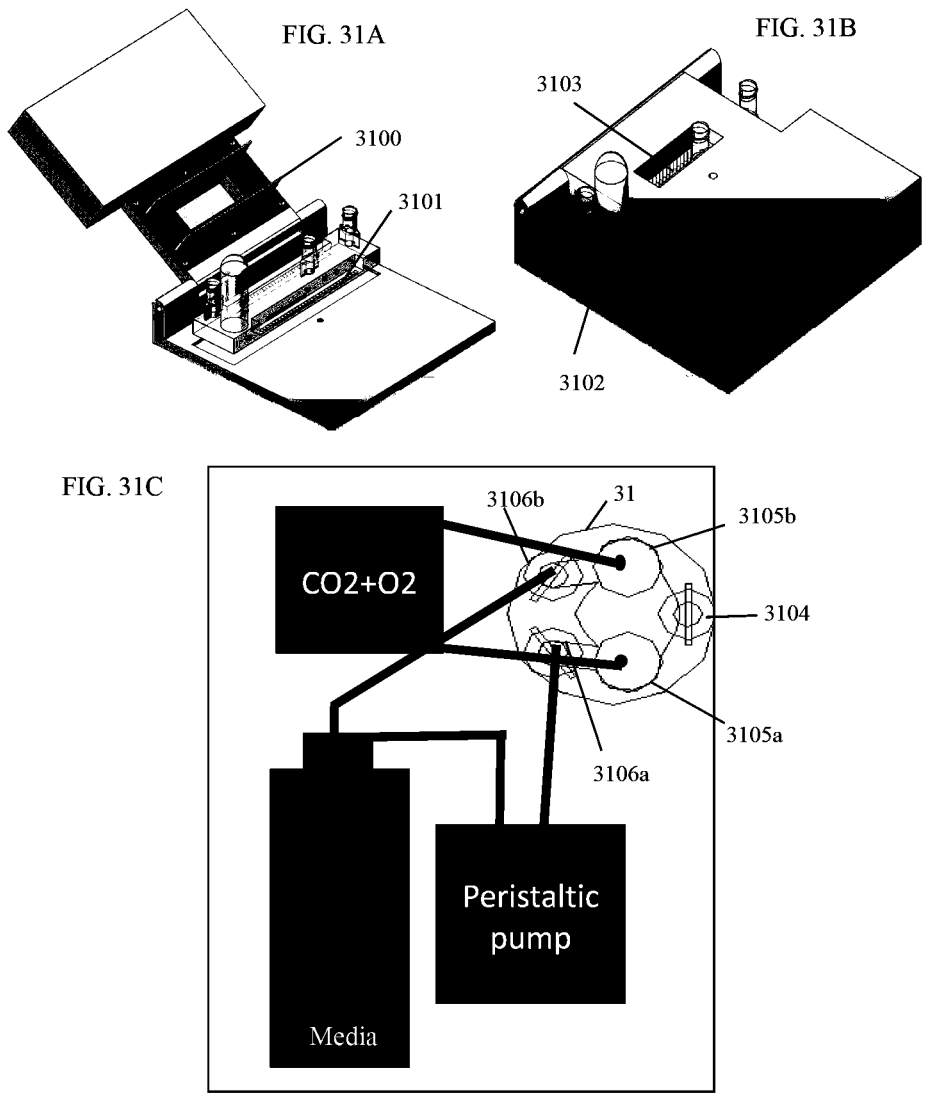

FIG. 35A
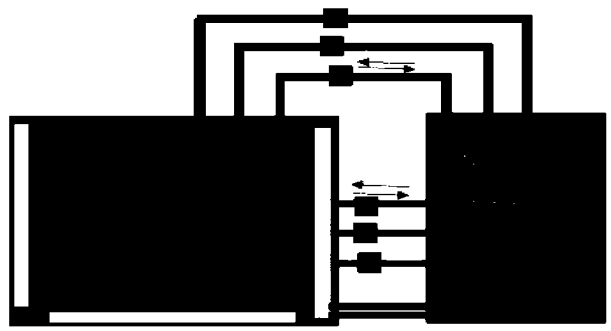
FIG. 35B
3500
3501
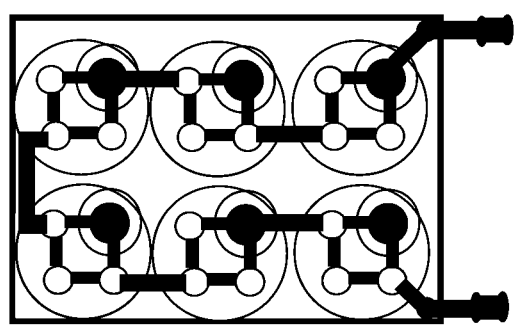
FIG. 35C
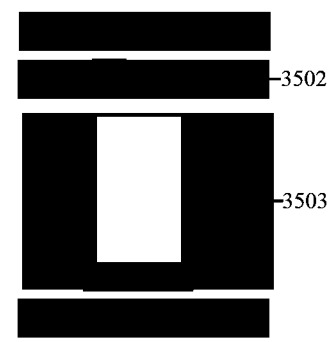
3502
3503
FIG. 35D

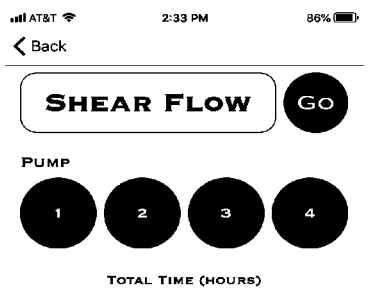
FIG. 39A
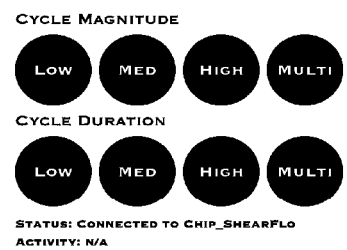
FIG. 39B
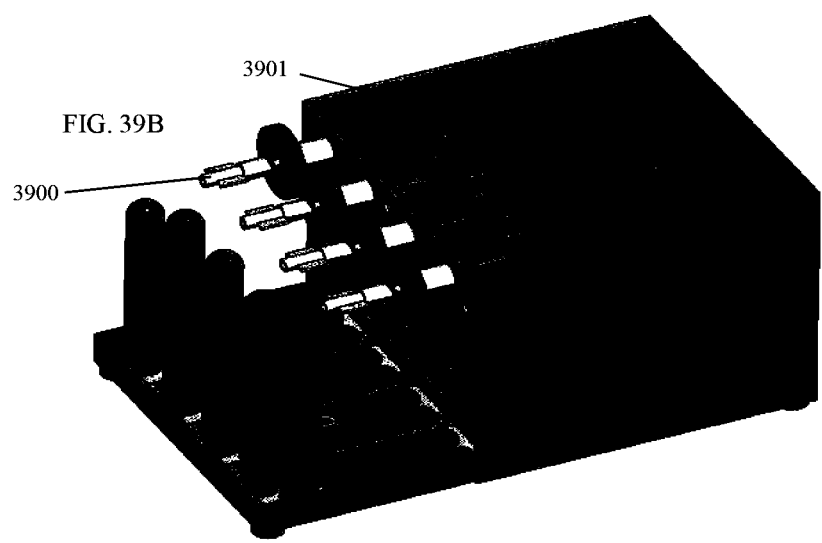

FIG. 40C
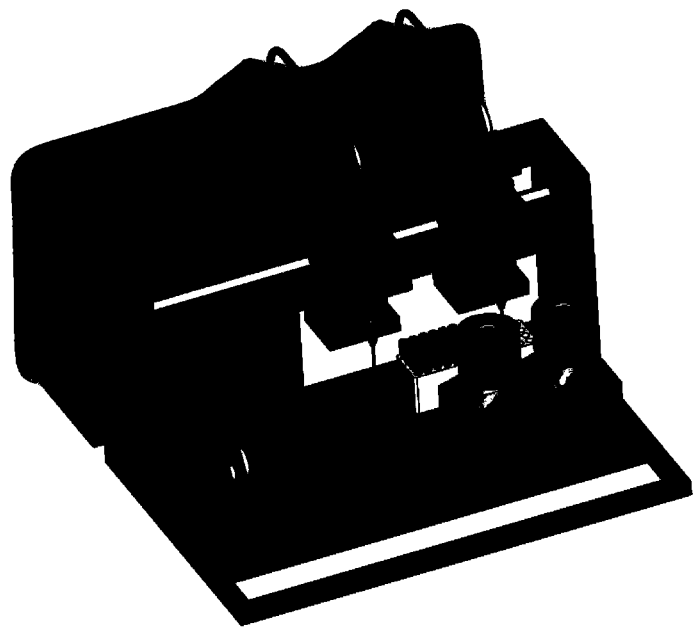
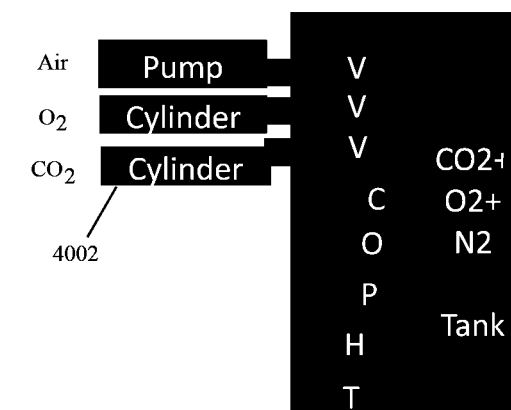
FIG. 40D

FLUIDIC ARRAY SYSTEMS AND TESTING FOR CELLS, ORGANOIDS, AND ORGAN CULTURES

CROSS-REFERENCE TO RELATED APPLICATIONS

This application is a non-provisional of, and claims the benefit of priority from, U.S. Provisional Patent Application No. 62/908,201 filed Sep. 30, 2019

STATEMENT REGARDING FEDERALLY-SPONSORED RESEARCH AND DEVELOPMENT

This invention was made with Government support under contract No. 1R43GM133233-01 awarded by the National Institute of Health (NIH). The Government has certain rights in this invention.

FIELD OF THE INVENTION

The present invention generally relates to medical devices and methods, and more particularly to microfluidic devices and methods for array devices for culturing and testing cells, organoids and organs.

BACKGROUND OF THE INVENTION

Microfluidic systems provide remarkable features for providing physiological flow in cells, organs and organoids culture. Several diagnostics and therapeutic assays require an array of devices to perform several testings. gravity-driven flow is a simpler solution for integrating a fluidic system because they offer low shear rates to cells or organs. A high flow rate is needed in some organs or cells. Unidirectional flow through organs is also required for simulating the physiological conditions. Reproducing these cell co-culture system in an array is important to study drugs and assays.

SUMMARY

The present invention is directed to systems, chips, plates and methods for cells, organs, organoids, multiple organs culture in 1-D, 2-D or 3-D arrays using microfluidics equipped with micropumps, valves, volume metering, pressure or physical parameters monitoring, PID control on temperature, pressure, gaseous concentrations and composition as shown in and/or described in connection with at least one of the figures, and as set forth more completely in the specification.

In accordance with an aspect of the present invention, there are provided methods for performing gravitation driven recirculations in 2-D or 3-D for cells, organs, organoids or multiple organs using at least two or more wells.

In accordance with another aspect of the present invention, there are provided systems with unidirectional recirculation using multiple wells forming one or more loops.

In accordance with yet another aspect of the present invention, there are provided methods for gravity-driven recirculation by tilting the chip using linear motors.

In accordance with yet another aspect of the present invention, there are provided methods to deliver cells, organoids or organs through multiple inlets into chambers.

In accordance with another aspect of the present invention, there are provided methods for performing perfusion using a fresh media inlet and a waste media outlet.

In accordance with yet another aspect of the present invention, there are provided methods for performing gravity-driven flow using two or more wells or tubes.

In accordance with yet another aspect of the present invention, there are provided methods to perform gravity-driven flow using linear motors at the corner of the chips while giving way for microscopic imaging of the cells or organs.

In accordance with yet another aspect of the present invention, there are provided methods for fabricating the chips using layers of cell adherence layers, channels, wells, elastic caps and dispenser lids with tips.

In accordance with yet another aspect of the present invention, there are provided methods for tilting the plate or chips using linear motors arranged in the top so that the system can be placed on a microscope that enables inverted microscopic imaging In accordance with yet another aspect of the present invention, there are provided methods for chips or plates forming standard well plate format with provision for adding and removing media using a microfluidic lid.

In accordance with yet another aspect of the present invention, there are provided methods for connecting multiple wells forming a loop so that recirculation of media can be accomplished by gravity-driven flow.

In accordance with yet another aspect of the present invention, there are provided methods for connecting multiple organ systems independently for perfusion with separate inlets and outlets originating and exiting by binary split channels.

In accordance with yet another aspect of the present invention, there are provided methods for delivering and removing media using a set of multichannel peristaltic pumps.

In accordance with yet another aspect of the present invention, there are provided methods for separating disposable and non-disposable components in peristaltic pumping.

In accordance with yet another aspect of the present invention, there are provided methods for recirculating media in multiple organs with multiple sizes, through multiple loops.

In accordance with yet another aspect of the present invention, there are provided methods for programming recirculations in multiple organs with multiple resident times and multiple shear rates across organs.

In accordance with yet another aspect of the present invention, there are provided methods for a perfusion system for an automatic culture of multi-organs and microscopic observations.

In accordance with yet another aspect of the present invention, there are provided methods for accomplishing cell or organs culture using transwell plates or multiple layer inserts in wells and performing recirculations.

In accordance with yet another aspect of the present invention, there are provided methods for pumping media across multiple twist compounded loops for recirculating media on multiple organs.

In accordance with yet another aspect of the present invention, there are provided methods for applying 2-D gravity-driven pumping and high shear flow using vacuum and pressure simultaneously or one after another in the same chip or plate.

In accordance with yet another aspect of the present invention, there are provided methods for delivering cell or cell in gel in channels connecting wells and performing recirculations.

In accordance with yet another aspect of the present invention, there are provided methods for creating organ systems in an array for performing drug testing on organs in multiple copies.

In accordance with yet another aspect of the present invention, there are provided methods to create multiple wells in a standard well of a well plate and interacting cells or organs through well-inserts on the top of sub-wells or the entire wells and performing recirculation within the sub-wells.

In accordance with yet another aspect of the present invention, there are provided methods to load each well of a standard well plate with inserts and perform recirculations across multiple wells using gravity-driven flow In accordance with yet another aspect of the present invention, there are provided methods for providing standard well plates with circular open channels for culturing cells or organs or vascular tissues and providing recirculation of media by oscillating with orbital mixers.

In accordance with yet another aspect of the present invention, there are provided methods for culturing cells, organs or organoids in different segments of circular channels in well plates.

In accordance with yet another aspect of the present invention, there are provided methods for open circular channels using semi-circular channels and connecting bridge channels.

In accordance with yet another aspect of the present invention, there are provided methods for performing cell or organ culture in multiple concentric circular channels and connecting them radially using side radial channels.

In accordance with yet another aspect of the present invention, there are provided methods for closing channels using lids with or without filters to transfer gases under closed cell culture.

In accordance with yet another aspect of the present invention, there are provided methods for delivering cell, organs or media using pipettes or syringes through a larger circular opening in the channels at certain locations.

In accordance with yet another aspect of the present invention, there are provided methods for injection molding one or more concentric circular channels with or without connecting channels using a single molding process.

In accordance with yet another aspect of the present invention, there are provided methods for co-culturing multiple cells or organs in concentric closed channels with multiple wells at corners for media circulation through multidirectional tilting of a plate.

In accordance with yet another aspect of the present invention, there are provided to connect adjacent channels by radial channels for co-culturing multiple cells or organs.

In accordance with yet another aspect of the present invention, there are provided methods for recirculation of media on either side of a cell or organ culture's concentric circular channels with gravity-driven flow.

In accordance with yet another aspect of the present invention, there are provided methods to recirculate media using gravity, in two-loops of channels while cell or organs are cultured in a segment or multiple segments of the channels.

In accordance with yet another aspect of the present invention, there are provided methods to co-culture cells or organs in top and bottom adjacent layers and recirculations are carried out in two set of top and bottom channels while the gravity-driven flow is enabled by wells accessible from the top.

In accordance with yet another aspect of the present invention, there are provided methods to arrange the wells that enable gravity-driven recirculations in multiple locations in a circle or inlet or outlet square or trapezoids or quadrilateral that offer different flow behavior.

In accordance with yet another aspect of the present invention, there are provided methods to culture cells or organs in a middle channel and recirculating one or more media from either side of the channel in a concentric square, circle, triangle or polygons that offer gravity-driven recirculation.

In accordance with yet another aspect of the present invention, there are provided methods to perform multiple cells or organs cultures in an array of independent recirculations from top and bottom channels.

In accordance with yet another aspect of the present invention, there are provided methods to fabricate top and bottom recirculation channel loops with open wells using multiple layers of channels and separation membrane filters.

In accordance with yet another aspect of the present invention, there are provided methods to fabricate top and bottom recirculation channel loops with extended channels to accommodate open wells that enable recirculations in both the loops.

In accordance with yet another aspect of the present invention, there are provided methods to load cells embedded in gel through an inlet into a main channel towards an outlet, without loading into side-channels that connect the inner main channels to either side of concentric recirculation loops.

In accordance with yet another aspect of the present invention, there are provided methods to separate a main channel for cell loading to side-channels through filters.

In accordance with yet another aspect of the present invention, there are provided methods to multiple organ culture system in an array for drug testing or high throughput applications.

In accordance with yet another aspect of the present invention, there are provided methods to load cells or organs in a middle channel and to carry our gravity-driven recirculations in independent adjacent channels on either side of the linear middle channel.

In accordance with yet another aspect of the present invention, there are provided methods to communicate between two adjacent channel loops to the main channel, while recirculations using an array of side-channels or finger channels.

In accordance with yet another aspect of the present invention, there are provided methods to fabricate one or more elevated wells within a well of a standard well plate or a custom well plate to store one or more reagents including inhibitors, substrates, stimulators, drugs and to dispense them into the main well by tilting at one or more of the corners.

In accordance with yet another aspect of the present invention, there are provided methods to store reagents in one or more sub-wells and spinning well plates using an orbital mixer to release one or more reagents sequentially or parallel using a combination of centrifugal forces and gravitational forces by clockwise or anticlockwise rotation of orbital mixer or other rotating devices.

In accordance with yet another aspect of the present invention, there are provided methods to increase the length of connecting channels across wells using bend channels that can transfer fluid from one well to an adjacent well.

In accordance with yet another aspect of the present invention, there are provided methods to load cells or cells in gel using a separate inlet into the channels connecting the wells.

In accordance with yet another aspect of the present invention, there are provided methods to load reagents in multiple wells in multiple well plate formats using a multichannel tip based dispenser along custom locations.

In accordance with yet another aspect of the present invention, there are provided methods for offering gravity-driven flow using a nutating mixer with variable titling angles and rotation profiles.

In accordance with yet another aspect of the present invention, there are provided methods applying high shear rate unidirectional recirculation using a set of pressure pump and vacuum pump with valves in a cyclic manner so that the fluid moves in four steps.

In accordance with yet another aspect of the present invention, there are provided methods to apply unidirectional high shear recirculation pumping for multiple wells where cell culture media is isolated whereas common air is pushed by the pumps through valves and fluidic splitters.

In accordance with yet another aspect of the present invention, there are provided methods to monitor the pressure and heights of media on each well instantaneously as a measure of continuous recirculation.

In accordance with yet another aspect of the present invention, there are provided methods for pressure or vacuum controlled by valves for recirculation from a constant PID controlled pressure or vacuum tank.

In accordance with yet another aspect of the present invention, there are provided methods for connecting pump manifold to perform recirculation in multiple wells of a standard well plate or multiple layer chip, by locking using a hinge and latch arrangement.

In accordance with yet another aspect of the present invention, there are provided methods for connecting multiple wells to a same pressure or vacuum source for recirculation using multiple layers of air flowing in either direction in channels and vias.

In accordance with yet another aspect of the present invention, there are provided methods to access cells or media in each well through a lid or lid array and accessing other connected wells in a rectangular or triangular format under closed operation.

In accordance with yet another aspect of the present invention, there are provided methods for the fabrication of multiple layers of the recirculation chip with luer connectors or manifold connection and tight lids for the open wells, air channel layers for multiplexing the wells, well layer and bottom connecting channels that connect media across wells.

In accordance with yet another aspect of the present invention, there are provided methods for performing shear stress on cells in channels connected to two tubes on either side by pushing the media on one tube towards the other tube and letting the fluid level to come back to the same height in the tubes.

In accordance with yet another aspect of the present invention, there are provided methods for loading cells in a lower channel which acts as a well to hold the cells in media or gel, so that the cells will not another top channel connecting the tubes.

In accordance with yet another aspect of the present invention, there are provided methods for performing unidirectional shear flow continuously without waiting for the media in the tube to settle down by connecting the open ends of the channel by another channel and connecting moving pressure/vacuum pulses across three segments of the channels from three tubes.

In accordance with yet another aspect of the present invention, there are provided methods for an array of shear channels to perform multiple shear rates and repeats with each channel connecting to different pressure or vacuum source.

In accordance with yet another aspect of the present invention, there are provided methods for trapping one or more organoids or one or more cells using a set of pillars in the channel and stimulating them with shear flow.

In accordance with yet another aspect of the present invention, there are provided methods stimulating multiple shear rates in separate channels using a single pump by adjusting the width of the channels.

In accordance with yet another aspect of the present invention, there are provided methods for stimulating one or more organoids or one or more cells trapped in filters attached to a layer in the channel.

In accordance with yet another aspect of the present invention, there are provided methods for delivering organoids or cells through separate inlets in channels forming a loop for unidirectional fluidic stimulation.

In accordance with yet another aspect of the present invention, there are provided methods for connecting multiple channel loops for unidirectional recirculation and perfusion.

In accordance with yet another aspect of the present invention, there are provided methods for flow stimulation of cells or organoids after trapping them within two filters on both sides and applying shear flow on one side, while the ends of the tubing are connected to 0.2 um pore size air filter.

In accordance with yet another aspect of the present invention, there are provided methods for multiple parallel channels for trapping cells or organoids within filters and applying flow stimulations.

In accordance with yet another aspect of the present invention, there are provided methods for integrated reservoir channels for pushing fluids into the cells or organoids chamber and to receive the pushed fluids for bidirectional recirculations.

In accordance with yet another aspect of the present invention, there are provided methods to perform unidirectional flow and shear stimulation using a peristaltic pump in to cell culture channels through a reservoir In accordance with yet another aspect of the present invention, there are provided methods to connect wells using ramp channels so that by adjusting the fluidic level in the wells cells can be cultured in an isolated condition and adjusting the level and/or gravity-driven recirculations to interact the cells in culture.

In accordance with yet another aspect of the present invention, there are provided methods to perform automated perfusion in a channel using pulsed fluidic flow through the top side of a tube attached to the channel.

In accordance with yet another aspect of the present invention, there are provided methods to acquire audio signals from the pumps while operation and analyzing the intensity and frequency for the flow of air and liquid in the pump to control the pumping.

In accordance with yet another aspect of the present invention, there are provided methods to deliver cells through an inlet at the middle of the channel and perfusion fluids to enter through a channel and exit through another channel while one or more tubes provide bubble trap as well as gravity-driven flow to maintain media perfusion.

In accordance with yet another aspect of the present invention, there are provided methods to separate cells culture chamber with the perfusion channels and other components.

In accordance with yet another aspect of the present invention, there are provided methods to perform perfusion of media on both sides of cell culture chambers or to flow from one chamber and exit the flow through another chamber.

In accordance with yet another aspect of the present invention, there are provided methods to disconnect a bottom cell culture channel for cell loading and connect the media perfusion through another set of top bridge channels.

In accordance with yet another aspect of the present invention, there are provided methods to homogenize the fluidic behavior across multiple bridge channels by constructing the bridge channels as width gradient or fluidic resistance gradient.

In accordance with yet another aspect of the present invention, there are provided methods to deliver multiple reagents or drugs or composition of reagents or drugs through multiple inlets for cell testing or assay.

In accordance with yet another aspect of the present invention, there are provided methods to wash the cells using a buffer or reagent between an application, a drug composition, or a completely or partial concentration.

In accordance with yet another aspect of the present invention, there are provided methods to connect a pumping system to perform pulsed fluidics for perfusion or drug concentrations preparations from a separate drug vial to deliver into a cell culture chamber.

In accordance with yet another aspect of the present invention, there are provided methods to construct multiple channels in a standard well plate format or custom format to simultaneously study multiple drugs or concentrations so that separate cells are used for a separate study.

In accordance with yet another aspect of the present invention, there are provided methods to perform electrical measurements such as field potential measurements or impedance measurements or TEER measurements across the cells in culture with fluidic, optical or electrical stimulations.

In accordance with yet another aspect of the present invention, there are provided methods to apply constant or dynamic temperature fluidic perfusion such as for 37° C. or 40° C. or/and constant or dynamic gaseous mixers such as $CO_2$, $O_2$, $N_2$ from a PID controlled tanks for microscopic monitoring assay of the cells.

In accordance with yet another aspect of the present invention, there are provided methods to culturing cells in modified T-flasks with two luer connectors, straight or bent upwards, one at the bottom and one at the top to remove waste media and to deliver fresh media respectively, in an automatic fashion.

In accordance with yet another aspect of the present invention, there are provided methods to supply gas or media or remove gas or media to the cells in culture through a special cap with luer connectors or barb connectors for easy, contamination-free, sterile and non-toxic connections.

In accordance with yet another aspect of the present invention, there are provided methods fabricate a funnel shape cap that accommodates larger filter on the cap and two larger holes that provide access for delivering fresh media or remove waste media.

In accordance with yet another aspect of the present invention, there are provided methods to supply gas for pumping media from a special vial and allowing complete removal of media through a bottom or top of the special vial.

In accordance with yet another aspect of the present invention, there are provided methods to connect multiple T-flasks for maintaining cell culture using fresh media and removal or old media.

In accordance with yet another aspect of the present invention, there are provided methods to manually replace media from the T-flask by removing the media using a syringe pump that create vacuum towards waste and by pushing clean air into a media vial to deliver media into the T-flask.

In accordance with yet another aspect of the present invention, there are provided methods to perform media exchange manually through the filter cap and any excess vacuum or gas in the waste container or media vial is isolated from the T-flask by closing a valve and letting the air through 0.2 um filter.

In accordance with yet another aspect of the present invention, there are provided methods to image the cells and transmit the image through the internet and control the cell culture fluidics.

In accordance with yet another aspect of the present invention, there are provided methods to feed an array of T-flasks from a common media bottle and remove the waste to a common bottle.

In accordance with yet another aspect of the present invention, there are provided methods to package the pumps and valves so that they can be replaced periodically depending on need and connect the electrical pins and fluidics ports with the electronics box or disposables.

In accordance with yet another aspect of the present invention, there are provided methods to develop PID control of pressure for constant pressure or vacuum source to drive the fluidics for cells or organs experiments.

In accordance with yet another aspect of the present invention, there are provided methods to circulate gases to the cells such as for stem cell cultures, hypoxia experiences or closed system experiments.

In accordance with yet another aspect of the present invention, there are provided methods to circulate gases for cell culture through a top gas inlet/outlet across several wells in a standard well plate or custom well plate.

In accordance with yet another aspect of the present invention, there are provided methods to control shear on cells cultured in 96 well plates or inserts using low angle cones connected to each well through small DC motor array and high precision linear motors suspending the DC motors connecting cones into the wells to preset heights.

In accordance with yet another aspect of the present invention, there are provided methods to dissociate primary cells including cancel cell aggregates into single cells using high shear flow stress of suspended tissues so that multiple iterations of shear recirculations applied across a set of wells and multiple stages in small channels so that increased shear circulations are applied across stages.

In accordance with yet another aspect of the present invention, there are provided methods to bond fluidic plastic devices with glass using medical adhesives and to bond fluidic plastic devices with plastics using thermal bonding, solvent bonding or ultrasonic bonding.

In accordance with yet another aspect of the present invention, there are provided methods for the automated fabrication of a multi-layer chip using peeling adhesive layers and bonding with plastic or glass layers.

In accordance with yet another aspect of the present invention, there are provided methods to measure flow rate of gravity-driven fluidic recirculations using flow-induced electrical admittance measurements or optical measurements or electrical capacitance measurements.

In accordance with yet another aspect of the present invention, there are provided methods to measure field potential measurements or electrical impedance from cells with the well plates or fluids within the well plates or flow within the well plates using interdigitates electrodes.

In accordance with yet another aspect of the present invention, there are provided methods to communicate to electrical devices that operates fluidic pumps or valves or sensors using firmware and a smart device App.

In accordance with yet another aspect of the present invention, there are provided methods to sterilize cell culture devices using ozone treatment and UV radiation treatment with flow based recirculations.

In accordance with yet another aspect of the present invention, there are provided methods to develop an independent cells and organs culture system with $CO_2$, $O_2$, $N_2$ control in a pressure-controlled tank to provide environment for culture.

In accordance with yet another aspect of the present invention, there are provided methods to provide media exchange, addition or removal using syringe need injection from culture wells to waste and fresh reservoirs to culture wells in a closed system and sterility is maintained by flame sterilization in the system or using new sterilizable syringe needle for well to well injection.

Further aspects, elements and details of the present invention are described in the detailed description and examples set forth here below.

BRIEF DESCRIPTION OF THE DRAWINGS

The embodiments set forth in the drawings are illustrative and exemplary in nature and not intended to limit the subject mater designed by the claims. The following detailed description of the illustrative embodiments can be understood when read in conjunction with the following drawings, where like structures are indicated with like reference numerals in which:

FIG. 22B presents an exemplary diagram of unidirectional recirculation using high shear flow in a single loop shear chip.

FIG. 26A presents an exemplary diagram of organoids with filters on either side of flow in a linear channel where the flow is operated from two reservoirs.

FIG. 26B presents an exemplary diagram of parallel organoids channels with filters on either side of flow in a linear channel where the flow is operated from two reservoirs.

FIG. 26C presents an exemplary diagram of a side view of different layers of organoids channels with filters on either side of the flow.

FIG. 26D presents an exemplary diagram of organoids channels with fluidic reservoirs integrated with serpentine channels.

FIG. 29A presents an exemplary 3D diagram of two inlets multiple concentration generator fluidic chip.

FIG. 29B presents an exemplary diagram of multiple fabrication layers of the two inlets multiple concentration generator fluidic chip.

FIG. 29C presents an exemplary block diagram of the process steps in the multiconcentration generator.

FIG. 31A presents an exemplary diagram of a manifold for measuring field potential signals from a two inlet multiple concentration generator fluidic chip.

FIG. 31B presents an exemplary diagram of the manifold in a closed position, which applies pressure to a plurality of spring-loaded connectors on the two inlets multiple concentration generator fluidic chip.

FIG. 31C presents an exemplary diagram of a heat and gaseous mixture control on a perfusion chip for imaging.

FIG. 35A presents an exemplary diagram of a temperature-controlled recirculation cell culture system connected to a pumping system.

FIG. 35B presents an exemplary 3D diagram of an electromechanical pumping block with electrical power inlets and pneumatic outlets.

FIG. 35C presents an exemplary diagram of a temperature and gas controlled system allowing gas and heat exchanged in to wells.

FIG. 35D presents an exemplary diagram of a side view of multiple layers in the fabrication of a chip.

Figure 36A:
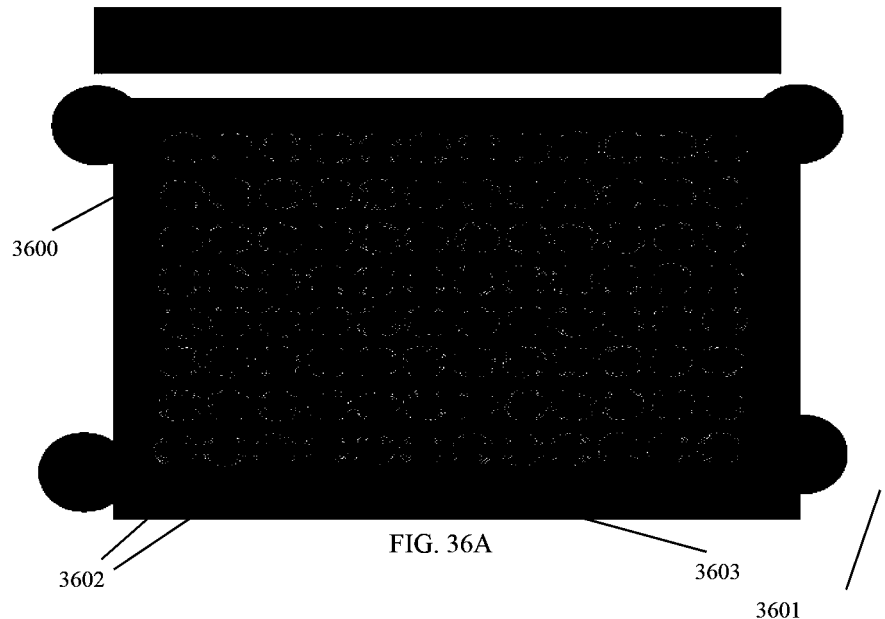

FIG. 36A presents an exemplary diagram of a cone and plate shear flow system for a 96 well plate.

Figure 36B:
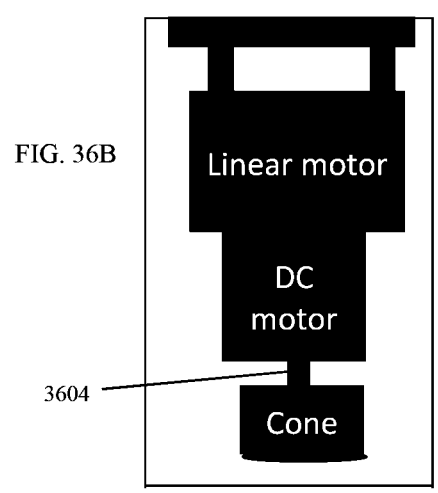

FIG. 36B presents an exemplary diagram of suspended precisely positioned cones in the 96-well plate.

Figure 37:
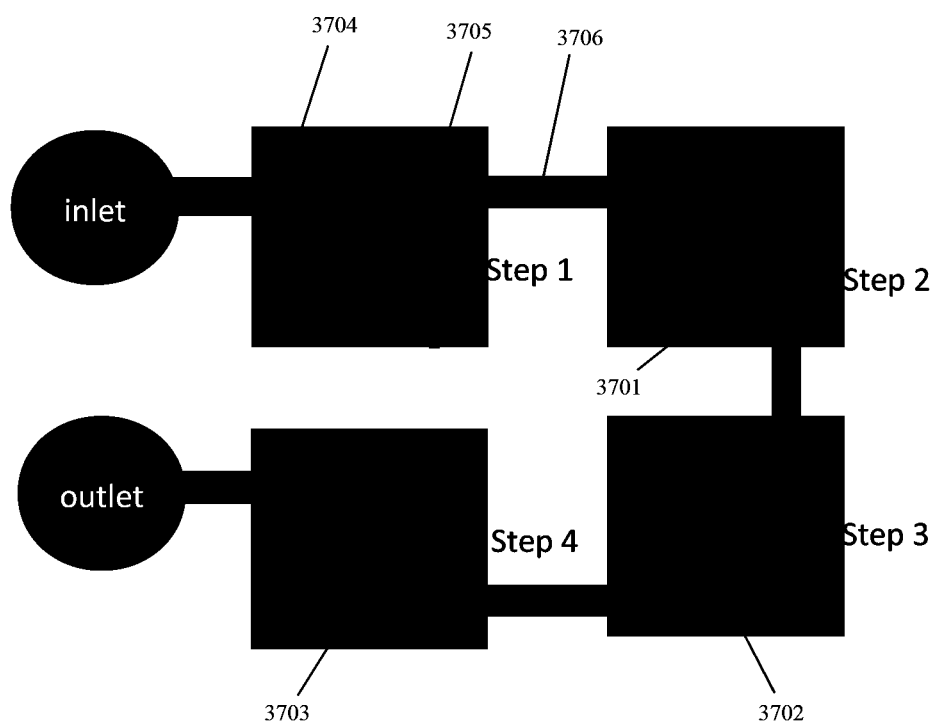

FIG. 37 presents an exemplary diagram of a microfluidic device for mechanical dissociation of cell aggregates into single cells.

Figure 38A:
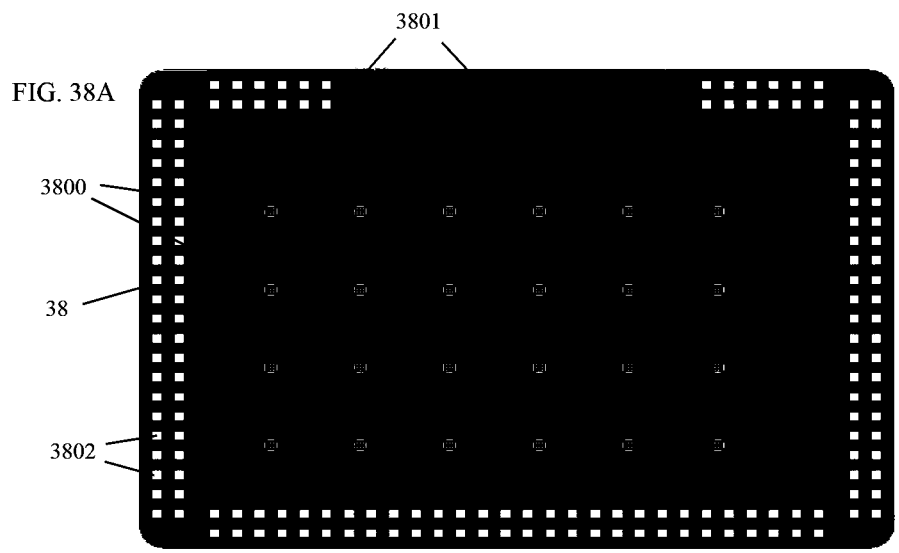

FIG. 38A presents an exemplary diagram of an organ system characterization for flow profile and measurements of filed potential signals.

Figure 38B:
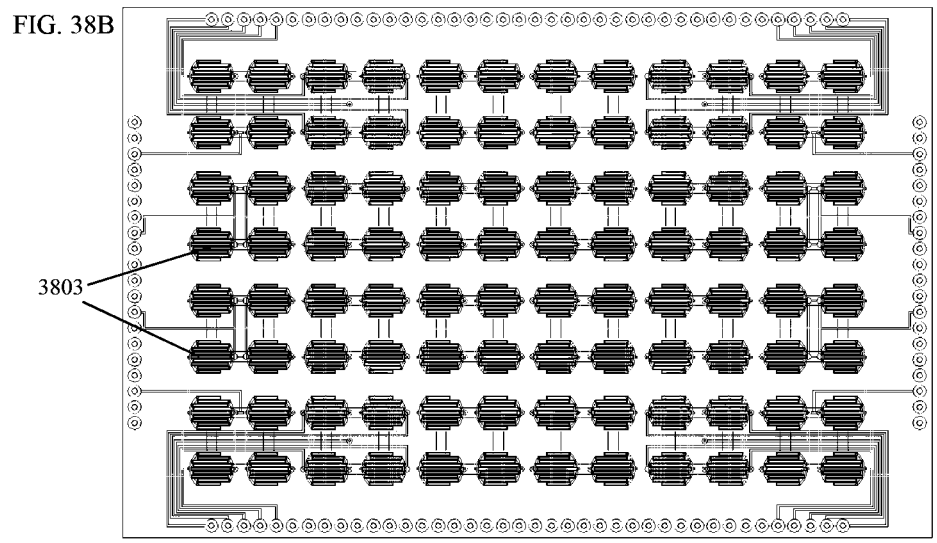

FIG. 38B presents an exemplary diagram of fast capacitance/impedance measurements to track flow profile or liquid movement.

FIG. 39A presents an exemplary diagram of a software interface to multiple pumps and shear cycle programming on a smart phone app.

FIG. 39B presents an exemplary diagram of hardware interface to multiple pumps and multiple shear flow to chips.

Figure 40A:
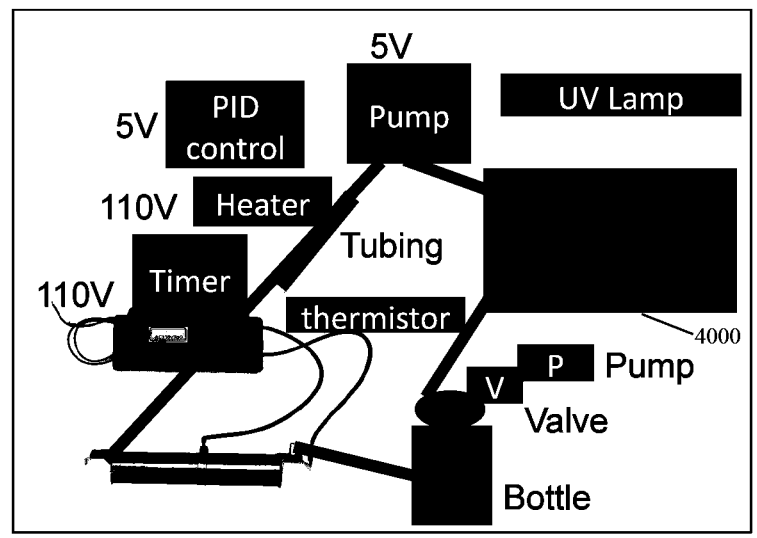

FIG. 40A presents an exemplary diagram of sterilization of chips using ozone flow.

Figure 40B:
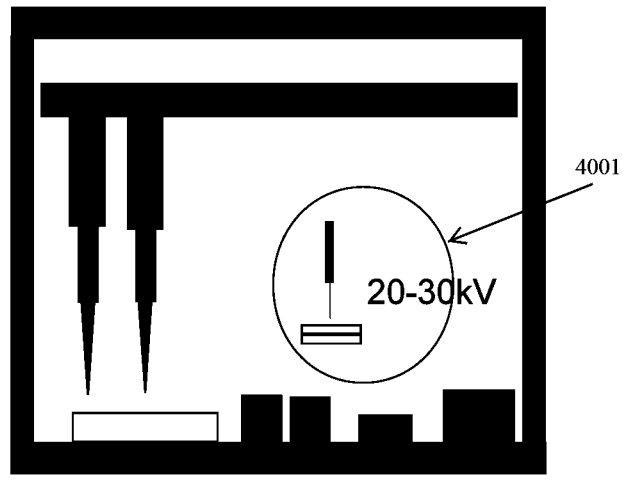

FIG. 40B presents an exemplary diagram of liquid dispensers to add or remove media or reagents from containers.

FIG. 40C presents an exemplary diagram of sterile media exchange in a standard well plate.

FIG. 40D presents an exemplary diagram of complete control of gases and temperature for well plate system.

DETAILED DESCRIPTION

The following description contains specific information pertaining to implementations in the present application. The drawings in the present application and their accompanying detailed description may be directed to merely exemplary implementations. Unless noted otherwise, like or corresponding elements among the figures may be indicated by like or corresponding reference numerals. Moreover, the drawings and illustrations in the present application may be generally not to scale, and may not be intended to correspond to actual relative dimensions.

This patent application deals with cell culture media or reagent addition, exchange, recirculation or removal in T-flasks, multi-layer flasks, hyper flasks, cell bags, bioreactors, standard well plates, chips or dishes. The addition of multiple reagent containers for mixing the reagents before delivery into the cell culture container or addition of multiple reagents directly in the cell culture containers may also be carried out. Moreover, storing reagents within an incubator for adding into the cell culture system may also be carried out. The cell culture may be extended to culturing organs or multiple organs system. Imaging the cells under a built-in microscope and controlling the fluidics after feedback imaging and pumping schemes along with volume metering and control system may also be addressed.

Organ Plate Gravitation Driven Recirculation

Figure 1A:
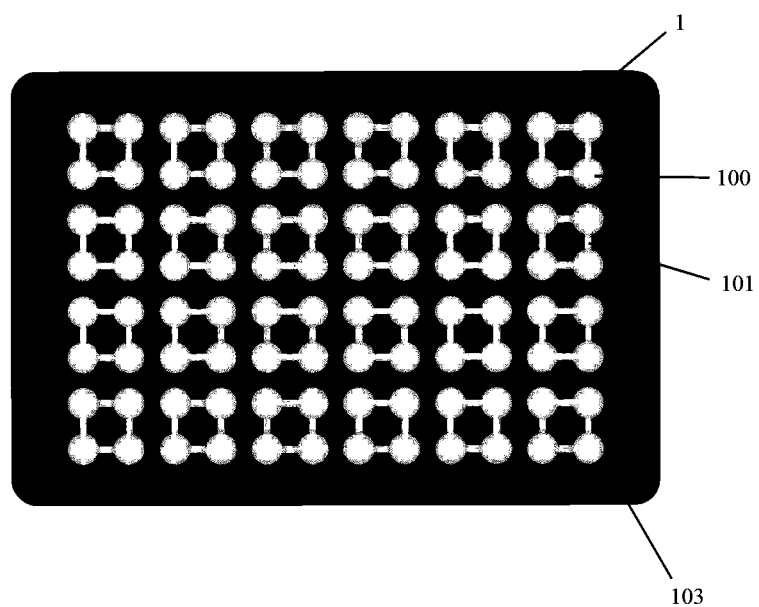
FIG. 1A presents an exemplary top-view diagram of four wells connected together to form 24 organ systems for media recirculation.
Figure 1B:
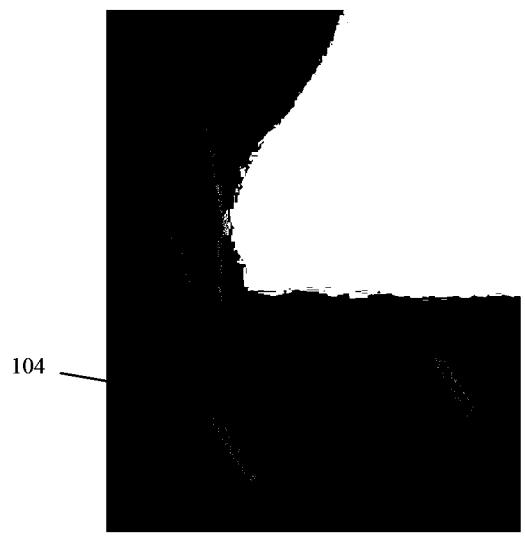
FIG. 1B presents an exemplary perspective diagram of media loaded into wells using a pipette.
Figure 1C:
FIG. 1C presents an exemplary perspective diagram of cells in gel loaded in channels for blood vessels creation.
Figure 1D:
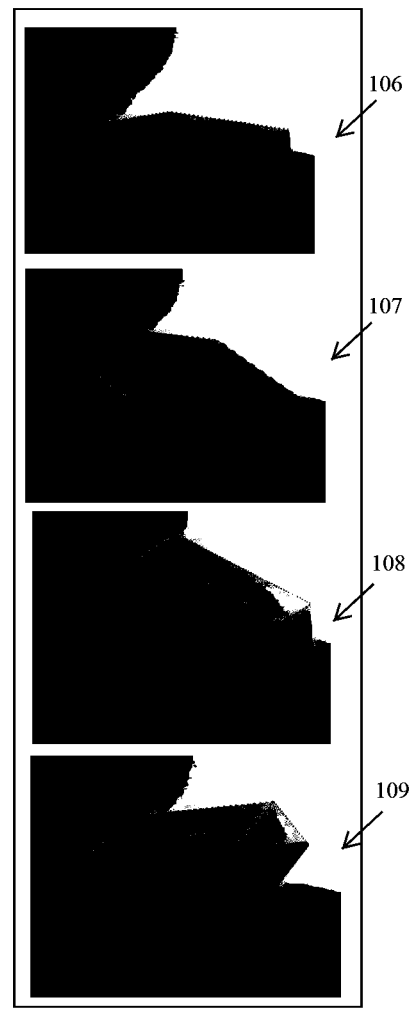
FIG. 1D presents an exemplary diagram of gravity-driven flow from one well to adjacent well by tilting in multiple directions.

In most embodiments, an organ system plate or chip 1 may be labeled like standard well plates, as in FIG. 1A, showing four wells 100 connected by channels 101 together to form 24 organ systems 103 for media recirculation. The wells may be handled using standard protocols where media may be loaded into wells using a pipette 104 as in FIG. 1B. Next, FIG. 1C shows cells in a gel 105 that may be loaded in the channels 101 for blood vessels creation. In some embodiments, the gravity-driven flow from one well to an adjacent well may be created by tilting each corner of the plate or chip 1 in the positive and negative X and Y directions 106, 107, 108, 109 as illustrated in FIG. 1D. During titling, the fluid moves to each corner wells and so with continuous titling or spinning, there will be a constant flow in to the channels 101.

Figure 2A:
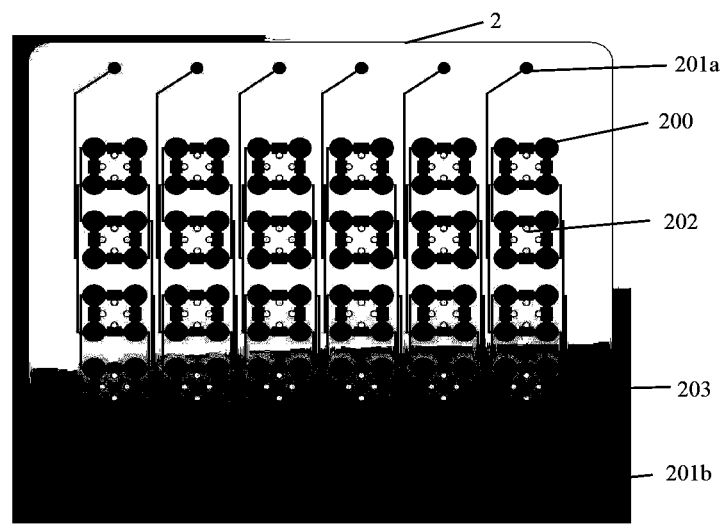
FIG. 2A presents an exemplary diagram of perfusion in four wells connected in a 96-well plate format.
Figure 2B:
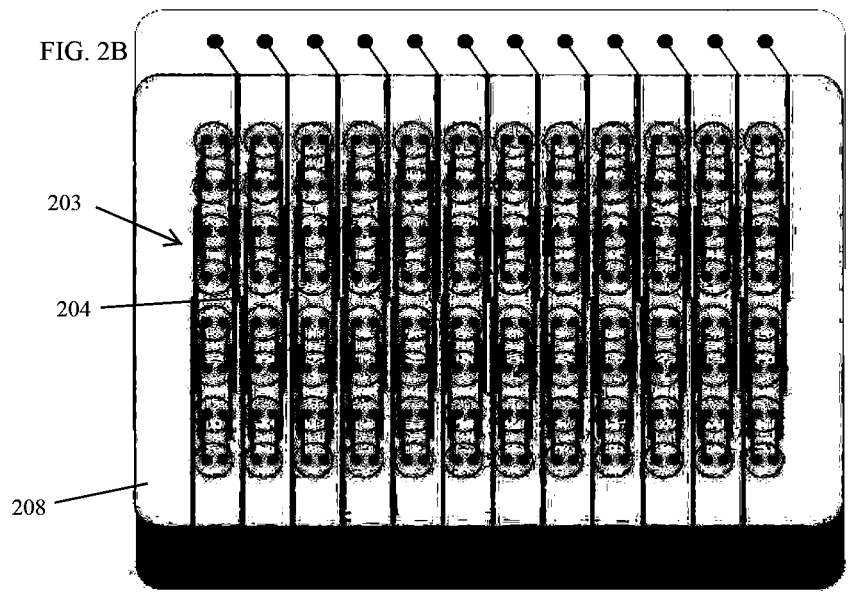
FIG. 2B presents an exemplary diagram of a 96 well plate format with perfusion inlets and outlets for each well.

Organ plate or chip 2 for gravitational driven recirculation consists of at least one of the corner wells 200, as seen in FIG. 2A, with chambers in a fluidic paths connecting the other wells 200. The chambers will have inlets to deliver cells or organs. Perfusion, passage of blood or other fluid through a blood vessel or another natural channel, can be set by letting new media into the chip 2 and letting waste media out of the chip 2 through separate ports. The gravity-driven chip 2 may be placed in a platform as shown in FIG. 2B. Gravity may be very significant for tall tubes acting as wells so that physiological shear rates may be applied to the cells or organs while in recirculation. The recirculation may be activated by a set of linear motors 206 at the corners as in FIG. 2C.

Figure 2C:
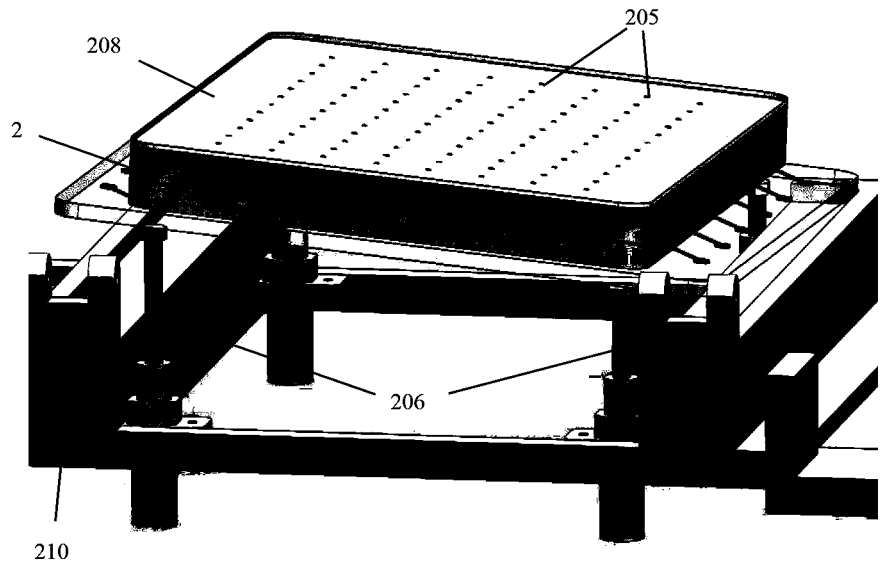
FIG. 2C presents an exemplary diagram of a 96 well plate format gravity chip on stage with linear motors activation.

One of the organ plates consists of 24 sets of 4-organ reservoirs for 6 drug concentrations inlets 201*a* and outlets 201*b* with 4 repeat cell/organ culture as seen in FIG. 2A. Each organ system 203 has four wells 200 to hold the organs and to facilitate gravity-driven recirculation fluidics. The wells 200 may be sealed at cell inlets 202 after loading one or more cells. A microfluidic lid 208 placed on top of the wells 200, as seen in FIGS. 2B-2C, may be used for transporting fluids into each of the wells 200 and to remove fluids from the wells 200 to a waste 204. The lid 208 may be fitted with filters 205 on top of the wells 200 for gas exchange during recirculation. Perfusion of reagents, media or drugs may be carried out using the microfluidic lid 208 which consists of an inlet and an outlet for all the wells 200 Each column of the wells 200 may be connected to each source of media for perfusion. The inlets and outlets may be binary split or joined independently. Each four set of wells may be connected together by channels. Cells for vascular culture may be delivered into separate ports or through the open wells 200 into the channels connecting the wells 200. A six-by-four set of organ systems may be used for drug discovery or drug testing experiments. Perfusion of media into the wells may be facilitated by multichannel peristaltic pumps with a plurality of inlet tubing and a plurality of outlet tubing for transferring fresh media and waste media, respectively. The organ plate 2 may be set into gravity-driven recirculation using linear motors 206 that may be fitted at each corner of the organ plate 2 in an opening of a microscope stage 210 as in FIG. 2C. To facilitate long term organ culture, each organ system may be connected to reagent entry and waste exit. An actuation system for recirculation may consists of a set of four linear motors 206 driven by custom current drivers which may be connected to a microcontroller. An algorithm to control linear actuators 206 cycle for varying fluidic shear in the recirculation system may be set to three levels, i.e., low, medium, and high, to perform tilt-based gravity-driven recirculation. For example, to move the fluid to a corner well, an opposite corner actuator may be set to high, an adjacent corner actuator may be set to medium and the corner actuator may be set to low. The actuation cycle may be accelerated to increase the velocity of fluids in circulation. Periodic perfusion may be performed for refreshing the organs in culture.

Figure 2D:
FIG. 2D presents an exemplary diagram of layers of the 96 well plate format gravity chip.

A glass bottom layer 207 of the organ plate 2 may be equipped with eight (8) sets of electrodes per heart or brain organ to perform field potential measurements. For example, FIG. 2D shows the layers in the organ plate 2 with a microfluidic lid 208, silicon cap 209 and wells/channels.

Figure 3A:
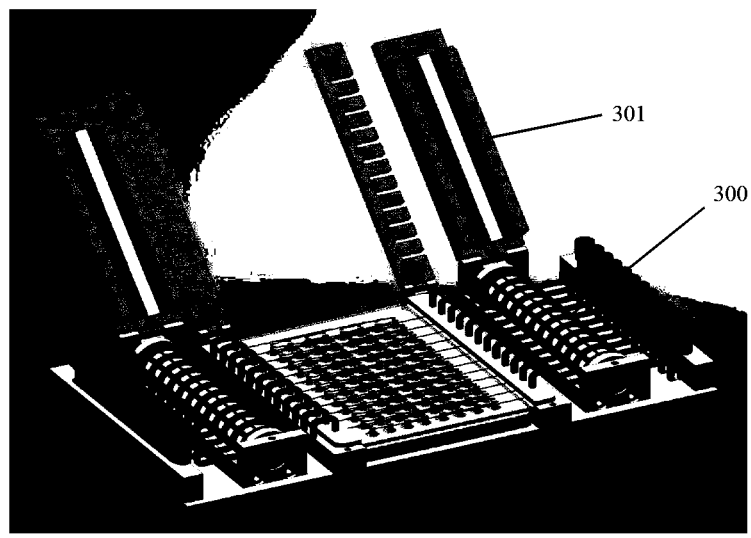
FIG. 3A presents an exemplary diagram of a multichannel peristaltic pump driving perfusion fluidics in a 96-well plate showing an open pump position for connecting tubing.
Figure 3B:
FIG. 3B presents an exemplary diagram of the multichannel peristaltic pump driving perfusion fluidics in the 96-well plate showing a closed pump position for perfusion.
Figure 3C:
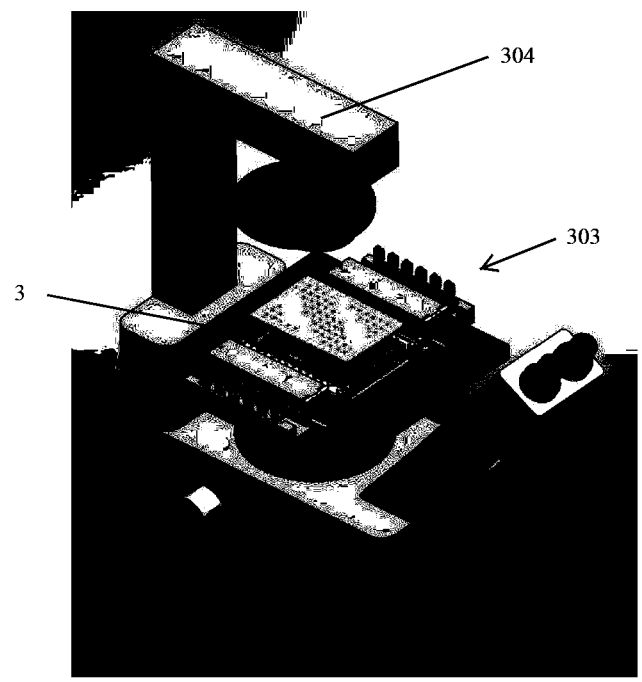
FIG. 3C presents an exemplary diagram of multi-organ plate on a microscope for imaging.

Periodic perfusion may be performed for refreshing the organ media using two (2) six-channel peristaltic pumps 300 as seen in FIG. 3A in an open state 301 and in FIG. 3B in a close state 302. Further, the organ system 303 can be adapted to a microscope 304 for optical imaging as shown in FIG. 3C.

Figure 3D:
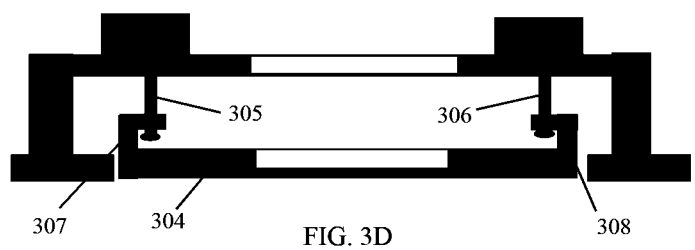
FIG. 3D presents an exemplary diagram of linear actuators movement on a stage for gravity-driven flow.

A set of six (6) ribbon silicon tubing may also be connected from the reservoirs to the plate using barb connector through the peristaltic pumps. The tubing, media/waste vials and chip may be disposables for each experiment. A custom circuit board with a driver, controller and Bluetooth interface may control the pumps using a smart device app. Multi-electrode array chips ay be used with eight (8) electrodes per well for measuring electrical activity of heart organs. Electrical field potential signals from 192 electrodes across 24 wells may be measured using three Intan RHD 2164 amplifiers connected to Intel field point gated array (FPGA). A 1 ms bipolar pulse (1V) may be applied to measure conduction velocity. Imaging using a custom software may be carried out with an XYZ stage and a camera connected to a microscope. A custom microscopic stage adapter may be developed for imaging. Optical imaging to characterize interacting-organs and immunoassay protocols may be developed to study liver metabolism from the collected waste media in each drug experiments. A manifold system may provide pressure tight fluidic operation of the pumps 300 and plate 3. In some embodiments, FIG. 3D shows a configuration where the actuator system 305, 306 sits on a microscope 304 and suspends the plate 3 through hooks 307, 308 at the tip of the linear actuators to control the tilt.

In some embodiments, each organ system 404 may have functionally scaled wells, i.e., organ wells 400, 401, to clamp/hold and culture organs from transwell inserts with vascular endothelial cells and other associated cells for example, liver or heart. Multiple parallel recirculation loops 402, 403 with multiple wells each, may be actuated simultaneously for organ interactions and to facilitate nutrient delivery to respective organs. In some embodiments, two wells may act as a spacer for future brain or muscle organs. In other embodiments, an additional well may also form a loop that enables directivity of a brain organ to interact with a heart organ alone as shown by the arrows in the channels. In most embodiments, the bottom layer of the organ plate may be equipped with multiple electrodes for the brain or heart organ to perform field potential measurements to assess toxicity.

Figure 4A:
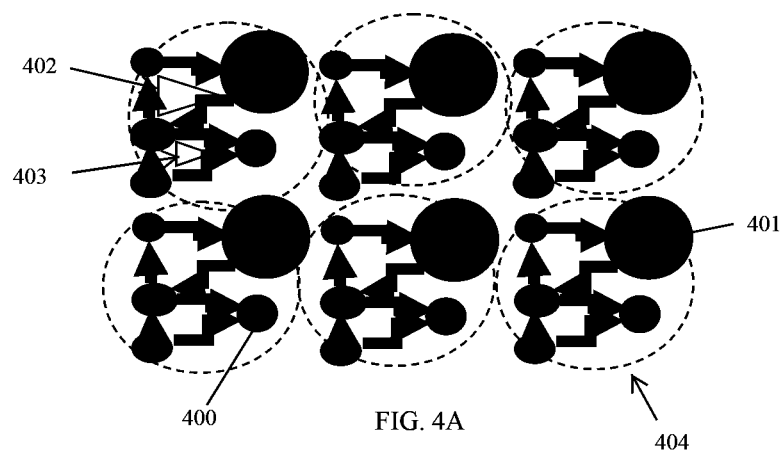
FIG. 4A presents an exemplary diagram of a multi-organ gravity-driven unidirectional recirculation 6-well plate format showing flow direction in two-loops.
Figure 4B:
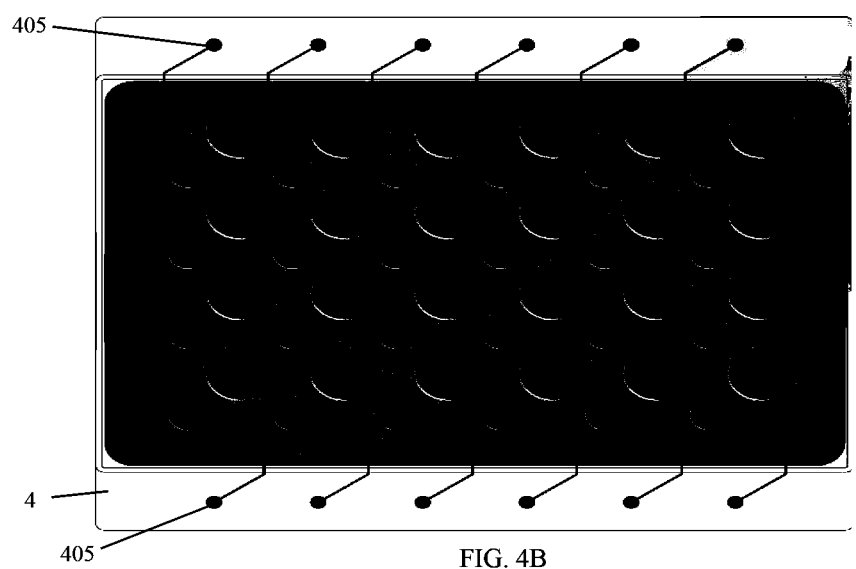
FIG. 4B presents an exemplary diagram of a multi-organ system with a perfusion microfluidic lid.
Figure 4C:
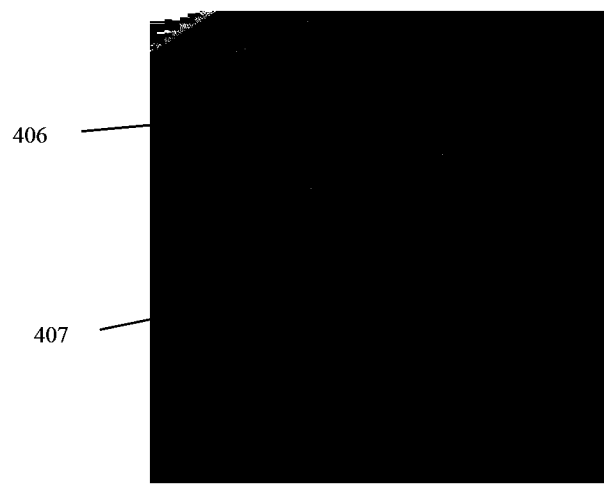
FIG. 4C presents an exemplary diagram of multi-organ plate for individual wells with transwell inserts.
Figure 4D:
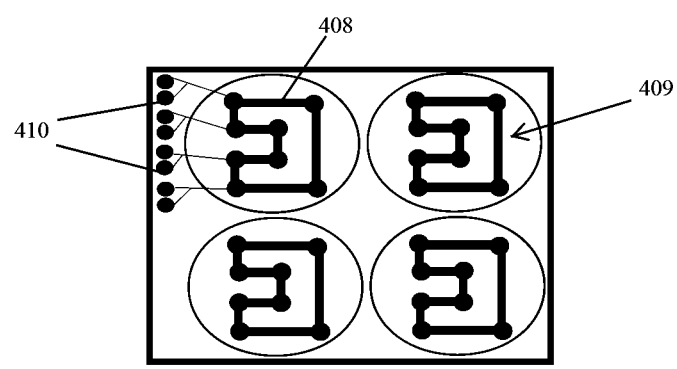
FIG. 4D presents an exemplary diagram of multi-organ plate with multiple loops, turns, and directional flow through organs.

In some embodiments, a set of 4 organ well systems may be connected in parallel to perfusion fluidics and a set of 6 organ inlet/outlet systems 405 may be used for different drug concentrations as in FIG. 4B. The organs may be introduced into the wells for maturation and a lid may be pressed on top to close of the organ system. Periodic perfusion to the organs may be carried out using peristaltic pumps to keep them refreshed. Any air bubble flowing in to the channel may be released out through a 0.2 um filter in the wells. In most embodiments, the user may select the perfusion/recirculation cycles and the system may operate the organ well systems from an incubator. In some embodiments, FIG. 4C shows the sizes of organ wells 406, 407 as a close-up view. An organ well plate may have three main layers: a bottom glass layer, a middle acrylic channels/wells/reservoirs/inlets layer and microfluidics lid layer with silicone rings to provide air-tight operations. In most embodiments, the user may introduce the organs into the organ wells and close the organ wells by pressing the lid. In some embodiments, each well may be equipped with the 0.2 um filter for the exchange of gases and allow fluidic operations. In some embodiments, the organ well plate or chip may be configured in a 96-well plate format for microscopic compatibility and may be imaged using a custom software. In one embodiment, FIG. 4D presents an exemplary diagram of the organ plate with multiple loops, turns, and directional flow through organ wells. A high shear flow may be activated in one or more segments 408 of a recirculation flow system 409 where high physiological shear flow may be required, using external pressure and/or vacuum sources 410.

Figure 5A:
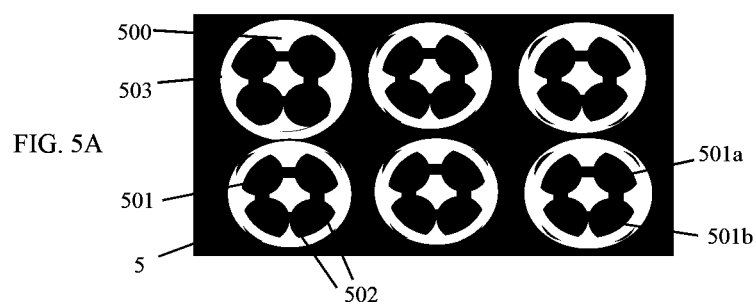
FIG. 5A presents an exemplary diagram of gravity-driven flow within sub-wells of a 6-well plate with each well carrying a transwell plate insert.
Figure 5B:
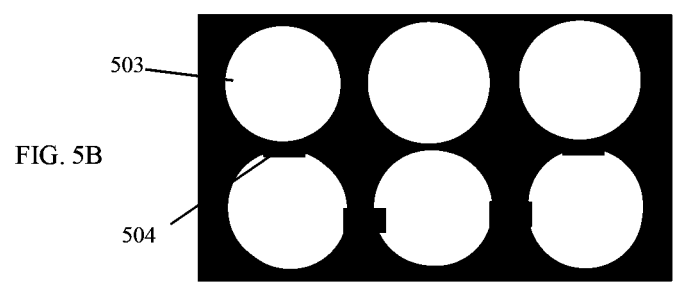
FIG. 5B presents an exemplary diagram of gravity-driven flow of every well of the 6-well plate with each well carrying the transwell plate insert.
Figure 5C:
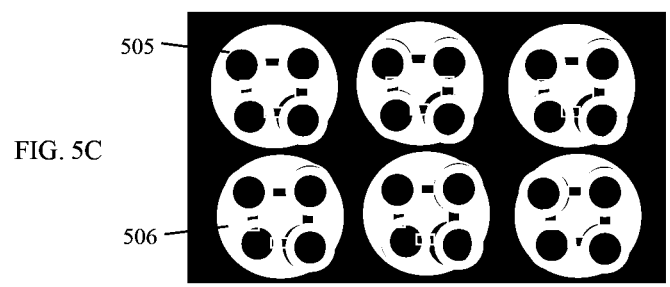
FIG. 5C presents an exemplary diagram of gravity-driven flow within the sub-wells of the 6-well plate with each of the sub-wells carrying a transwell plate insert.

In some embodiments, multiple sub-wells 501 may be designed within the wells 500 of standard well plates 5 as illustrated in FIGS. 5A-5C. Using this device 5, organs grown in a well 500 on filters or solid substrates can be transferred to the sub-wells 501 of a recirculation system for interacting with a vascular system. In one embodiment, FIG. 5A shows gravity-driven flow within the wells 501 of 6-well plate 5. The sub-wells 501 may be deeper compared to connecting sub-well channels 502 so that each sub-well 501 inside the main well 500 may be independently used for growing cells or organs. After the cells or organs may be sufficiently grown, continuous titling and gravity-driven recirculation will help to transport the metabolites from one sub-well 501a to another sub-well 501b. In the FIG. 5A, each main well 500, of the 6-well plate 50 with carries a transwell plate insert 503. In some embodiments, FIG. 5B presents a gravity-driven flow across every main well 500 of the 6-well plate 5 with each well 500 carrying the transwell plate insert 503 and the flow may be accomplished through main well channels 504. In some embodiments, FIG. 5C presents an exemplary diagram of gravity-driven flow within the main wells 500 of 6-well plate 50 with each such sub-well 501 carrying a sub-transwell plate insert 506.

Open-Channels Recirculation

Figure 6A:
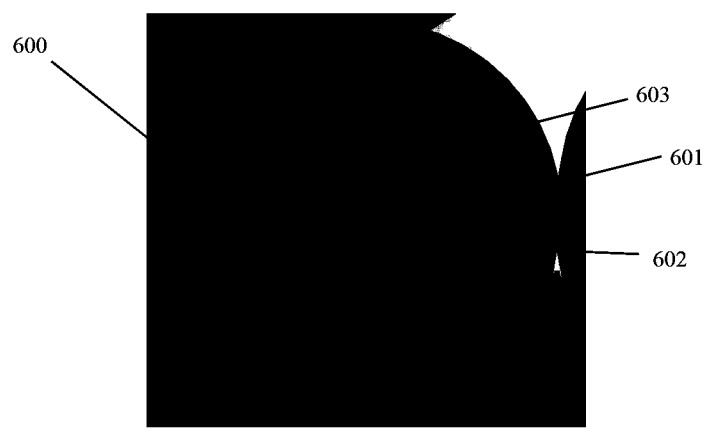
FIG. 6A presents an exemplary diagram of two circular channels separated by connecting channels.
Figure 6B:
FIG. 6B presents an exemplary diagram of the two circular channels separated by the connecting channels in a 96-well plate format.
Figure 6C:
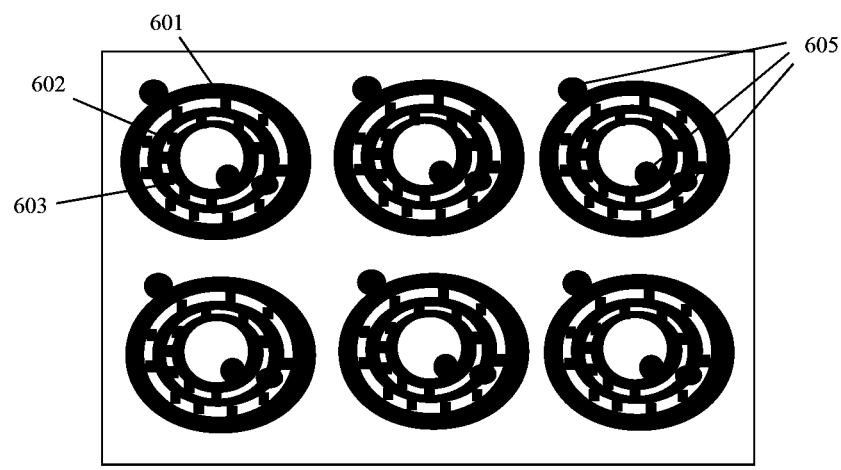
FIG. 6C presents an exemplary diagram of three circular channels separated by connecting channels.
Figure 6D:
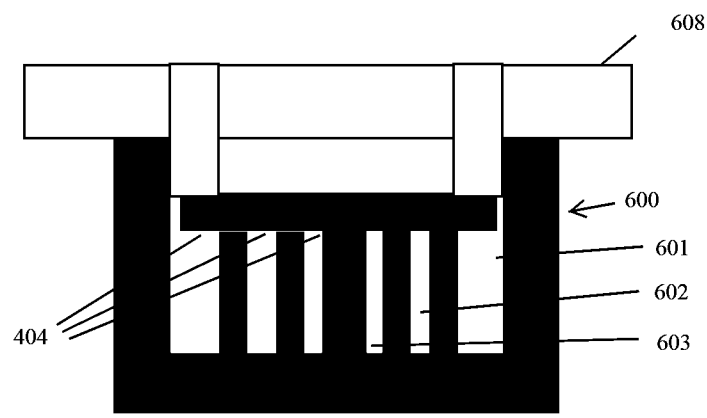
FIG. 6D presents an exemplary diagram of a lid closing an inner circular channel and an outer well across a standard well plate.

In some embodiments, circular open channels 601, 602 in a standard well plate format 60 may be manufactured using injection molding. Unlike wells, these channels 601, 602, as shown in FIG. 6A, may offer flow during axial spinning from an external machine. In most embodiments, the multiple individual circular open channels 601, 602 may be made in each well 600 in a standard well format 60 to develop vascular growth of cells. In most embodiments, multiple open channels 601, 602 may have different depths so that cells or organs in each channel 601, 602 may be grown independently. In some embodiments, connecting channels 603, as seen in FIG. 6A, may connect one or more of the channels 601, 602 to allow flow interaction during growth. In some embodiments, one or more channels, i.e. channels 601, 602, 603, as seen in FIG. 6C, may be connected by increasing the fluid volume in the channels 601, 602. In most embodiments, the system of channels 601, 602, in the well 600 may be extended to standard well format 60 as in FIG. 6B. In some embodiments, a plurality of such channels 601, 602 may be designed on well plates 6 with expanded fluid delivery sites 604 in each channel as in FIG. 6C. In some embodiments, the channels 601, 602, 603 and wells 600 may be closed airtight using a lid 608 as in FIG. 6D in the standard well plates 60.

Multi-Channels Gravity-Driven Recirculation

Figure 7A:
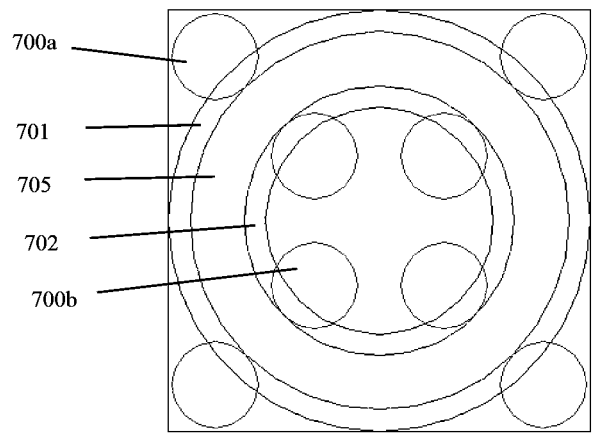
FIG. 7A presents an exemplary diagram of two recirculation loops connected by side-channels.
Figure 7B:
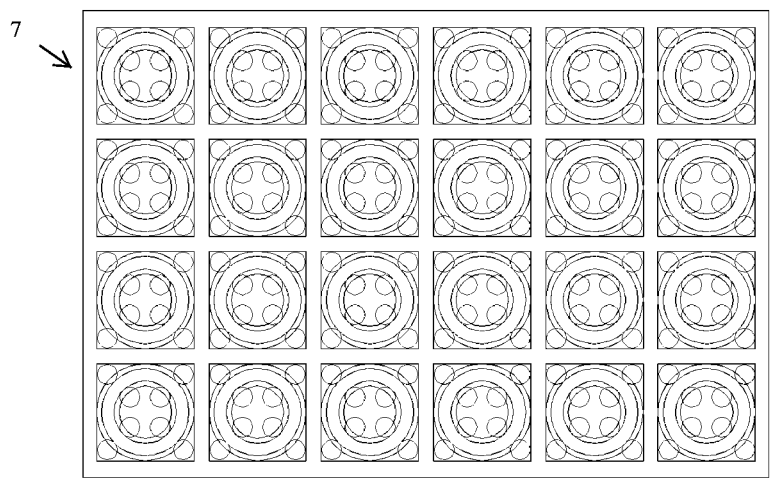
FIG. 7B presents an exemplary diagram of the two recirculation loops in a 96-well plate format.
Figure 7C:
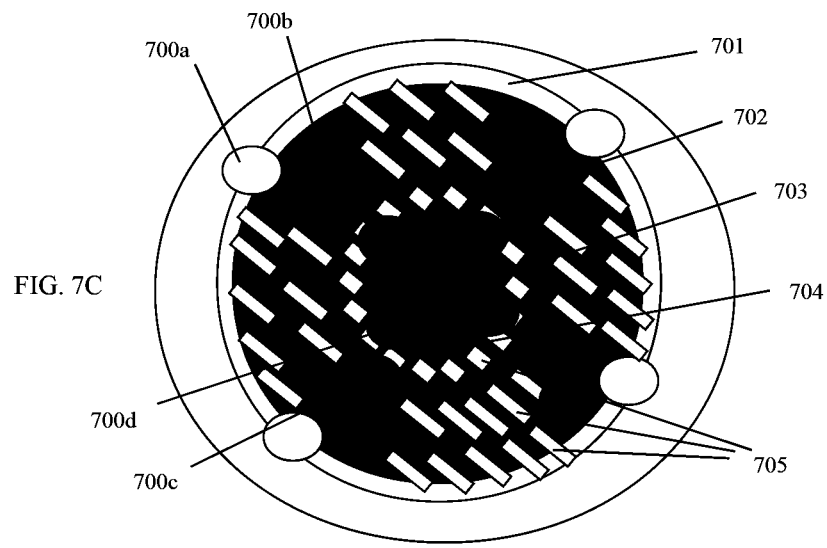
FIG. 7C presents an exemplary diagram of multiple recirculation loops connected by side-channels.
Figure 7D:
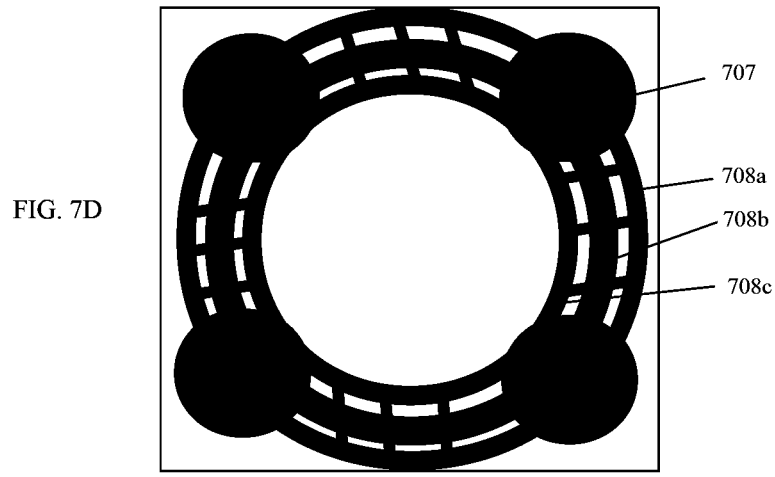
FIG. 7D presents an exemplary diagram of multiple recirculation loops connected by wells and side-channels.

Gravity-driven recirculation may be extended to multiple channels and connecting multiple recirculation channels through side-channels for interaction. In some embodiments, two-channel recirculation channels 701, 702 may be powered by a set of 4 corner wells 700a connected by the outer channel 701 and the inner channel 702 as shown in FIG. 7A. In most embodiments, connecting channels 705 may radially connect both the recirculation loops 701, 702. The recirculation channels 701, 702 may be extended to standard well plates 7 such as 96-well plate format 70 as in FIG. 7B. In some embodiments, multiple recirculation loops 701, 702, 703, 704 may be powered by gravity through wells 700a, 700b, 700c, 700d as shown in FIG. 7C. In some embodiments, in the case of recirculation using sample media same set of 4 corner wells 707 may be used as in FIG. 7D. In some embodiments, at least one of the multiple loops of channels 708a-708c may be in multiple layers or heights.

Figure 8A:
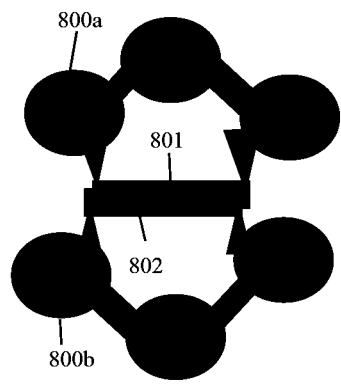
FIG. 8A presents an exemplary diagram of two recirculation loops with channels separated by a filter membrane.
Figure 8B:
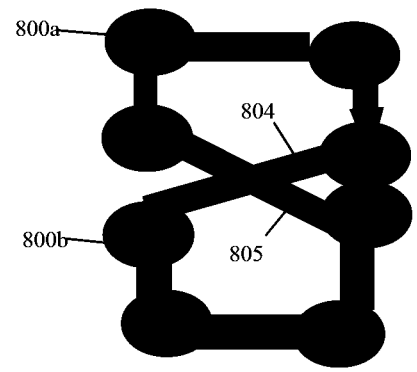
FIG. 8B presents an exemplary diagram of two overlapping recirculation loops with channels separated by a filter membrane.
Figure 8C:
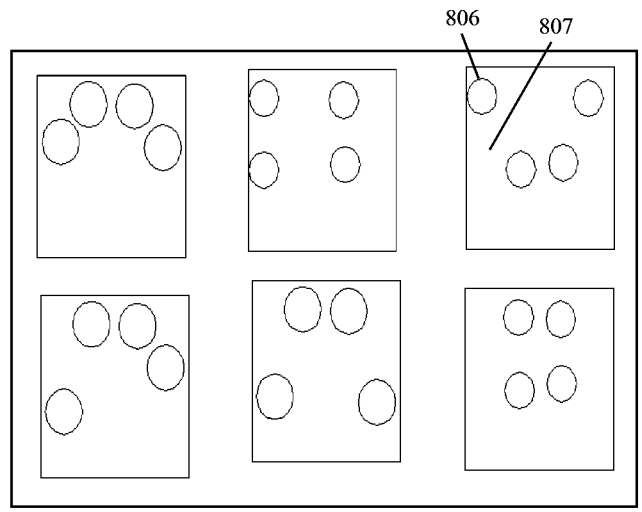
FIG. 8C presents an exemplary diagram of multiple configurations of two sets of wells from both the recirculation loops.
Figure 8D:
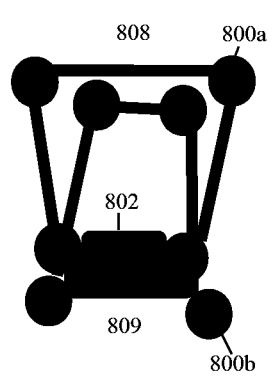
FIG. 8D presents an exemplary diagram of two overlapping recirculation loops with the flow in the same direction through channels separated by a filter membrane.

The cells may be placed in channels which may be placed one over another using membrane filters. In some embodiments, as illustrated in FIG. 8A, two channels 801, 802 may be placed one over another using a membrane filter 803, not shown, and both the channels 801, 802 may be power through gravity by a set of three wells 800a for the top loop 801 and a second set of three wells 800b for the bottom loop 802. In some embodiments, the channels 804, 805 interacting with the cells may be overlapping and each may be powered by four set of wells 800a, 800b as in FIG. 8B. In some embodiments, variations on the configuration of top layer wells 806 and bottom layer wells 807 may control the path of flow in the channels, i.e. channels 801, 802, 803, 804 from FIGS. 8A-8B. For example, six (6) designs are presented in FIG. 8C. In some embodiments, during gravity based flow each loop may experience flow in an opposite direction from one channel over another channel. However, the flow direction in each channel may be made to flow in a same direction by orienting the wells 800a, 800b as in FIG. 8D. To develop the flow in the top and bottom channels 801, 802 in the same direction, half of each set of the top and bottom wells 800a, 800b may be placed on one side 808 of their respective channels 801, 802 and the other half of each set of the top and bottom wells 800a, 800b on the other side 809 of their respective channels 801, 802.

Figure 9A:
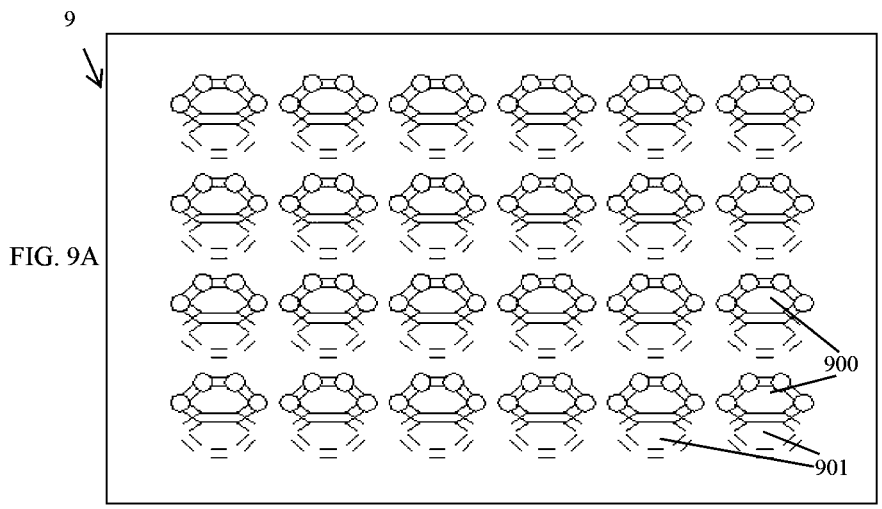
FIG. 9A presents an exemplary diagram of two sets of recirculation channels side by side in a 96-well plate format.
Figure 9B:
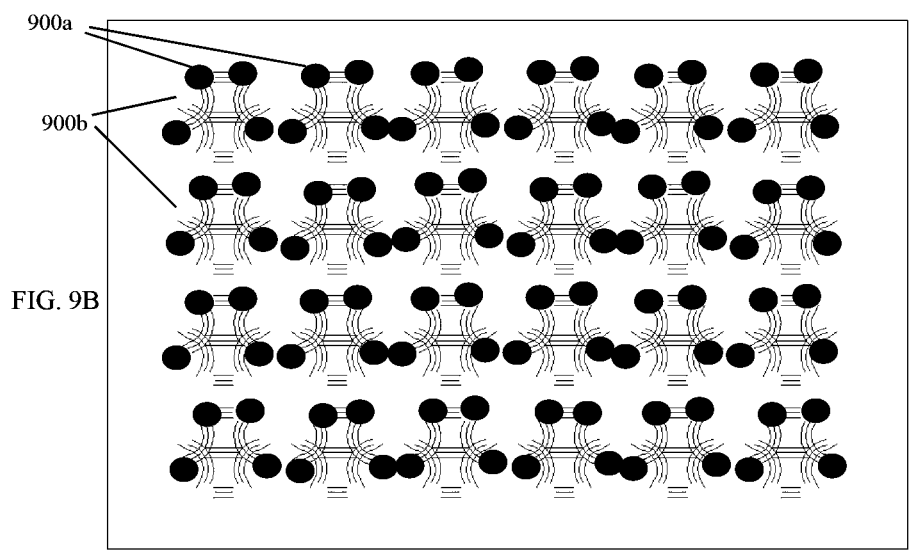
FIG. 9B presents an exemplary diagram of 96-well plate format with two overlapping recirculation loops with channels separated by a filter membrane.
Figure 9C:
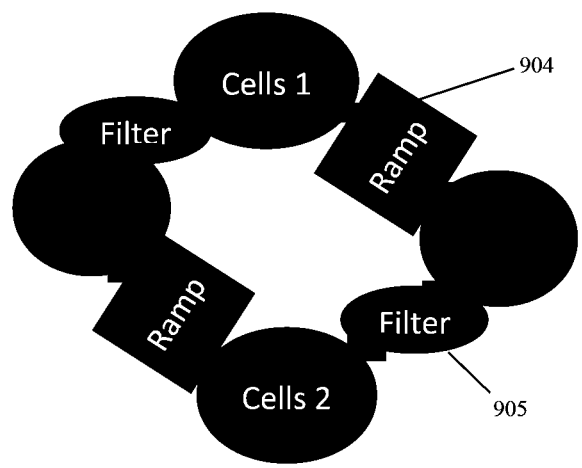
FIG. 9C presents an exemplary diagram of a recirculation unit with ramps and filters in between cell culture wells.
Figure 9D:
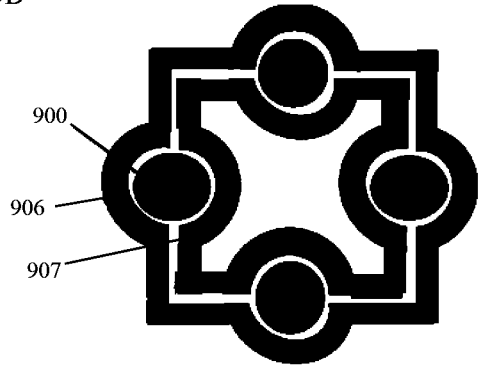
FIG. 9D presents an exemplary diagram of co-channel at different levels around cell culture wells in the recirculation flow.

In some embodiments, two-loops recirculation channels may connect a top loop 901a and a bottom loop 901b through a separating filter may be presented in 96-well format 90 as seen in FIG. 9A. Such chip 90 may be fabricated by multiple layers forming wells 900 and channels 901. In some embodiments, one set of wells 900a (solid) may drive the top channel 901a and other set of wells 900b (hollow) may drive the bottom channel 901b as in FIG. 9B. In most embodiments, a recirculation loop ramp channels 904 and filters 905 may be introduced to isolate fluid to compartmentalize and separate the components of the fluids from one well to another well as illustrated in FIG. 9C. In some embodiments, co-channels 906, 907 may be developed on either side of at least one of the wells 900 at different depths for recirculation and to enable vacularization of cells or organs as in FIG. 9D.

Figure 10A:
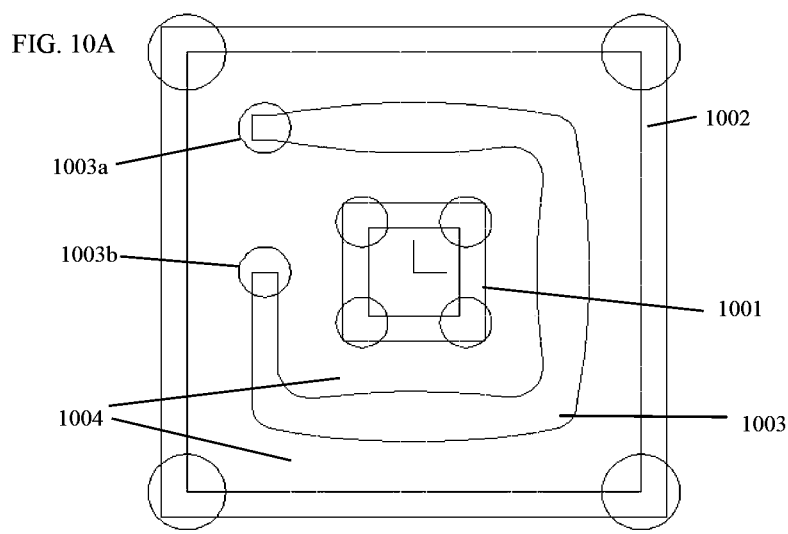
FIG. 10A presents an exemplary diagram of two recirculation loops side by side with channels where cells embedded in gel are present.
Figure 10B:
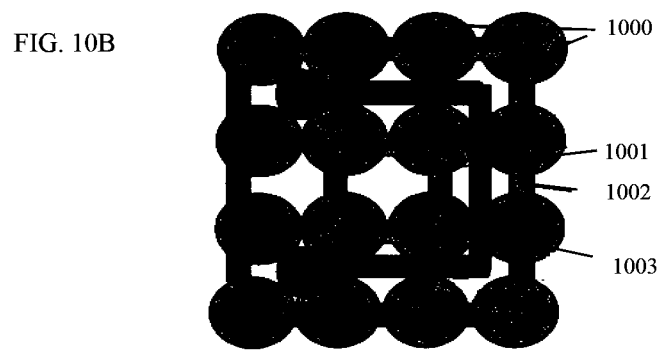
FIG. 10B presents an exemplary diagram of two recirculation loops with channels and multiple wells at different depths.
Figure 10C:
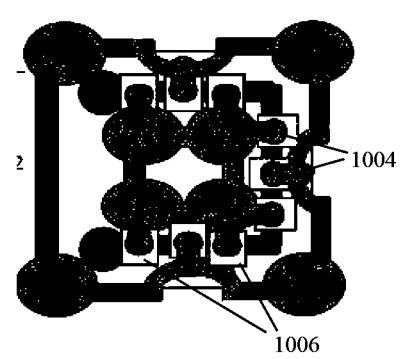
FIG. 10C presents an exemplary diagram of two recirculation loops with cellular channels connected to recirculation loops through filters.
Figure 10D:
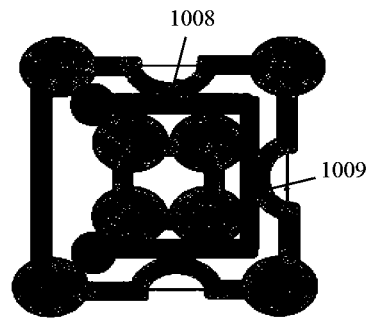
FIG. 10D presents an exemplary diagram of two overlapping recirculation loops with channels at different depths.
Figure 10E:
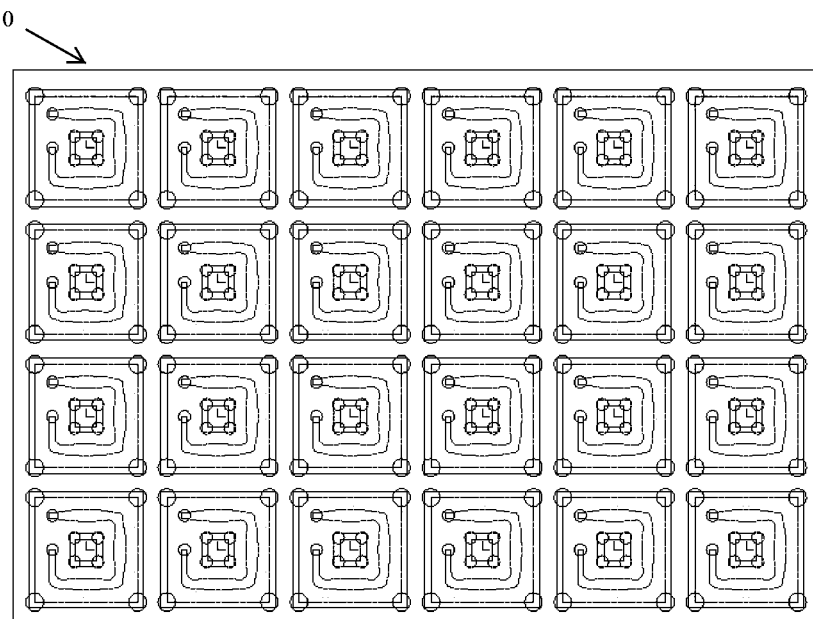
FIG. 10E presents an exemplary diagram of a 96-well plate format with a cellular channel sandwiched by two recirculation loops.

In some embodiments, a separate cell or organ channel 1003 may be included in between the recirculation channels 1001, 1002 with inlet 1003a and outlet 1003b for the delivery of cells or gel as illustrated in FIG. 10A. Both the inside and outside loops 1001, 1002 may be powered by gravity flow and may be connected to the middle cell channel 1003 by side channel fingers 1004. In some embodiments, the middle channel 1003 may be in different depths and multiple channel loops can be operated as open channels or closed channels. In FIG. 10B multiple wells 1000 with different heights or depths can be used to enhance recirculation across outer channel loops 1002. In some embodiments, the interaction between the middle channel 1003 and the outer channel loops 1002 may be accomplished by side-channels 1004 fitted with membrane filters 1006, as seen in FIG. 10C, so that cells transport may be controlled better. In most embodiments, the outer channel 1002 and the middle cell channel 1003 interactions may be enhanced by curved channels 1008, 1009 as in FIG. 10D. For example, such sandwiched recirculation loops with cell channel can be developed in 96-well format 70 as in FIG. 10E.

Figure 11A:
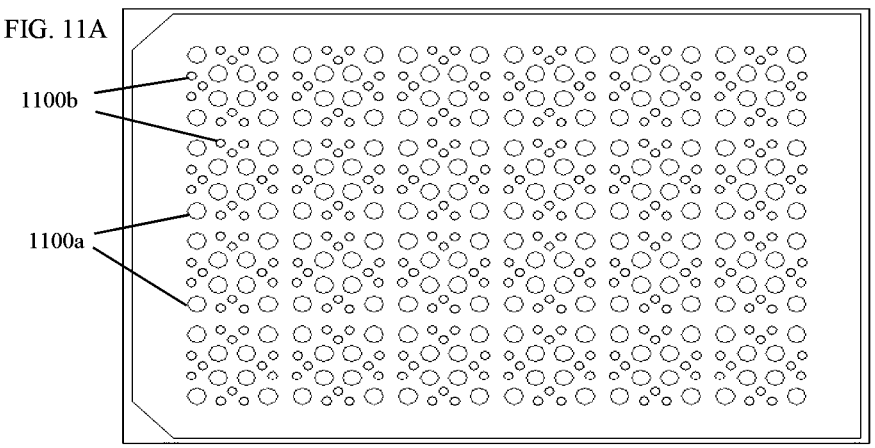
FIG. 11A presents an exemplary diagram of 96-well plate format two recirculation loops with additional holes for gas exchange within a channel through a membrane layer.
Figure 11B:
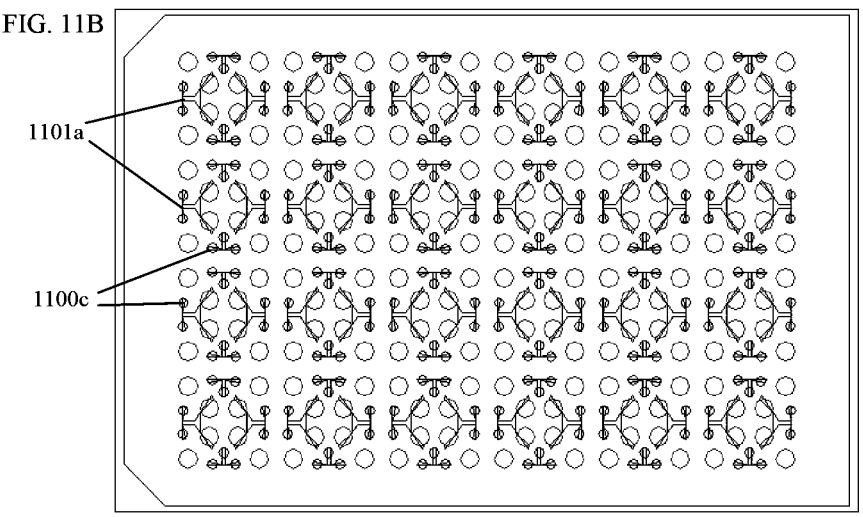
FIG. 11B presents an exemplary diagram of the 96-well plate format with additional holes for gas exchange through a top partial recirculation layer.
Figure 11C:
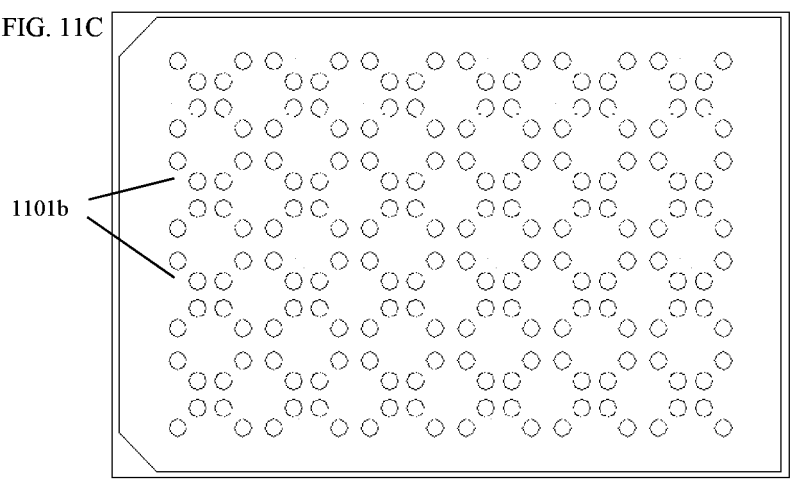
FIG. 11C presents an exemplary diagram of the 96-well plate format with a bottom partial recirculation layer.
Figure 11D:
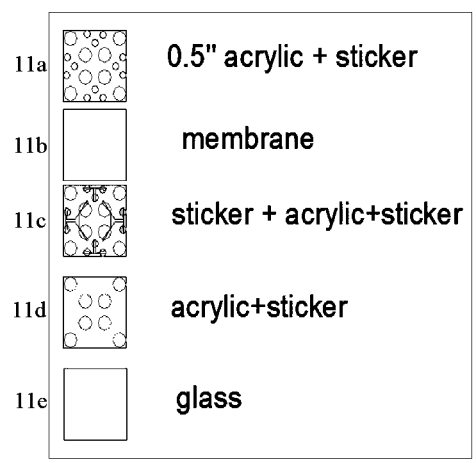
FIG. 11D presents an exemplary diagram of the 96-well plate format showing different layers.
Figure 11E:
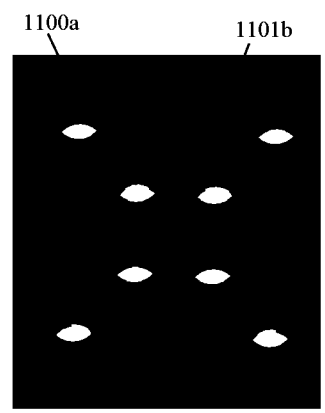
FIG. 11E presents an exemplary 3-D diagram of one of the wells of the 96-well plate format with two recirculation loops.

In most embodiments, fabrication of the two-loops of channels may use layer by layer methods. Each layer may be fabricated using two or more sets of connected bridge channels 1101, as best illustrated in FIGS. 11B-11D. In some embodiments, one or more of the polymeric layers may not offer micropores for $O_2/CO_2$ exchange for cell respiration. In order to allow such gases exchange, porous membrane layers such as silicone may be inserted in the channels, which would open the channels to a gas environment. In FIG. 11A, a layer 11a in the fabrication of the organ plate 11 with additional holes 1100a may be introduced along with an eight (8) set of holes 1100b for gravity flow. These additional holes 1100b may carry gases from the environment into cells through the porous membrane layer thereby exposing the channels to gases. In FIG. 11B, channels 1101a with additional holes 1100c may also connect the exposed channels 1101a to the gas environment. In some embodiments, In FIG. 11C, the bottom bridge channels 1101b are shown. In most embodiments, a fabricated layer-by-layer device may have multiple layers, including membrane layer 11b, are shown in FIG. 11D. In FIG. 11E, a 3-D version of the wells 1100a and channels 1101b of a single unit are shown.

Figure 12A:
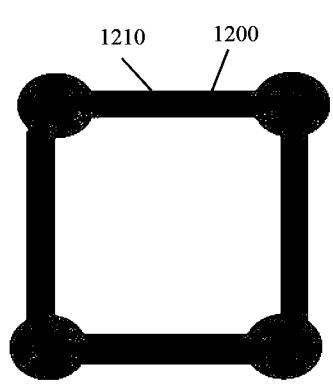
FIG. 12A presents an exemplary diagram of a channel loop inside a recirculation loop at different depths.
Figure 12B:
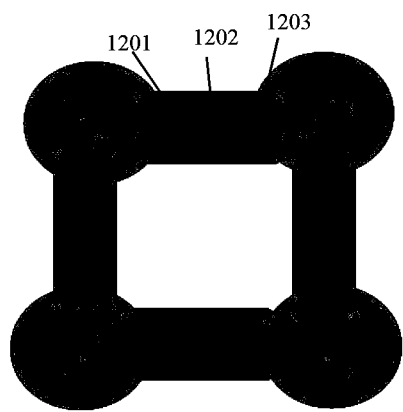
FIG. 12B presents an exemplary diagram of multiple channel loops in multiple recirculation loops at different depths.
Figure 12C:
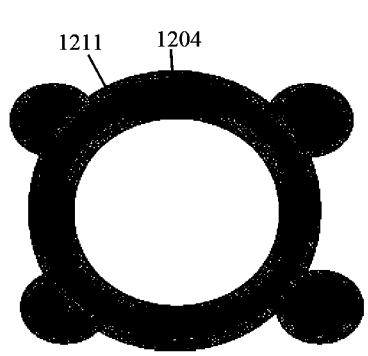
FIG. 12C presents an exemplary diagram of a circular channel loop inside a recirculation loop at different depths.
Figure 12D:
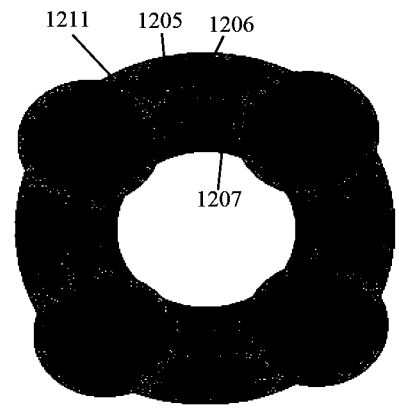
FIG. 12D presents an exemplary diagram of multiple circular channel loops in multiple circular recirculation loops at different depths.

In some embodiments, one or more channels may be develop in a main channel with multiple depths to allow gravity flow-based recirculation. In one embodiment, as shown in FIG. 12A, a single channel 1200 may be recirculated in a main channel 1210 along a square path. In another embodiment, in FIG. 12B, three channels 1201, 1202, 1202 may be recirculated in the main channel 1210 along the square path. In some embodiments, as inn FIG. 12C, a single loop recirculation channel 1204 in a circulation main channel 1211 may be made. In other embodiments, as in FIG. 12D, multiple circular recirculation channels 1205, 1206, 1207 may be developed in the main channel 1211. The one or more recirculation channels 1205, 1206, 1207 may be side by side in one layer sandwiching the main cell layer 1211.

Figure 13A:
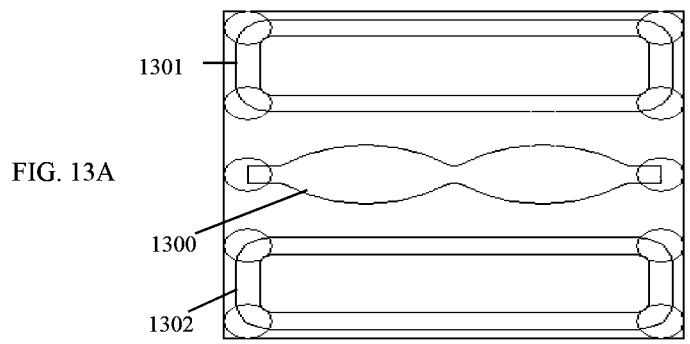
FIG. 13A presents an exemplary diagram of two circulation loops side by side connected to ellipsoidal channels by channels in different depths.
Figure 13B:
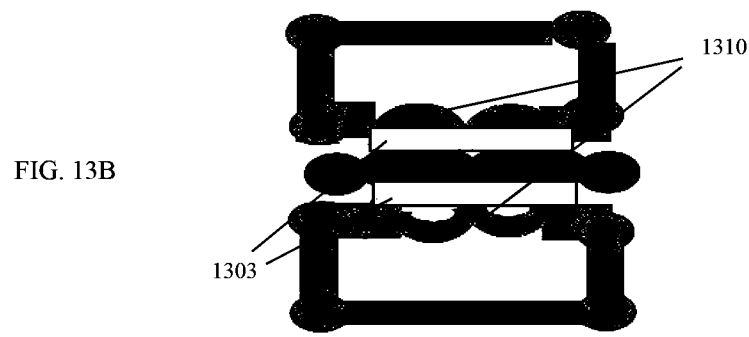
FIG. 13B presents an exemplary diagram of two circulation loops side by side connected to ellipsoidal channels by channels through filters.
Figure 13C:
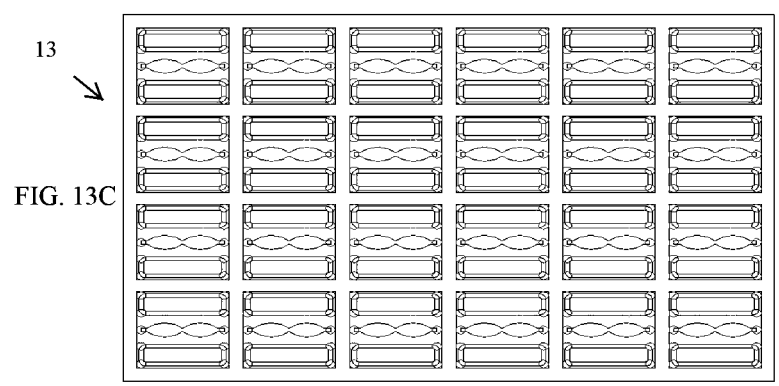
FIG. 13C presents an exemplary diagram of two circulation loops side by side connected to ellipsoidal channels in a 96 well plate format.

In some embodiments, as illustrated in FIG. 13A, a main layer for a cell may be introduced in series of connected compartments 1300 and the interaction between fluids in the top circulation channels 1301 and bottom circulation channels 1302 may be accomplished by connected side-channels 1310. In other embodiments, the interaction across recirculation loops 1301, 1302 may also be accomplished by filters 1303 in side-channels 1310, as illustrated in FIG. 13B, for better cell transportation control. In FIG. 13C such channel loops with cell channel may be developed in a standard well plate 13 such as in a 96 well format.

Figure 14A:
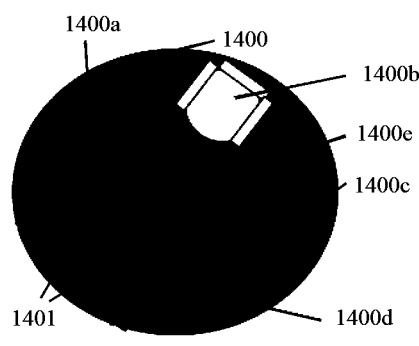
FIG. 14A presents an exemplary diagram of multiple drugs stored in connected wells in different angles and heights to release with different angular titling.
Figure 14B:
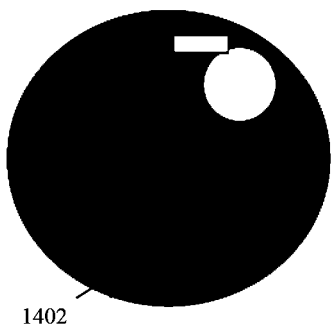
FIG. 14B presents an exemplary diagram of the multiple drugs stored in connected wells in different angles and heights to release with different angular tilting through additional angular channels.
Figure 14C:
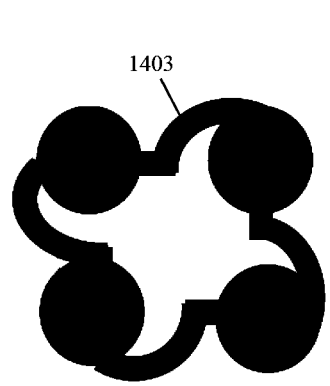
FIG. 14C presents an exemplary diagram of longer curved channels for cells within the gel connecting the wells.
Figure 14D:
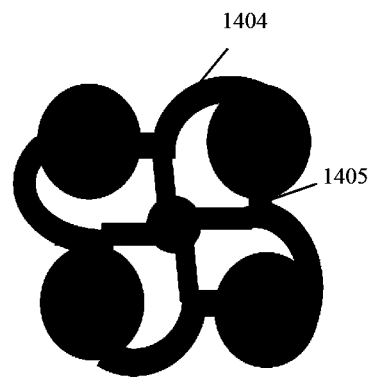
FIG. 14D presents an exemplary diagram of the channels to feed cells from a common source and form a network.
Figure 15:
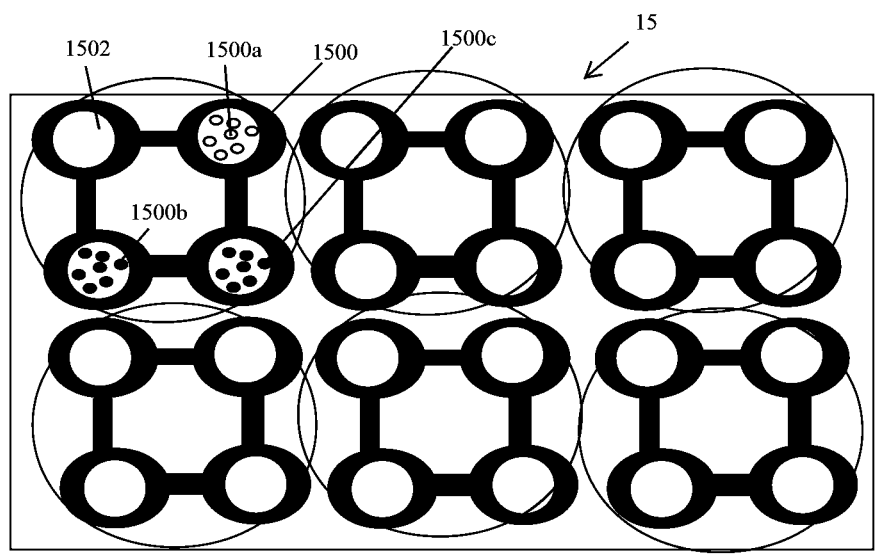
FIG. 15 presents an exemplary diagram of multiple cells on transwell filters inserted in a recirculation channel system.

In most embodiments, sequentially adding drugs or reagents to a cell culture or any biochemical reaction may be essential. In most embodiments, using a gravity tilt method may allow the user to dispense one or more reagents previously loaded in an inner sub-well of a main well 1400. In FIG. 14A, four inner sub-wells 1400a-d may be connected to a center sub-well 1400e through a small channel 1401. When the entire well 1400 may be tilted in one direction corresponding to the direction one of the inner sub-wells 1400a-d, then the fluid may be dispensed in to the main well 1400. In most embodiments, the inner sub-wells 1400a-d may be protected on all sides so that one tilt will dispense from only one of the inner sub-wells 1400a-d. In some embodiments, as illustrated in FIG. 14B, the inner sub-wells 1400a-d may be connected through another channel 1402 with an angle that may provide greater reliability in the specific well dispensing situations. In some embodiments, multiple wells may be simultaneously activated for dispensing reagents in a standard well plate format. In some embodiments, multiple wells may be connected with angular channels 1403 to extend the length and to direct the fluids within each of the multiple wells as in FIG. 14C. In another embodiment, loading reagents, gels or cells into one or more channels 1404 may be carried out from a plurality of central channels 1405 at a different depth as in FIG. 14D. In other embodiments, multiple sub-wells 1500a may be connected to one another and may be created in a main well 1500 of standard well plate 15. In some embodiments, the multiple wells 1500a, 1500b, 1500c may be cultured to interact to each other and transwell inserts 1502 from the top of the well 1500 as illustrated in FIG. 15. In some embodiments, multiple cells types, organs or vascular channels may be created in the top transwell inserts 1502 and may be allowed to interact with the cells in a bottom channels.

A standard nutating mixer may be also used for performing recirculation with standard timings and maximum tilt. Custom nutating mixer with reconfigurable tilt angle, actuation speed, pulse with, shear rate, and residence time may be made available to the user.

Pneumatic Recirculation

Figure 16B:
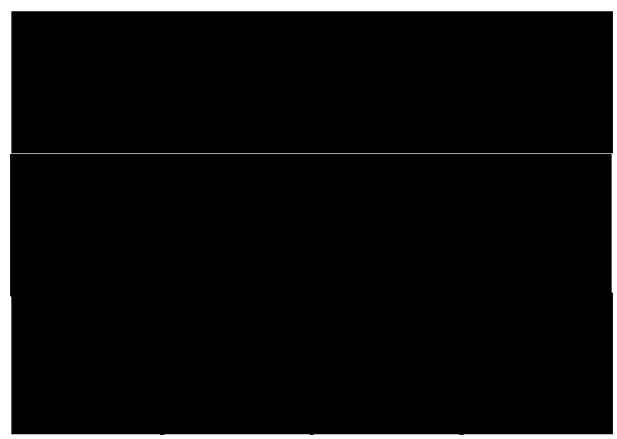
FIG. 16B presents an exemplary diagram of an array of high shear rate recirculation plate.
Figure 16A:
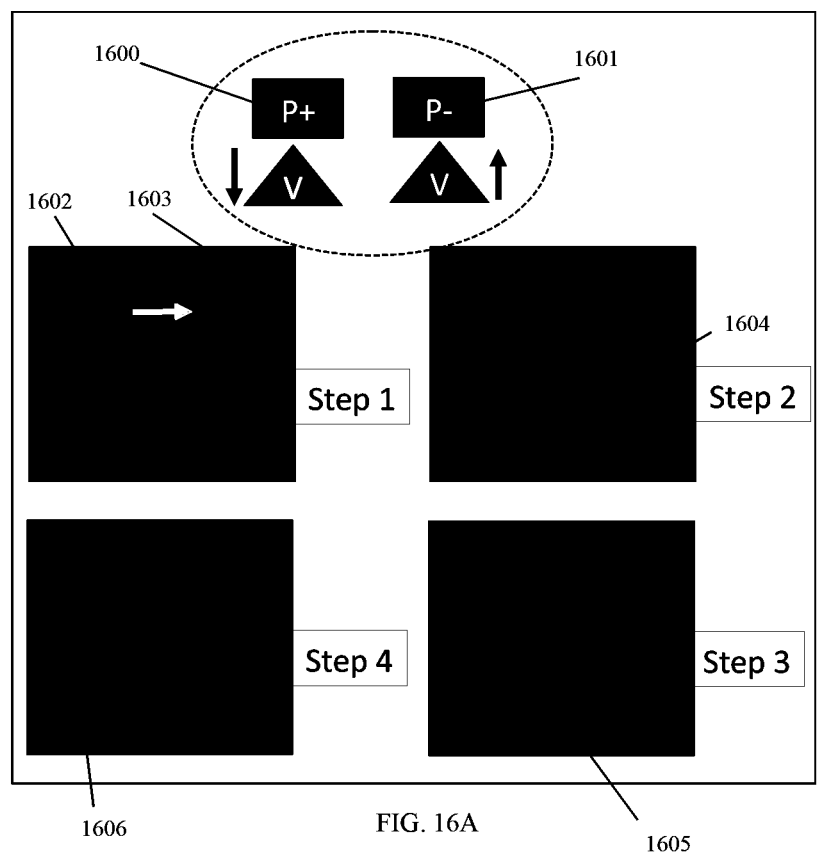
FIG. 16A presents an exemplary diagram of activating recirculation at high shear rates using four timed step actions by pressure and vacuum sources.

Apart from gravity-driven flow-based recirculation, pressure based recirculation may be performed. The basic principle may be that in order to develop a flow in a direction there should be a pressure difference between two points. In some embodiments, as seen in FIG. 16A, a user may create a pressure difference using two pumps in positive pressure 1600 and negative pressure 1601 leading to flow in one direction. By applying such pressures at different sites in a recirculation channel, a recirculation loop may be created. In FIG. 16A, in step 1, the positive pressure 1602 may be applied to a first well and the negative pressure 1603 may be applied to a second well in the direction of the array. This may lead to flow in the direction from left to right. Continuing with step 2 along with the positive and negative pressure, the flow continues in the same direction 1604. With additional steps 3, 4 the direction 1605, 1606 of the flow may continue in a clockwise direction, the recirculation will be complete. In most embodiments, the recirculation may be extended to multiple well system as illustrated in FIG. 16B.

Figure 17A:
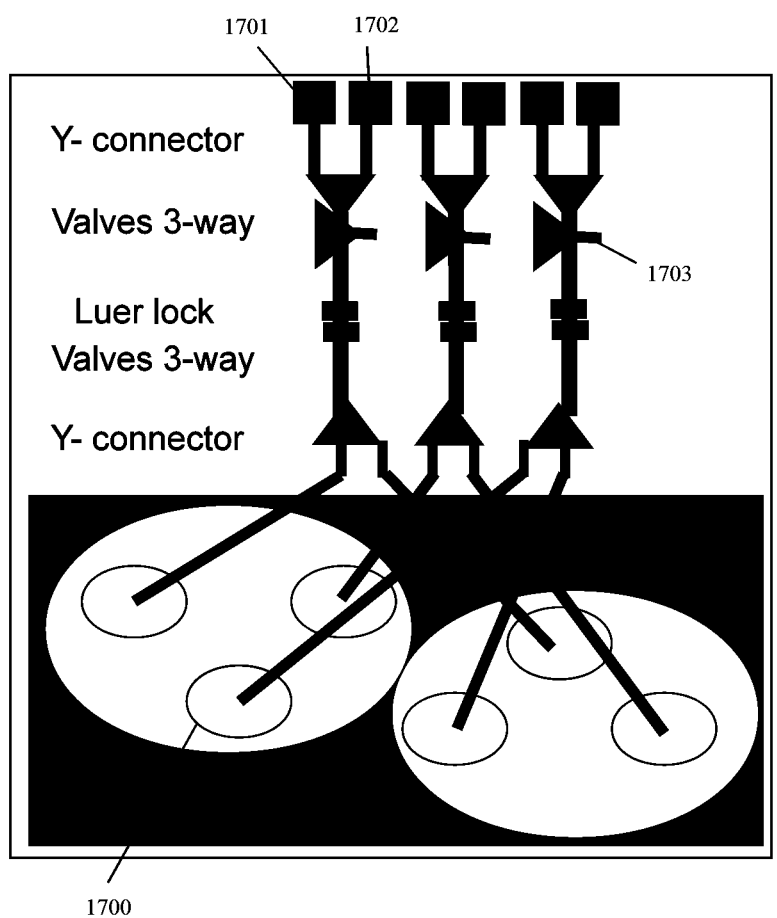
FIG. 17A presents an exemplary diagram of fluidic connections to recirculation by pressure/vacuum sources.
Figure 17B:
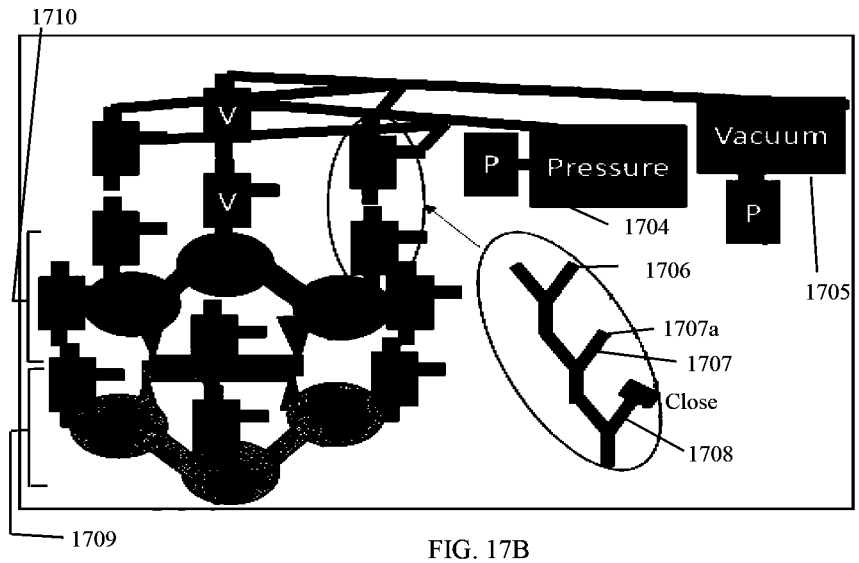
FIG. 17B presents an exemplary diagram of dual recirculation for top and bottom layer fluidics.
Figure 17C:
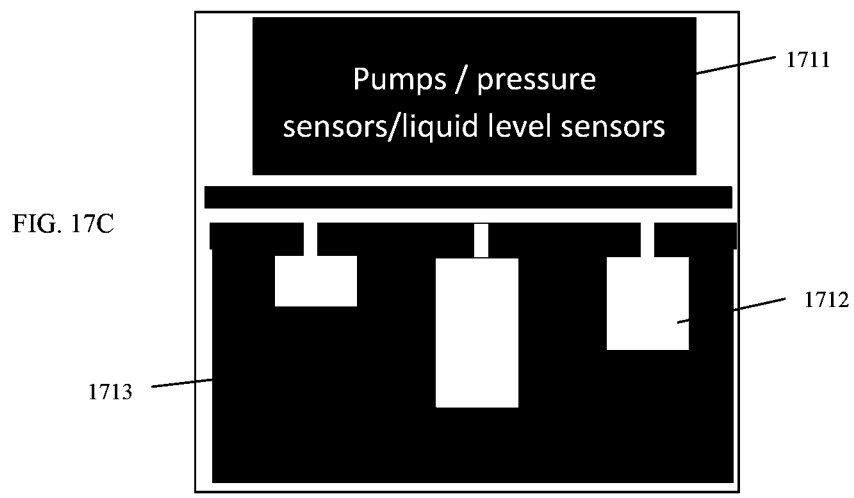
FIG. 17C presents an exemplary diagram of a side view of three wells activation by pressure/vacuum sources.

In most embodiments, the recirculation may be implemented in a minimum of 3 wells 1700 and the pressure 1701 or vacuum 1702 sources may be multiplexed as illustrated in FIG. 17A. By electrically controlling the valves 1703, vacuum or pressure pumps may be switched for different steps. While some pumps will have built-in membrane valves, in some embodiments others pumps may not have built-in membrane valves. The built-in valve may hold the liquid level in between the steps so that the pumping may be in one direction. In other embodiments, instead of pulsed flow-based pumping, pressure based pumping may be used. In this case, a positive pressure pump P and a negative pressure pump P' may be used to maintain a pressure tank 1704 and a vacuum tank 1705 as in FIG. 17B. In most embodiments, valves may be used for switching pressure or vacuum across the recirculation loops. Three set of valves (two 3-way 1706, 1707 and one 2-way 1708) as depicted in FIG. 17B may be cascaded to connect the pressure or vacuum tanks 1704, 1705 and to vent, using a vent 1707a, during a waiting period. In some embodiments, the waiting period for venting may be required to keep the liquid level in the wells below a safety level. The waiting period may avoid any abnormal pumping due to the mismatch of channel resistance in the recirculation path. Such a system may be used for multiple recirculation loops 1709, 1710. In most embodiments, the continuous recirculation may be monitored using liquid level sensors or pressure sensors 1711 in each well as shown in FIG. 17C. The air pressure 1712 in each well may pump up and down in a cyclic manner to perform recirculation of a liquid 1713.

Figure 18:
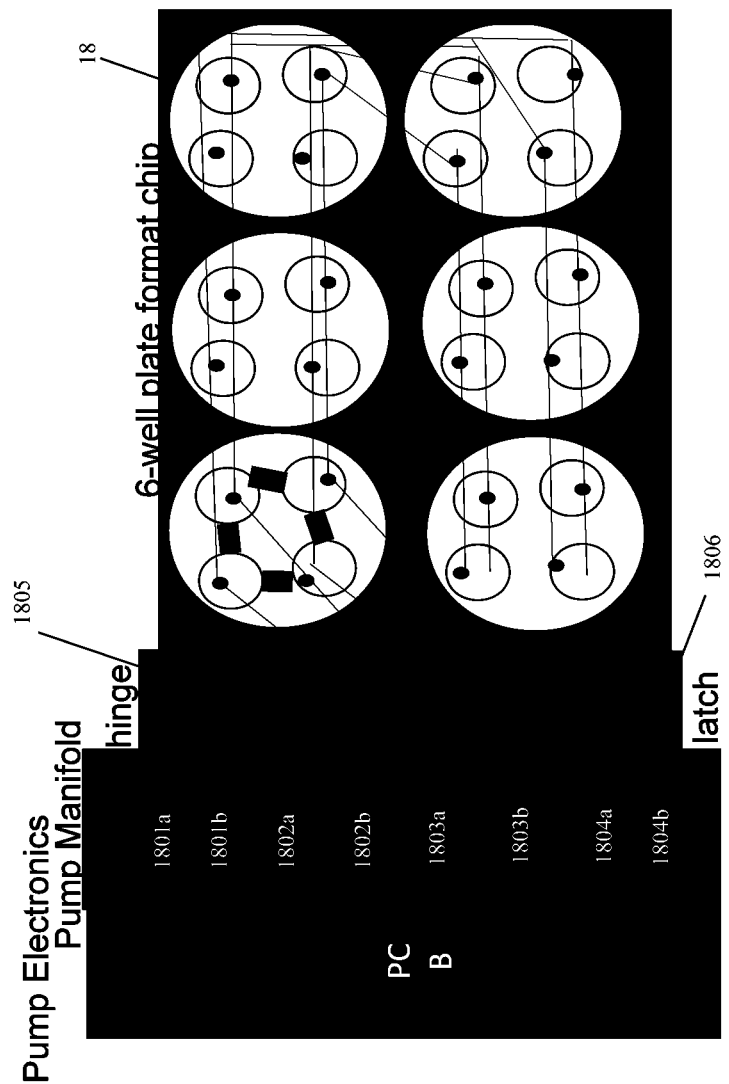
FIG. 18 presents an exemplary diagram of a manifold driving 6-well plate format high shear chip.
Figure 19:
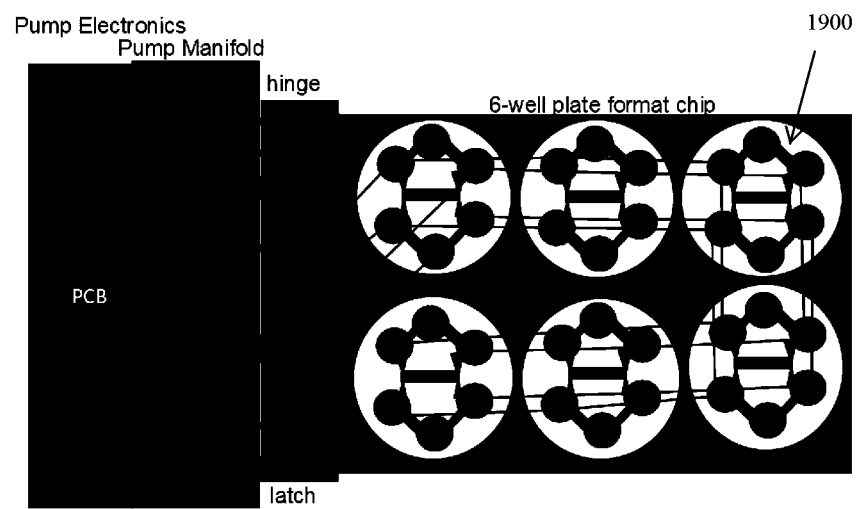
FIG. 19 presents an exemplary diagram of a two-loop high shear flow recirculation system.
Figure 20A:
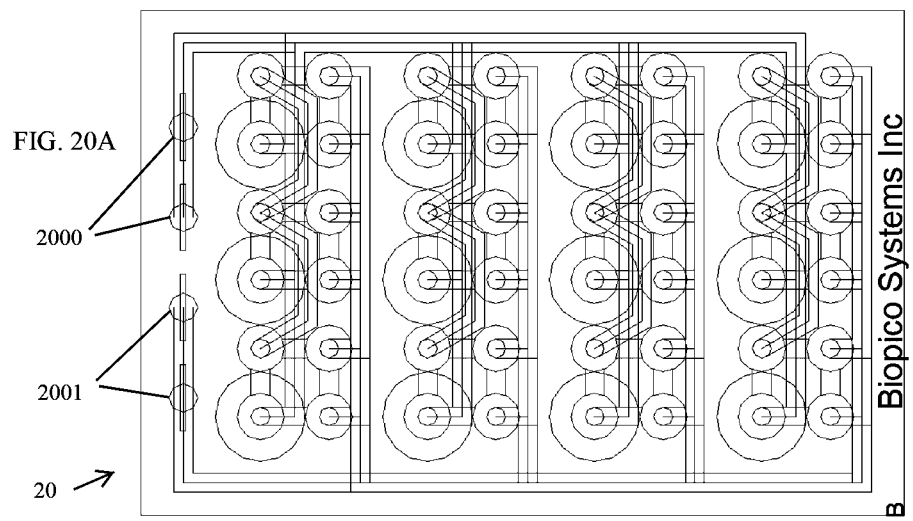
FIG. 20A presents an exemplary diagram of a three well set of 24 shear loops operated by three sets of vacuum and pressure sources connected to three inputs.
Figure 20B:
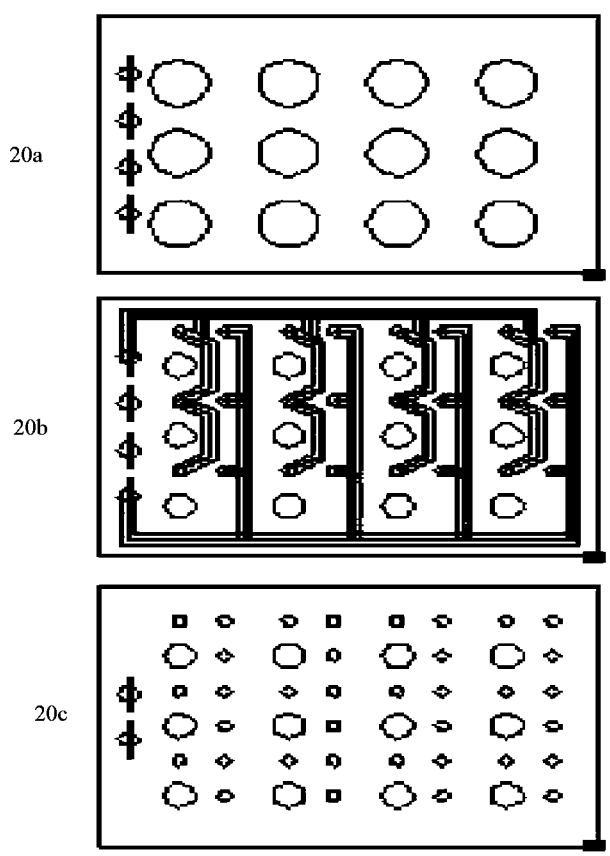
FIG. 20B presents an exemplary diagram of different fluidic layers of the three well set of 24 shear loops.

In most embodiments, the pneumatic controlled recirculation system may be extended to multiple wells of standard well plates 18 as illustrated in FIG. 18. Each pumping system derives pressure or vacuum from the same set of sources 1801a-b to 1804a-b. In most embodiments, an interface of the pumping system to well-plates may be accomplished using a manifold 1805 through hinge and latch mechanism 1806. In some embodiments, as seen in FIG. 19, the pneumatic recirculation system may be extended to two layer recirculation fluidics 1900. The organ system with a separate cell channel and sandwiched recirculation channels may be also powered by pneumatic control. Each organ system may be connected to common pressure and vacuum sources. In the case of three well organ system, pressure or vacuum sources may be applied at three locations and the gas flow may be routed to different locations through channels in different layers of organ chip. In some embodiments, where four connected-organs systems may be used, pressure/vacuum sources 2000, 2001 may be connected to one edge of the chip as in FIG. 20A. In such embodiments, when fabricating the chip 20, multiple layers 20a, 20b, 20c may be bonded together as displayed in FIG. 20B.

Shear Flow Stimulation

Figure 21A:
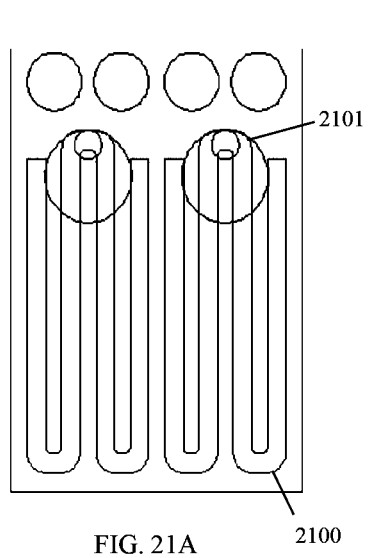
FIG. 21A presents an exemplary diagram of two shear flow circuits with channels where cells are seeded.
Figure 21B:
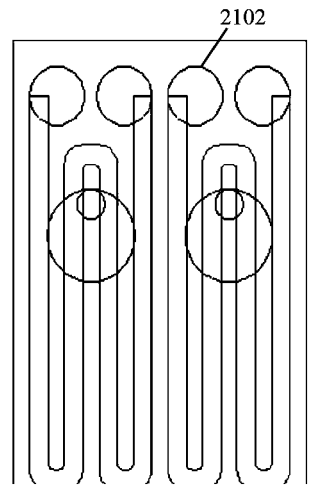
FIG. 21B presents an exemplary diagram of the two shear flow circuit channels for fluidic flow to cause shear flow.
Figure 21C:
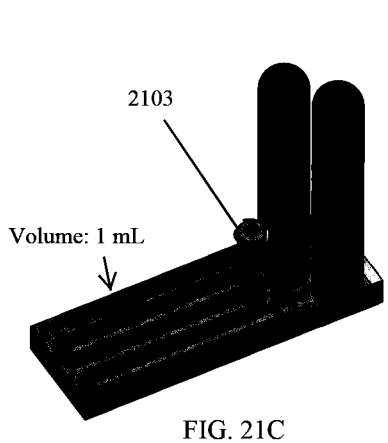
FIG. 21C presents an exemplary 3-D diagram of a shear chip showing a first step of delivering cells.
Figure 21D:
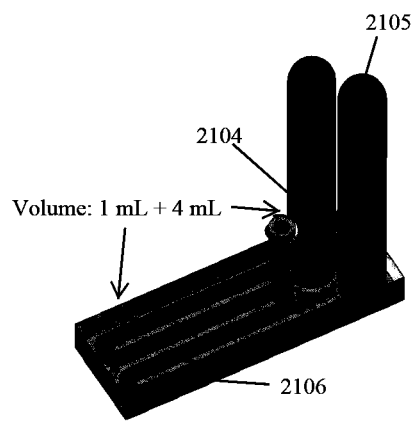
FIG. 21D presents an exemplary 3-D diagram of the shear chip showing a second step of introducing media to apply shear flow to the cells.
Figure 22A:
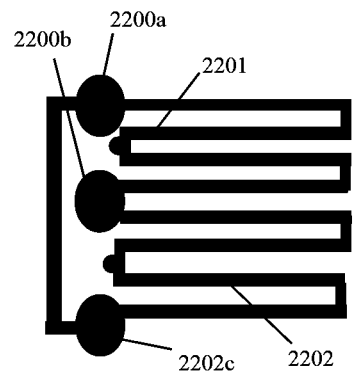
FIG. 22A presents an exemplary diagram of unidirectional recirculation using high shear flow in a two-loop shear chip.
Figure 22C:
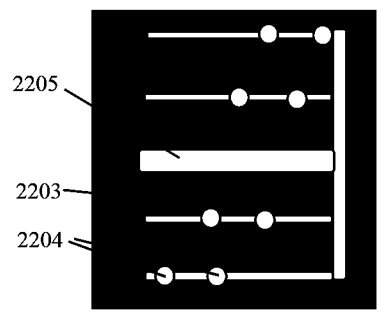
FIG. 22C presents an exemplary diagram of unidirectional forced flow and gravity flow in the opposite direction, directed towards a separate channel.
Figure 22E:
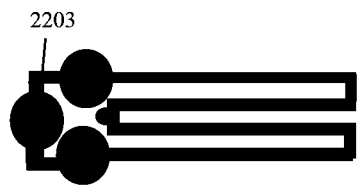
FIG. 22E presents an exemplary diagram of unidirectional flow in a loop.
Figure 22D:
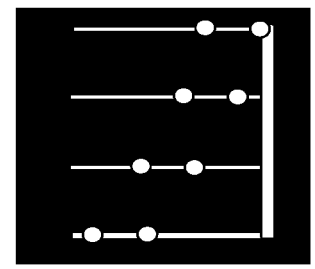
FIG. 22D presents an exemplary diagram of unidirectional forced flow and gravity flow in the opposite direction, directed towards a other channels.
Figure 22E:
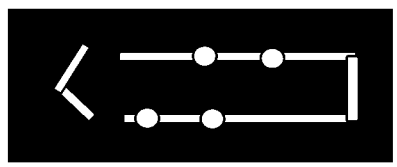
Figure 22F:
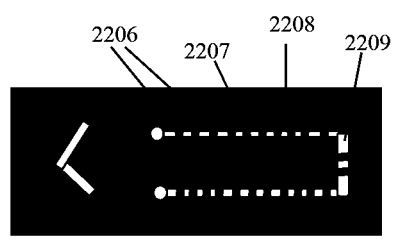
FIG. 22F presents an exemplary diagram of unidirectional flow in a loop of an array device.

In some embodiments, shear flow may be essential for cellular systems for their growth and function. In these embodiments, cells may be grown in a serpentine channel 2100, as depicted in FIG. 21A, to apply a constant shear flow. Cells may be delivered into a middle section 2101 of the serpentine channel 2100, which may allow the cells to spread uniformly across the channel 2100. Flow may be applied by connecting the cell layer to reservoirs 2102 through a channel at different depths as in FIG. 21B. In some embodiments, as seen in FIG. 21C, the cells may be loaded through a luer port 2103. In other embodiments, as in FIG. 21D, media 2104 for shear flow stimulation may be delivered through the luer port after the cells adhere on to a bottom surface of a channel 2106. In some embodiments, a shear flow stimulation may be applied using pressure pulses at a top of the tube 2105 through a 0.2 um luer filter. The system may be stimulated with saw-tooth pressure pulses using a single pump for forwarding flow and gravity for reverse flow, or bidirectional flow using two pumps. In some embodiments, to provide gas exchange from the cell channel 2106, a membrane such as silicone or PDMS layer may be added on the top of the cell channel 2106 and a top cover with an open channel may be used to facilitate the gas exchange In some embodiments, unidirectional flow shear stimulation may be achieved by three wells 2200a, 2100b, 2200c and may have cell channels 2201, 2202 in between the wells 2200a, 2100b, 2200c as in FIG. 22A. In some embodiments, pneumatic unidirectional pressure pulses may be set. In other embodiments, the unidirectional flow may also set with one cell culture channel 2203 in between two wells as illustrated in FIG. 22B. Stimulating organoids using shear flow may be accomplished by trapping organoids from the cell culture channel 2203 across two filters 2204 in the channel as shown in FIG. 22C with multiple parallel organoid trapping sites. In most embodiments, a pulse flow may be set at each well serially or all the wells simultaneously and the fluid disturbance may be borne by other channels especially in a fat channel 2205. The stimulation may also be applied without the fat channel 2205 as in FIG. 22D. Unidirectional shear flow may be applied to organoids as in FIG. 22E. In some embodiments, unidirectional flow may be may also be applied to side-channels 2206 from two parallel channels 2207, 2208. A middle channel 2209 may be filled with cells or cell in gel for forming a vascular network. In other embodiments, unidirectional shear flow may be applied from a media or reagent vial to cell channels using a peristaltic pump. In most embodiments, ethanol may be used to sterilize the peristaltic pump tubing, the solution may be taken in the vial and the chip may be by-passed with a connector tubing. In other embodiments, ozone gas may also be used for sterilization by connecting the tubing to an ozone generator.

Figure 23A:
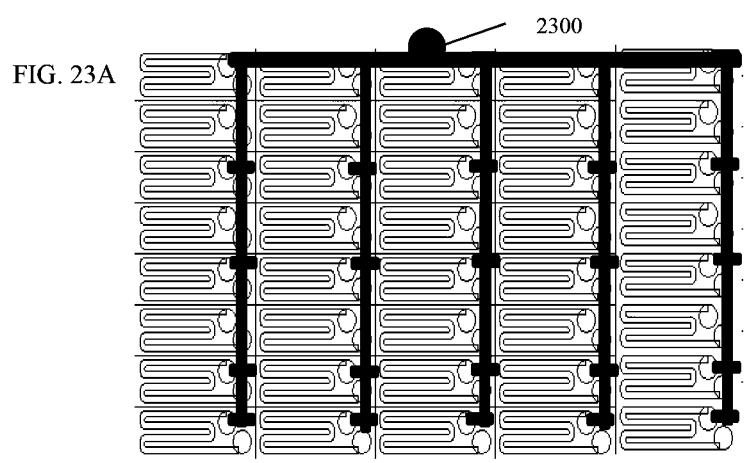
FIG. 23A presents an exemplary diagram of shear flow applied to an array of channels using pushing air pulses.
Figure 23B:
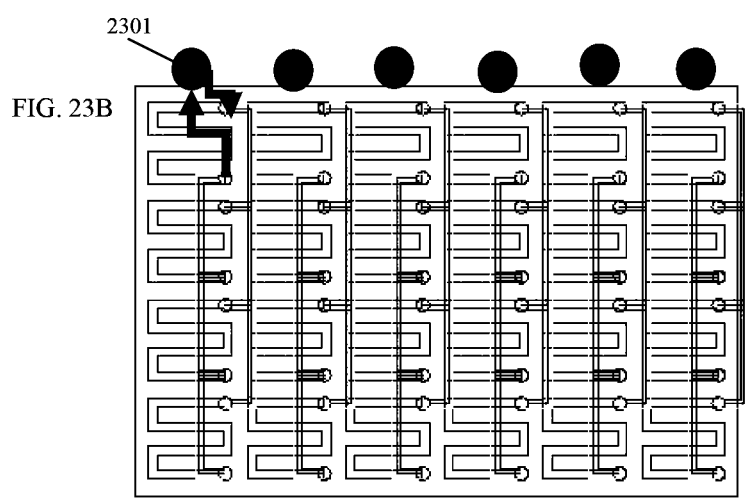
FIG. 23B presents an exemplary diagram of shear flow applied to an array of channels using a multi-channel peristaltic pump.

In some embodiments, stimulation of shear flow on an array of devices 23 may be connected together to one or more sources in the case of flow from pushing the air column from the tube 2300 as in FIG. 23A. In other embodiments, for stimulating cells with a steady shear flow rate a multi-channel peristaltic pumps may be used. As illustrated in FIG. 22B, 4-channels may be connected together and a 6-channel peristaltic pump 2301 may be used.

Figure 24A:
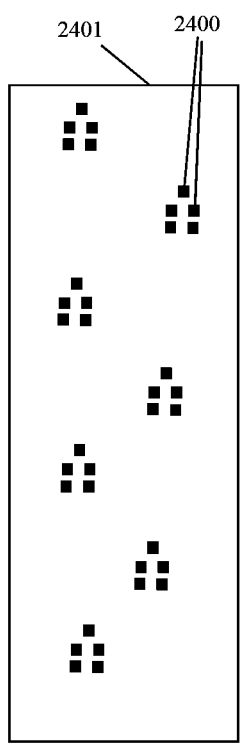
FIG. 24A presents an exemplary diagram of trapping sites for organoids or cells in the direction of flow.
Figure 24B:
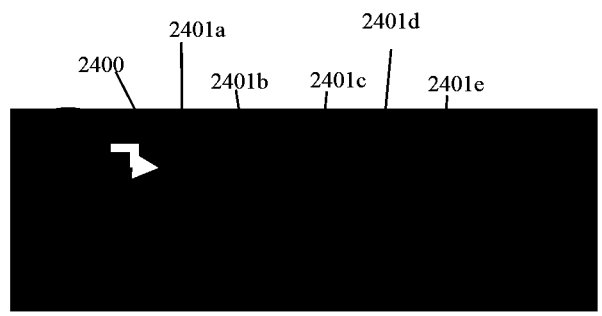
FIG. 24B presents an exemplary diagram of parallel cell traps.
Figure 24C:
FIG. 24C presents an exemplary diagram of parallel traps with different shear flows.
Figure 25A:
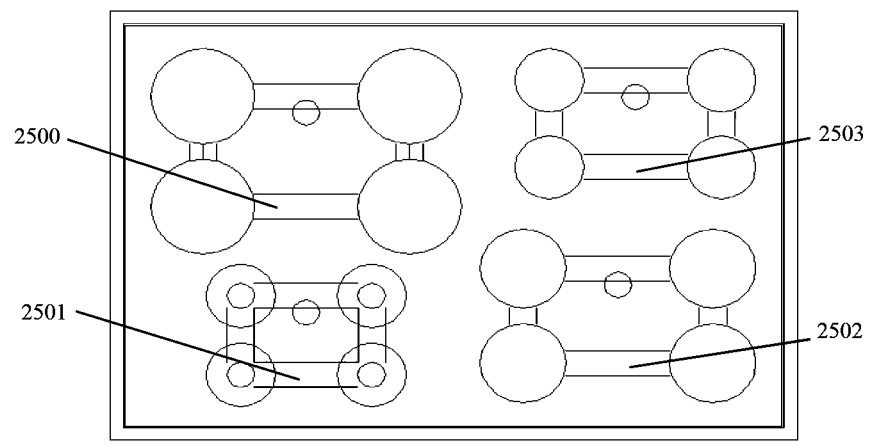
FIG. 25A presents an exemplary diagram of geometry controlled multiple shear rates.
Figure 25B:
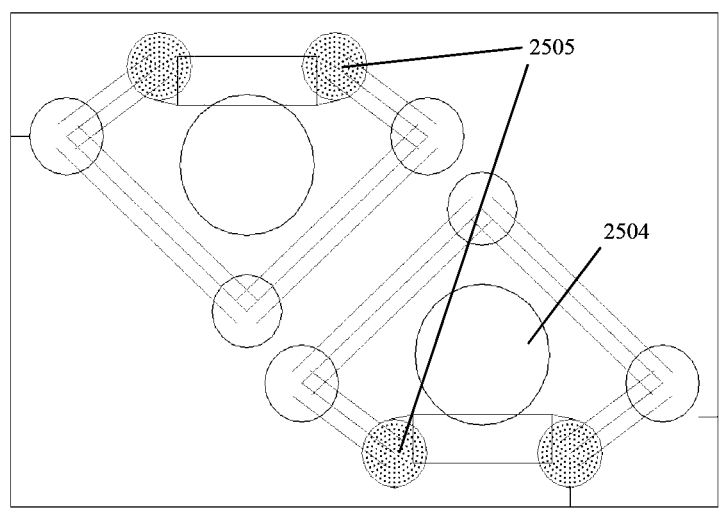
FIG. 25B presents an exemplary diagram of organoids with filters on either side of flow and organoids are dropped from a side of the flow channel.
Figure 25C:
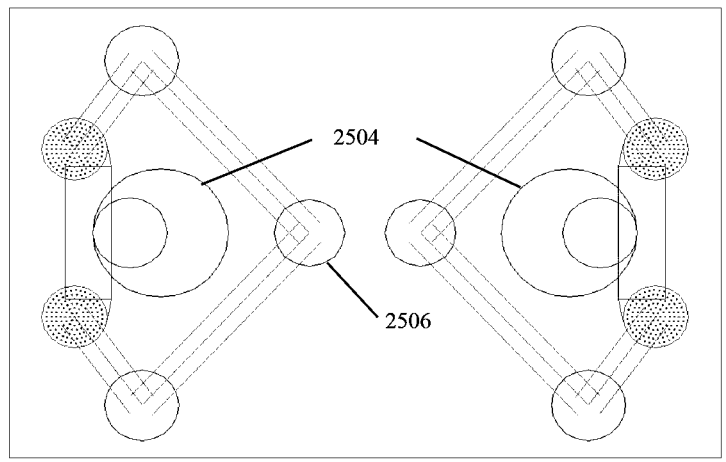
FIG. 25C presents an exemplary diagram of organoids with filters on either side of flow and options for perfusion.
Figure 25D:
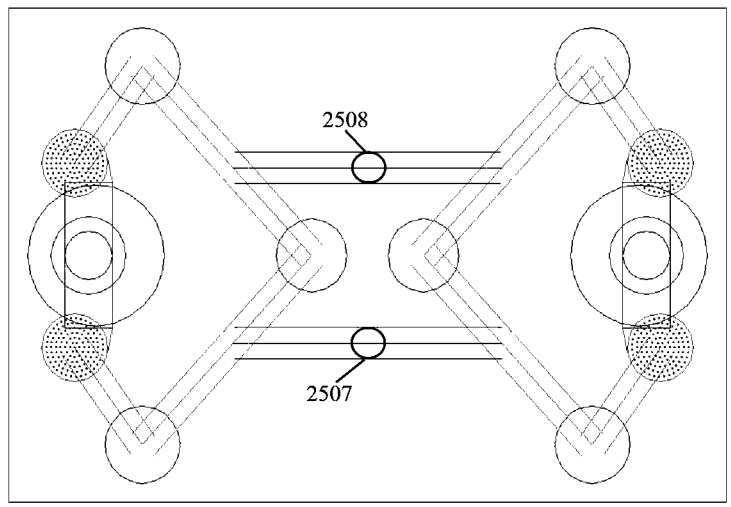
FIG. 25D presents an exemplary diagram of organoids with filters on either side of flow where organoids are dropped in the middle of the channel.

In some embodiments, single organoids or single cells may be trapped on trapping sites and flow shear stimulation may be applied. In FIG. 24A, trapping sites 2400 with five (5) pillars may be in a main channel 2400. In most embodiments, trapped single cells may be stimulated and single cell RT PCR may be performed in the trapping sites 2400. In some embodiments, the multiple trapping sites 2400 may be placed in multiple branch channels 2401a-e as shown in FIG. 24B. In other embodiments, multiple shear flow rates may be applied to different branched channels 2402, 2403, 2404, 2405 as depicted in FIG. 24C to study shear spectrum on gene expression. In another embodiment, multiple shear flow rates may also be studied using recirculation channels 2500, 2501, 2502, 2503 with different channel dimensions as illustrated in FIG. 25A. In some embodiments, organoids 2504 may be stimulated using shear flow rate within recirculation channels placed in between two filters 2505 as in FIG. 25B. In one embodiment, the organoids 2504 may be stimulated by a same source of pressure and vacuum 2506 as seen in FIG. 25C. In another embodiment, automated perfusion of media periodically may be delivered to the organoids through an extra channel inlet 2507 and outlet 2508 as shown in FIG. 25D.

In some embodiments, constant unidirectional flow of media from a bottle 2600 may be applied, which may be made as a periodic bidirectional shear flow rate as in FIG. 26A. In another embodiment, multiple shear flow stimulations may be applied in parallel channels 2601 for a multiplexed study as depicted in FIG. 26B. In most embodiments, to fabricate a filter 2602 for trapping organoids, a multiple layer configuration may be developed as structured in FIG. 26C. In another embodiment, instead of delivering media for stimulation from a bottle, serpentine channels 2603 in a chip may be developed and pumps may be connected to the serpentine channels 2603 to move the flow across trapped organoid as in FIG. 26D. In most embodiments, to avoid any background fluorescence effects, the chips may be made of glass, polystyrene or Cyclic Olefin Copolymer (COC). In some embodiments, Non-fluorescent stickers and adhesives may be used for the fabrication of the chips. USP IV materials may be chosen to avoid toxicity effects when fabricating the chips.

Figure 27A:
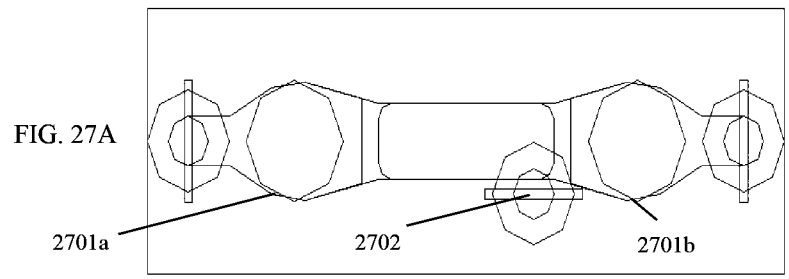
FIG. 27A presents an exemplary diagram of a perfusion fluidics chip with a cross sectional view.
Figure 27B:
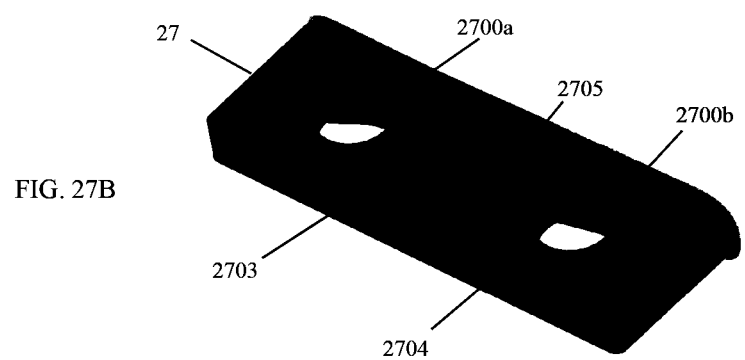
FIG. 27B presents an exemplary 3D diagram of the perfusion fluidics chip showing a cell loading inlet, media inlet/outlet luer lock connector holes, air traps/gravity flow tube holes and cells reservoirs.
Figure 27C:
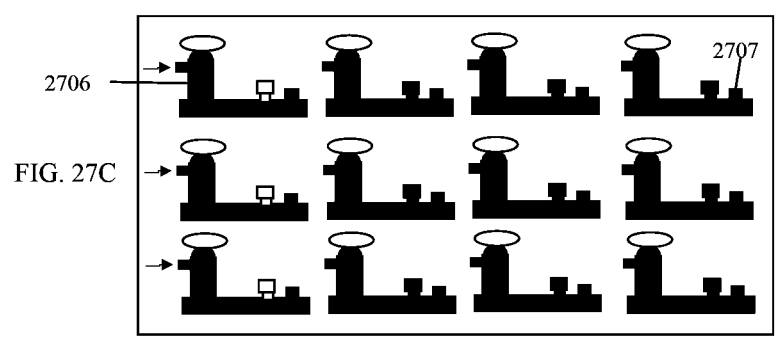
FIG. 27C presents an exemplary diagram of the perfusion fluidics chip with air traps and antisiphon effect to discretize the flow.

Now referring to another embodiment, a perfusion chip 27 with a cylindrical tube inlet 2701a and a cylindrical tube outlet 2701b and a cell inlet 2702 that may enable gravity-driven flow between each perfusion pulse as shown in FIG. 27A. A 3-D view of a chip with a luer inlet and outlet 2701a, 2701b for media and sample inlet 2702 with tall tubes for gravity flow as shown in FIG. 27B. A cross-sectional view of the chip 27 with separations 2703, 2704 of each inner cell well 2700a, 2700b as shown in FIG. 27B. In some embodiments, the cell samples may be delivered into a middle reservoirs 2705, which may be isolated from the rest of the channel so that the cells may be constrained to be in the middle reservoir. In some embodiments, an array of devices with bubble traps 2706 and a sample or media delivery and outlets 2707 is shown in FIG. 27C.

Figure 28A:
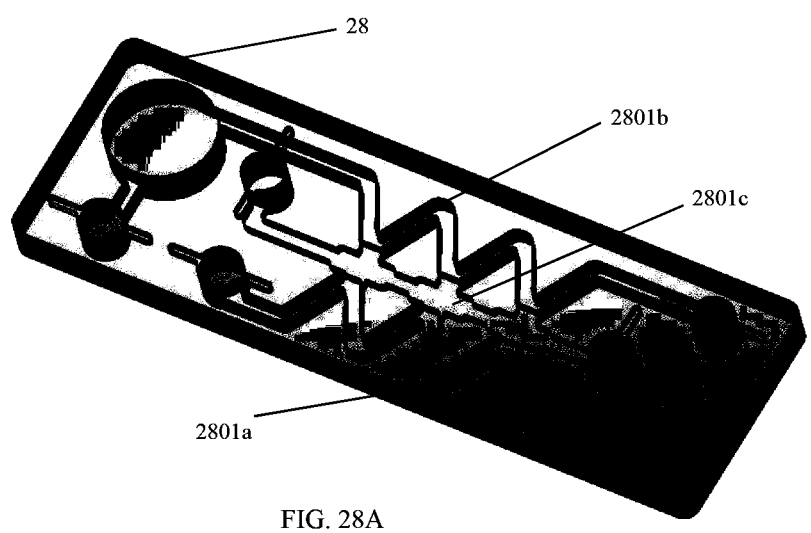
FIG. 28A presents an exemplary 3D diagram of two-sided perfusion fluidics for a vascular chip.
Figure 28B:
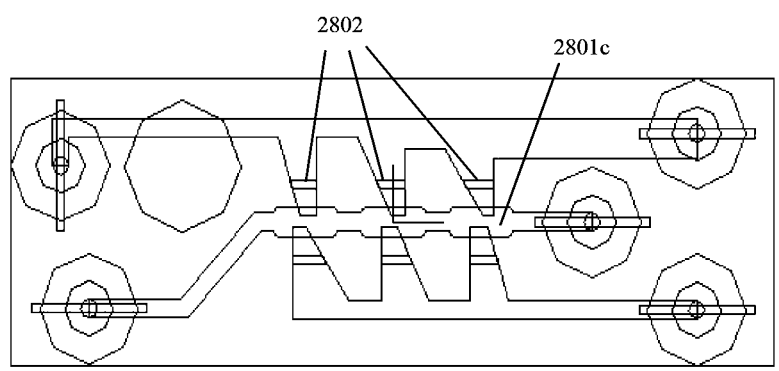
FIG. 28B presents an exemplary diagram of the vascular fluidics chip with a cross-sectional view.
Figure 28C:
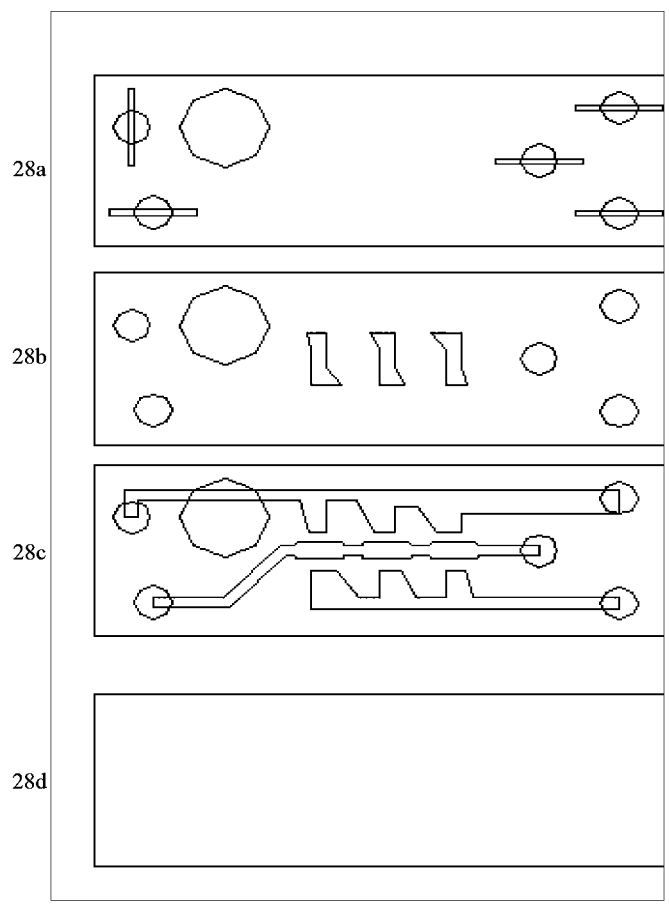
FIG. 28C presents an exemplary diagram of the vascular fluidics chip showing multiple layers of the chip.

A vascular chip 28 with media perfusion in one or more channels 2801a, 2801b on either side as illustrated FIG. 28A. The side-channels 2801a, 2801b at the bottom may have a separation distance so that the cells may be constrained in an inner main channel 2801c isolating the side-channels 2801a, 2801b. In some embodiments, a top portion of the side-channels 2801a, 2801b may be connected so that media perfusion may be facilitated into the main channel 2801c. The top portion 2802 of the side-channels 2801b may feed into the main cell channel 2801c as seen in FIG. 28B. Multiple layers 28a-d for the fabrication of the chip 28 are shown in FIG. 28C. In some embodiments, an angle of side channel fingers, directional flow of media and typical flow rates may be optimized for homogeneous flow of media across the side-channels. In some embodiments, in order to bond the layers, the user may use adhesives, ultrasonic welding or heat bonding.

Multiple concentrations generation in a programmable manner may be important for toxicity studies. One channel for drug and another channel for buffer or reagents may have separate inlets. In most embodiments, a drug profile may be programmed before entering into a cell compartment. In FIG. 29A, two inlet devices 2900 are shown. For example, media and a drug enter a mixing compartment and a mixture enters into a cell reservoir 2901. In FIG. 29B, different layers 29a-d for fabrication of the chip 29 are shown. As described in FIG. 29C, the operational steps of the drug concentration chip are shown. Step 1, initially, the cells may be delivered into the channel reservoir 2901 and may be incubated. Step 2, when the user is ready to perform drug experiments, the cells in media may be washed with a buffer for fluorescent measurement. Step 3, a concentration of drugs ranging from 0% to 100% may be prepared with the buffer that may flow into the cells compartment. Step 4, the cells may be exposed for a certain amount of time before washing the cells for the fluorescent measurements. Step 5, finally, the cells may be washed in cell media.

Figure 30A:
FIG. 30A presents an exemplary photograph of two inlets multiple concentration generator fluidic chip.
Figure 30B:
FIG. 30B presents an exemplary 3D diagram of instrumentation and manifold for the two inlets multiple concentration generator fluidic chip.
Figure 30C:
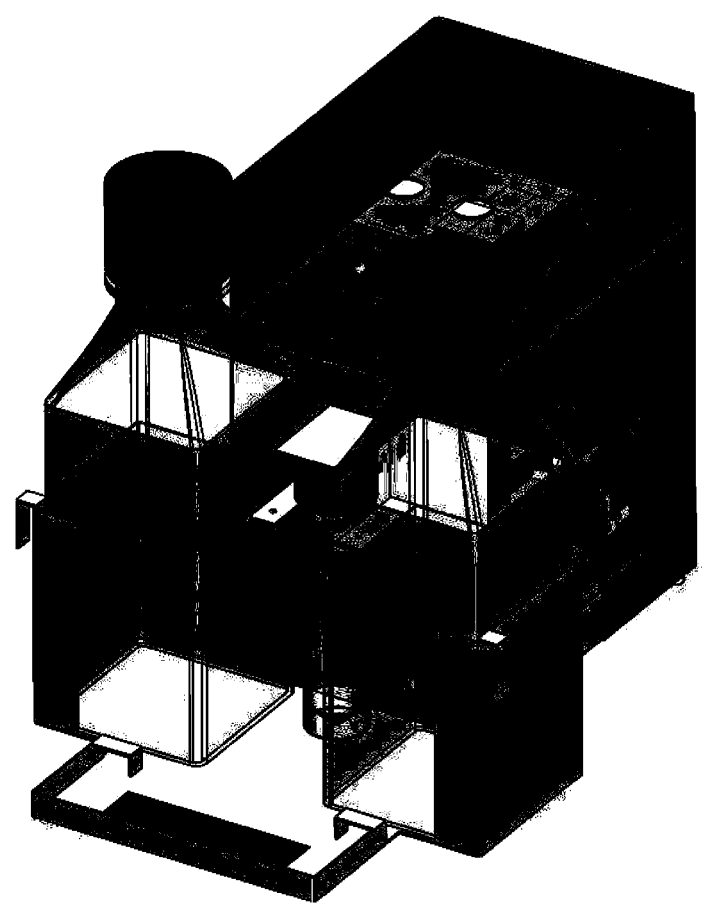
FIG. 30C presents an exemplary photograph of a handheld multiple concentration generator system.
Figure 30D:
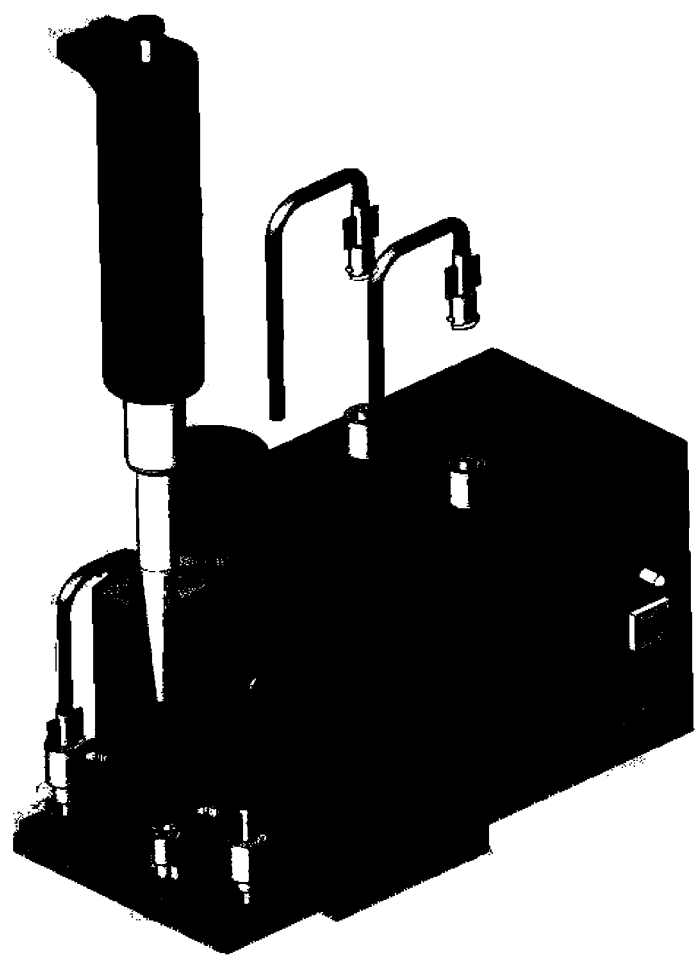
FIG. 30D presents an exemplary 3D diagram of instrumentation and manifold with a plugin for pumps.

In FIG. 30A, a photograph of the experiment with inlets, a cell reservoir and a luer lock cell inlet are shown. In FIG. 30B, the system for chip holder, media, drug and waste bottle holder are shown. In most embodiments, the entire system may be operated by a battery and may be portable or handheld as shown in FIG. 30C. In some embodiments, the chip and reagents may be connected to a pump box using a luer lock interface as in FIG. 30D.

In some embodiments, field potential signals from neural or cardiac cells may be measured for drug pharmacological or toxicity studies as seen in FIG. 31A. The chip will have an electrode array 3100 and may be connected to measurement circuits using spring loaded connectors 3101. In FIG. 31B, a fluidic interface 3102 to the chip is shown. The system may be portable and provide simultaneous optical and electrical measurements 3103. In most embodiments, a chip 31 may be set up to perform long term microscopic imaging with a hypoxia or gas controlled environment and a temperature controlled environment. As depicted in FIG. 31C, the chip 31 and system with a separate cell sample inlet 3104, a gas inlet 3105a, a gas outlet 3105b, a media inlet 3106a and media outlet 3106b. In most embodiments, the temperature may be controlled by controlling the flow of the media during recirculation. In some embodiments, a peristaltic pump may be used for recirculation of media during imaging.

Fluidic Flask array

Figure 32A:
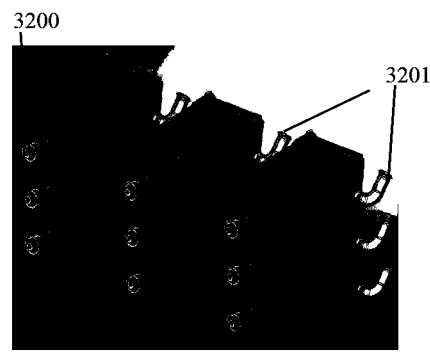
FIG. 32A presents an exemplary diagram of an array of T-flasks with inlets and outlets for media exchange.
Figure 32B:
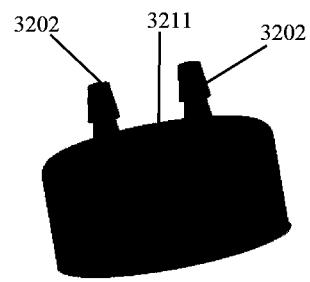
FIG. 32B presents an exemplary diagram of a cap with filter and barb connectors for tubing outside a T-flask.
Figure 32D:
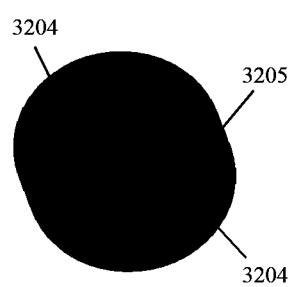
FIG. 32D presents an exemplary diagram of a cap with holes and a luer lock for connecting tubing to a T-flask or filters for gas exchange.
Figure 32C:
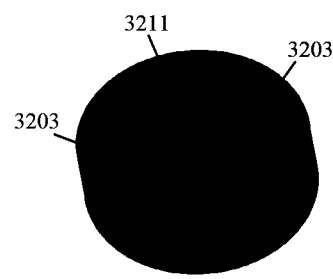
FIG. 32C presents an exemplary diagram of a cap with filter and barb connectors for tubing inside a T-flask.
Figure 32E:
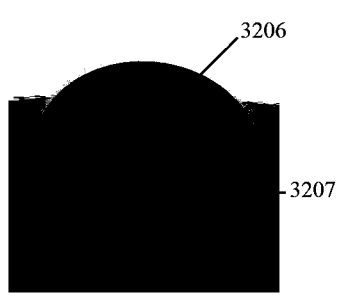
FIG. 32E presents an exemplary diagram of a funnel-shaped cap with a large filter to promote media exchange and tubing holes to connect to a T-flask.

An array of cell culture flasks may be fluidically connected for media exchange or media supplement as in FIG. 32A. Each cell culture flasks may be equipped with gas inlet connectors and media inlets 3200 and outlets 3201. The inlet and outlet ports of the flask may bend at one or more angles for avoiding any inconsistent bending in the connected tubing. In order to connect the T-flasks to media or waste fluidics, the caps may be modified with outside barb connectors 3202 (see FIG. 32B) and inside barb connectors 3203 (see FIG. 32C). In most embodiments, the barb connectors may be fabricated via injection molding and ultrasonic welding. However, the tubing (not shown) may be passed through holes 3204 in the T-flask caps and may be glued at the holes 3204 on the caps as shown in FIG. 32D and FIG. 32E. In some embodiments, filters 3211 in the caps may be important for gas exchange in normal or hypoxia conditions for cell culture. In other embodiments, an external filter 3205 as seen in FIG. 32D or an integrated filter with funnel type cap 3207 (see FIG. 32E) may be used for gas exchange during the culturing of the cells.

Figure 32F:
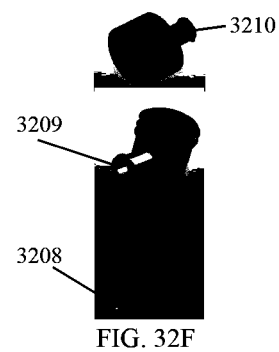
FIG. 32F presents an exemplary diagram of a vial with a luer lock for sample loading and a second luer lock for sample dispensing and cap with a third luer lock filter for gas exchange or pressure flow.

In most embodiments, media exchange may be carried out from a media vial as seen in FIG. 32F. Such media vial may have multiple luer lock ports for a media inlet or outlet 3208 and a gas inlet or outlet 3209 to push media out. Gas or air may be sent through a sterile 0.2 um filter into the vial force the media towards the outlet 3208. In most embodiments, media may be delivered into the vial via a luer port 3210. In some embodiments, media may be punched into silicone rubber cap, such as heparin cap, into the media vial using a syringe needle for closed system operations. In another embodiment, the media may be delivered through a luer lock syringe for semi-closed system operations.

Figure 33A:
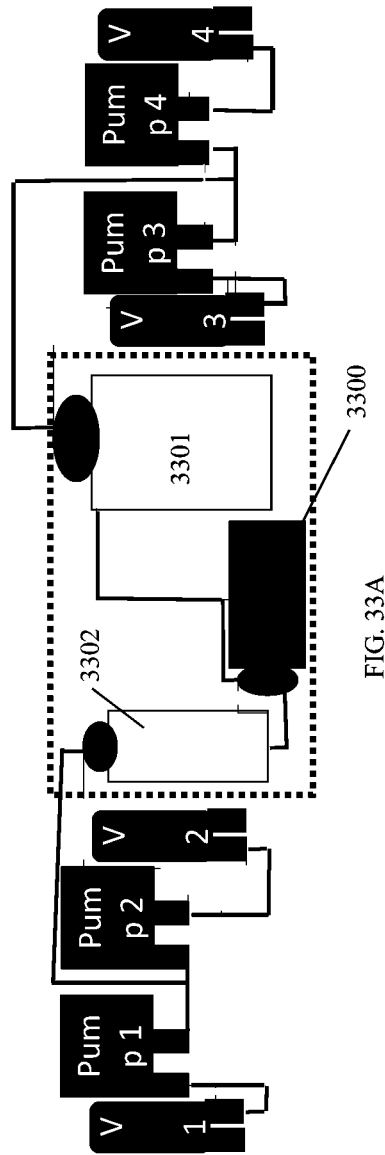
FIG. 33A presents an exemplary diagram of multiple pumps and valves connected to a disposable closed system.

To manufacture the media bottle, injection molding and ultrasonic welding processes may be utilized. In some embodiments, luer lock pieces may be welded in the injection molded vial. In other embodiments, media tubing may be introduced into the media vial through a hole or barbed connectors at a wall of the vial or at a cap of the vial. In some embodiments, a T-flask 3300 may be fluidically connected to a media vial 3301 and a waste bottle 3302 and may be pneumatically connected to two sets of pumping system as shown in FIG. 33A. Pump P1 and P3 provide positive pressure and pumps P2 and P4 provide negative pressure. Corresponding valves V1-V4 connected to the pumps P1-P4 provide an airtight operation. The portion of the fluidics enclosed in a dotted rectangle 3305 may be disposable, which may be used for cell culture.

Figure 33B:
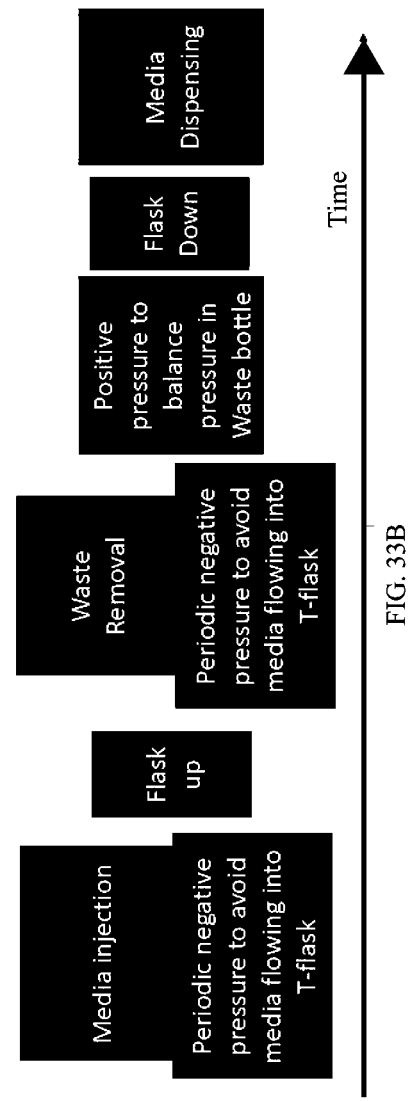
FIG. 33B presents an exemplary diagram of an algorithm for automated fluidics in a closed cell culture system.
Figure 34A:
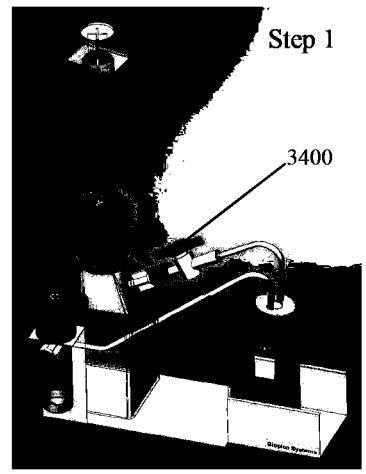
FIG. 34A presents an exemplary diagram of Manifold and step 1 operation of a manual closed cell culture system through a T-flask cap.
Figure 34B:
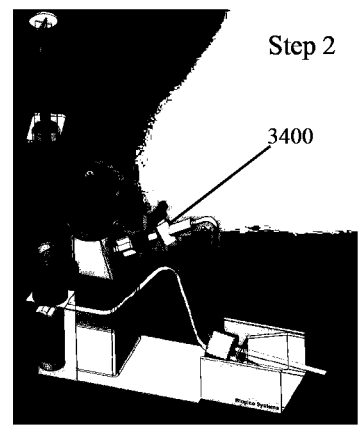
FIG. 34B presents an exemplary diagram of Manifold and step 2 operation of the manual closed cell culture system through the T-flask cap.

In most embodiments, to carry out automated media exchange, multiple steps may be programmed using a microcontroller or processor as displayed in FIG. 33B. The algorithm provides negative pressure during positive pressure operation to balance the pressure inside the vial or bottle. In some embodiments, fluidic valves may not be used in the system; therefore, the pressure balance may be important for normal operation of the fluidics. During media delivery into the media vial, periodic negative pressure pulses may be applied to avoid unwanted media delivery into the T-flask. Positive pressure may be applied at the waste bottle for unwanted waste media to be transported into the T-flask during media dispensing. In some embodiments, a manual mode of operation may be done for media exchange in two steps: Step 1 as depicted in FIG. 34A for waste removal, and Step 2 as depicted in Fig, 34B for media delivery. To avoid waste backflow during operation a luer valve may be closed during media delivery. The manual operations may also be carried out using a custom T-flask with luer connectors having valves 3400. The waste removal may be carried out with a waste side valve open and the media side valve closed. During media delivery, the media valve may be opened and the waste side valve may be closed.

Figure 34C:
FIG. 34C presents an exemplary diagram of a portable microscope integrated to a closed cell culture system.
Figure 34D:
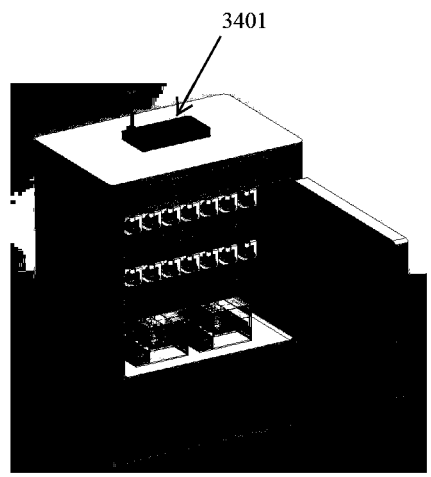
FIG. 34D presents an exemplary diagram of an array of T-flasks stored in an incubator and connected to the internet for remote operations and imaging cells in a closed cell culture system.

Quality control on the cell or organ culture may be visually carried out by microscopic imaging as in FIG. 34C. In another embodiment, a set of cell culture flasks may be arranged with individual media and waste sources as depicted in FIG. 34D. An array of cell culture devices with a microscopic imaging interface may be arranged in an incubator. Images from the imaging interface may be transmitted 3401 (via a transmitter) to users or investigators. This system may be used for contract services of cell manufacturing, cell-based assay, and/or cell biology education.

Accessories for Array Devices

Temperature controlled fluidic operations may be important for the cell or organ culture. Since fluidic operations may be continuously performed, it may be important to capture the gas transport due to pressure pulses within a controlled environment and temperature as depicted in FIG. 35A. The pumps and valves forming the array of fluidic systems may have a lower life time compared to the rest of the non-disposable parts of said system. In some embodiments, a user may be required to replace a pumping block. The pump block may dock into an electronic printed circuit board using electrical sockets 3500 and connect disposable parts in fluidic ports 3501 as in FIG. 35B. In one embodiment, the pumping block may be packaged as a solid block so that customers may replace the sold block after 6-months, 1-year or depending on the usage. Each time the system may be operated, the software will keep track of the pumping elements usage and suggest replacement.

In some embodiments, a pressure sensor may be integrated with the pumping elements to monitor multiple processes. In some embodiments, developing a pressure vacuum source may be important for precise fluidic control. In most embodiments, a PID controller may be developed for working with the 96 well plate chips. In some embodiments, gas transport within a standard well plate may be controlled through channels for better dissipation across the wells as in FIG. 35C. Gaseous transport may be through a gas channel layer 3502 along with a separate fluidic layer 3503 as illustrated in FIG. 35D.

In some embodiments, a cone and plate method may apply shear flow to cell culture in a 96-well plate 3600, which may be made using corner precision linear motors 3601 and an array DC motors 3602. Diameters of the DC motors may be smaller than that of diameters of the wells of 96-well plate 3600. The DC Motors may be arrayed and fixed with precise lengths in a 2-D plate as in FIG. 62A. The plate 3600 may be equipped with a set of corner linear motors 3601 and gyroscopes 3603 to measure a plurality tilting angles. The cone and plate setup may be attached to shafts 3604 of the DC motors 3602 as illustrated in FIG. 62B. In some embodiments, 96 stainless steel shafts 3604 of the DC motors 3602 may be machined with a 2° angled cone.

In some embodiments, shear driven dissociation of cell/tissue aggregates may be carried out in recirculation loop channels with expansion regions 3700 and in multiple steps of decreasing widths 3701, 3702, 3703 as depicted in FIG. 37. In step one, the channels 3700 may be larger and recirculation may be performed for an optimized number of times. After recirculation for the number of times from step 1, the samples may be pulled in step 2 using a connecting channel 3706 and activating the corresponding two wells with vacuum 3704 and pressure 3705 pulses. Once the cells are in the channel 3701 in step 2, recirculation may be performed by appropriately selecting the pumps. This process may be repeated with more steps, i.e, through channels 3703, 3704, and finally, a sample of highly dissociated single cells may be collected at the outlet.

In most embodiments, bonding of multiple layers may be done using line dispensing or using droplet dispensing methods. After dispensing, any bubbles may be removed using a vacuum chamber. In some embodiments, glue may be dispensed using a thimble-type dispensing valve. In other embodiments, ultrasonic bonding energy circles may be drawn around circular walls of components. A luer lock may have a circular bottom and energy circles with pyramid shapes may be made on a bottom plate. Additional energy lines may be made to mechanically strengthen the bonding of the wings of the luer lock with key hole slots. In some embodiments, the automation of the bonding with sticker layers may be important as the sticker layers may be non-toxic for most cell cultures. The sticker layers may be peeled using top and bottom vacuum chucks during assembly of the fluidic chips. The peeling process may be improved with vacuum operating on multiple layers of concentric square paths.

In some embodiments, a volume of fluid pumped across 24 sets of fluidic circuits may be measured by assessing flow rates due to each cycle of tilting using a separate chip 38 with gold electrodes 3800 (with 24+2 pads 3801 shown on the top the separate chip 38) as shown in FIG. 38A. In other embodiments, 192+8 pads 3802 may be used for field potential measurements. In some embodiments, the periodic perfusion system may consistently maintain a fluid level in each well during the fluid circulations so that the organs will be fully immersed into the media, avoiding any air/media effects. In most embodiments, capacitance or impedance may be measured at high speed for measuring the flow rate using interdigitated electrodes 3803 as shown in FIG. 38B.

In most embodiments, software to control the pumps may be developed and communicated wirelessly, as known in the art, as depicted using a smart phone app as seen in FIG. 39A. The software may have a selection of one or more pumps, the total time of the operation, shear rate or flow rate of the pumps and cycle duration if the user may want piece-wise pumping. In most embodiments, hardware to control the fluidics may have provisions for docking the chips, input/output ports 3900 to connect the chips, a replaceable pump cartridge 3901, one or more batteries and electronics as depicted in FIG. 39B.

Sterilizing the chips may be an important step in the biological experimentation with the cells. In some embodiments, gamma, EtO sterilizations may be done in a large scope as a batch process whereas autoclaving involves high temperature. UV radiation and Ethanol may sterilize partially or leaves residue respectively. Flowing ozone in combination with UV provides better sterilization. In most embodiments, the sterilization involves a container to feed air or oxygen through a high voltage tube using a pump and valve arraignment as depicted in FIG. 40A. In most embodiments, the temperature and humidity may be elevated for efficient sterilization. In some embodiments, an ozone generator high voltage tube and a pump and temperature controller may be operated with timers. The flow may be fed into the chip or plate to recirculate ozone.

In some embodiments, electrospinning of PLGA (poly-lactic-co-glycolic acid) material on glass may be performed as shown in FIG. 40B using a syringe pump and high voltage (20-30 kV) applied to a 18 Ga syringe needle and aluminum foil at the bottom of the glass. In most embodiments, a complete closed system for media exchange on multiple wells may be carried out by connecting automated syringes operated on an XYZ table as depicted in FIG. 40C. In most embodiments, media and waste reservoirs may have rubber caps, where a needle of a syringe may pierce the rubber caps to withdraw or insert a liquid. In most embodiments, the metallic needle may be either sterilized separately after collecting them or sterilized instantaneous using a flame electrically operated within, after every transfer of fluid. Standard parallel pipettors may be used for dispensing in multiple wells in a custom format. The tips may be loaded partially to dispense fluid into partial custom wells, for example, as in the case of a connected well, reagents may be delivered to one of the wells. In most embodiments, the reagents may be dispensed in custom wells using a pipette heads in a XYZ table. Tips of the pipette may be changed from a fresh box and the tips may be dispensed to waste containers serially. Proteins or collagens such as Poly-D-lysine and matrigel may be coated into standard well plates using a spiral path across an entire well surface.

In most embodiments, a complete system to control the environment of a fluidic chip may be accomplished by controlling air pressure, oxygen level, $CO_2$ level, temperature and humidity. In FIG. 40D, separate sensors 4002 may be connected to a tank that controls the closed fluidic chip 4003. The parameters may be controlled by input valves.

Example Applications of Invention

High Throughput Fluidic System for Microphysiological Interacting Organs

A chip system with the interactions of multiple organs recapitulate in-vivo tissue-like realistic cellular behavior and provide information on quantitative, time-dependent phenomena when combined with pharmacokinetic modeling approach. These improved interacting-organs assay sets the hope to de-risk human safety and personalize patient treatment in preclinical drug development and facilitates current efforts to reduce, refine, and ultimately replace animal models with more ethical options. However, there may be several challenges to advance these human in vitro organ systems to high throughput preclinical drug toxicity studies so as to evaluate organ function that improves human prediction upon exposure to drugs and their metabolites. This allows static organs with gravity-driven recirculation and perfusion in a 96-well format. Such high throughput toxicology profiling enables early identification of off-target toxicities that would help in the redesign of a drug for patient's safety and cost in preclinical drug development. To validate the metabolic interaction between liver and heart that mimic physiological phenomena for accurate drug safety testing, design of self-contained integrated vasculature and other shear stress-sensitive organ systems may be required. Investigations developing novel physiological in-vitro models with minimally functional units that may recapitulate compound toxicity in humans may be increasing as a consequence of poor prediction during toxicology evaluations with the current static and single organ models. This high throughput unidirectional media recirculation and perfusion system performs studies using liver and heart organs for enabling organs interaction for drug testing.

It may be estimated that only one in nine drug candidates that enter clinical testing reach the market, indicating therapeutic drug development needs more versatile, informative, and rapid preclinical models and accurate prediction of human safety and efficacy. In this regard, interaction among different organs under culture should be simulated like circulation system in a body enabling organ functions as coupled system, e.g., heart: volume pumped; lung: gas exchanged; liver: metabolism; kidney: molecular filtering and transport; and, brain: blood-brain barrier function. This development of interacting-organ systems capable of reproducing the functionality in a quantifiable manner for prediction of human tissue behavior may be an unmet need for understanding the full toxicity profile of drugs and their metabolites simultaneously. In this open platform, Microphysiological Interacting Organs system where static organs developed in transwell plate may be integrated and tested for toxicological profile. Analysis of metabolites and other secretory products may aid in the identification and development of novel biomarkers for efficacy, toxicity or disease processes. To keep the organ system for several days or weeks, fluidic perfusion in a portable format resides in an incubator and provide continuous organ interaction capable of adapting to a microscope environment for optical imaging. Our robust automated fluidic platform will help researchers solve their challenges with multi-organ systems such as implementing a universal medium, proper scaling of models to reproduce maximal functions, vascularization of the models and establishing a source of renewable adult iPSC for the cell types to provide single donor disease phenotype cells. The system enables the reconstitution and visualization of complex, integrated, organ-level responses not normally observed in conventional cell culture models or animal models and has tremendous applications. Validated liver and heart single organs cultured in 24 wells and 96 well transwell plates respectively may be used. The organs may be maintained in liver/heart organ complete medium that allows both the cardiomyocytes and the liver cells to grow under recirculation. The liver organ consists of 3-D culture of human hepatocytes, stellate cells, Kupffer cells, fibroblasts. The heart organ consists of 3-D culture of human cardiomyocytes and fibroblasts. Human liver/cardiac samples may be obtained from consented patients from automobile accident that were transplant reject samples. The organs may be cultured in a humidified incubator with 5% $CO_2$ at 37° C. The effect of the drug dosage on the cells using Doxorubicin (1 mM), Valproic Acid (400 mM), Cyclophosphamide (250-500 μM) and Terfenadine (1 μM to 10 μM) may be studied. The fluidic systems will be gamma sterilized before loading the organs. To evaluate the effects of interaction between liver and heart organs, drug treatments may be performed to the reservoir adjacent to the liver well. Urea and albumin productions may be quantified from the supernatant with commercial kits from BioAssay Systems and Bethyl Laboratory Inc., respectively. Conduction velocity, QT-interval and spontaneous beat frequency may be measured from field potential measurements to quantitate toxicity profiles. The exchange of medium between organs may be analyzed by measuring the amount of albumin secreted by hepatocytes. Liver function may be maintained for a 30-day period and rate of albumin production profile across the period may be compared with in-vivo data from the literature to validate our organ system.

Blood-Retinal Barrier Models

The blood-retinal barrier (BRB) protects the retina by maintaining an adequate microenvironment for neuronal function. Alterations of the BRB or BRB breakdown in disease contribute to a loss of neuronal signaling and vision. Physiologically relevant in vitro models that recapitulate the features of retinal barrier biology will improve disease modeling, target validation, and toxicity assessment in new therapeutics. 3-D organ models with physiologic flow, extra cellular matrix (ECM) proteins, multicellularity, and control over microenvironmental properties may help approach actual tissue organization and function and offer additional tools to model and study diseases, drug toxicity predictions and pharmacokinetic/pharmacodynamics assessment. In a multi-layer model, retinal endothelial cells for the iBRB (inner) or retinal pigmented epithelial cells for the oBRB (outer) may be seeded in one compartment of the chip to generate monoculture devices or integrated as co-tri-culture devices where the other cell types may be seeded on another compartment of the chip well plate. The inclusion of multiple cell types enhanced physiological relevance by enabling crosstalk between neighboring cell populations. Further, investigating cell-cell communication enabled mechanistic studies of developmental, functional, and pathological processes of the retina, as support cells may be known to influence BRB permeability and endothelial cell functions. For example, integrating pericytes, astrocytes, and/or astrocyte-conditioned medium with endothelial cells in an iBRB chip model enhanced tight junction protein content and trans-endothealial electrical resistance values compared with monoculture and provided a more relevant frame to investigate permeability. A coculture of primary retinal pigmented epithelial cells and primary endothelial cells revealed specific cell-cell mechanisms that induce choroidal neovascularization as observed in age-related macular degeneration. To recapitulate the tri-layered structure of the oBRB, retinal pigmented epithelial cells and endothelial cells may be seeded side-by side in ECM, which induced phenotypic changes in the endothelium. The shear stress regulates barrier properties, induces changes in gene expression, and glycocalyx maturity.

Multiscale Modeling of Vascular Pathophysiology

Vascular diseases, such as atherosclerosis, aneurysms, peripheral artery disease, and thrombosis, are the leading cause of morbidity and mortality worldwide, accounting for over 17 million deaths per year. There may be a crucial need to increase our understanding of vascular disease pathophysiology and assess emerging interventions to accelerate therapeutic development. Organ-on-a-chip modeling approaches that evaluate molecular, cellular, tissue, and organ level variables may be required for a systematic and robust assessment of mechanisms and therapeutic interventions in the blood vessel. The outer layer of blood vessels may be composed of fibroblasts and loose connective tissue, serving as an anchor for the vessel. Together, this lamellar structure maintains several biological functions of the blood vessel, such as regulation, extravasation, or intravasation blood vessels with fibroblasts, epithelial cells, and embedded ECM. A broad range of velocities that exists in the vascular system—ranging from 0.3 m/s in the aorta to 0.1 mm/s in vascular branches at the capillary level with diverse shear-dependent signaling within the endothelium. Perfusion in organs provides a mechanism to continuously transport and distribute soluble factors, permitting long term culture of cells. Blood vessel-on-a-chip system may be able to predict the toxicity of a drug compound that failed clinical trials but does not produce the same vascular side-effects in primate studies. The blood vessel-on-a-chip model needs connective tissue, containing fibroblasts between the epithelium and endothelium, which may regulate vascular homeostasis and pathogenesis.

White Adipose Tissues for Mechanistic Research

The global obesity pandemic poses one of today's biggest challenges to public health. White adipose tissue (WAT) may be the principal organ in obesity. In healthy human adults, WAT comprises approximately 20-25% of the total body mass, thus constituting the second largest organ, after the skin. In obese individuals, WAT's contribution to the total body mass may become as high as 50%. In line with its important roles in metabolism, inflammation and cancer, WAT has emerged as a drug target with major therapeutic potential for a variety of diseases. Microscale platforms that provide microphysiological environments for the long-term culture of white adipocytes in structures recapitulate in vivo physiology, and functionality based on a minimal amount of cells.

Convective transport of nutrients, metabolites, and other dissolved molecules mimicking the in vivo circulation of blood may be carried out to administer compounds with high temporal resolution. The membrane between chambers ensures that convective transport may be restricted to the media channels, thereby shielding the tissue chambers from non-physiological shear forces. Through the micropores, dissolved molecules may diffuse quickly in and out of the tissue chambers. Although this artificial barrier admittedly does not recapitulate active transport processes occurring in vivo, it does provide a potential scaffold for the inclusion of endothelial cells. 3D tissues composed of large adipocytes may be maintained in physiological microenvironments and conditions.

Human Islet Organoids from iPSCs

Human pluripotent stem cell (hPSC)-derived islet cells provide promising resources for diabetes studies, cell replacement treatment and drug screening. Controllable aggregation of embryoid bodies (EBs), in situ pancreatic differentiation and generation of heterogeneous islet organoids may be cultured. The generated islet organoids contain heterogeneous islet-specific a and β-like cells that exhibit favorable growth and cell viability. They show enhanced expression of pancreatic β-cell specific genes and proteins and increased β-cell hormone specific gene and protein expressions under perfused culture conditions. Pancreatic islet organogenesis in vivo may be tightly regulated by complex and dynamic cellular niche signals involving blood flow, transcription factors, and multicellular interactions, thereby yielding functional islets responsible for glucose homeostasis. Pancreas organogenesis during embryonic development in vivo may be a complex and dynamic process, relying on the control of mechanical and biochemical cues. The condition of the media flow provided continuous media and nutrients to support the formation and long-term culture of the islets. Different chemical factors may be sequentially added to the culture medium during the developmental process to generate islet organoids from hiPSCs. These factors may induce the efficient differentiation of pancreatic progenitor cells and insulin-producing cells. To assess the degree of maturity and functionality of islets under perfused culture conditions, protein markers related to insulin secretion and cell maturation in islets may be examined.

Drug-Induced Proximal Tubule Kidney Injury

The global prevalence of chronic kidney disease is 13.4%, with a burden to US healthcare system exceeding $48 billion per year. At present, the disease may be managed mainly by controlling underlying causes such as diabetes and hypertension, optimizing cardiovascular risk, and providing supportive care without adequate means for understanding the physiologic and pathophysiologic mechanisms involved in renal damage and repair. Development of pharmacologic therapies has also been hampered by non-predictive in vitro models which could not recapitulate multicellular complex architecture in vivo kidney function, and animal models which have been unreliable in predicting response to therapy in humans. This may be evident that in the preclinical stages of development, nephrotoxicity accounts for 2% of drug failures while in Phase III clinical studies 20% of all failures. This nephrotoxicity negatively affects the reproducibility, cost-effectiveness, and overall applicability, posing a challenge for in vivo studies. Also, therapeutic drugs may exert their toxic effects on various targets in the kidney, particularly in the proximal tubules where active clearance, reabsorption, intracellular concentration, and local interstitial accumulation of drugs occur. The nephron models being developed to combat such challenges still lack high throughput vascularized organs established by unidirectional recirculation for pharmacological studies. Therefore, high throughput 3D vascularized proximal tubule disease models with unidirectional recirculation will fill the translational gap between preclinical toxicology and its predictive value to the clinic. These 96-well plate engineered in vitro living nephron models would realize precise, patient-oriented clinical solutions to revolutionize mechanistic drug studies, disease models and regenerative medicine. The robust, quick and efficient engineered complex functional system will better recapitulate in vivo microenvironments to quantitatively model human proximal tubules and to test therapeutic drug efficacy.

Hepatic Function, Toxicity and Responses

The liver plays a crucial role in drug metabolism, detoxification and energy homeostasis in the human body. As a central organ for drug metabolism, hepatotoxicity accounts for about 70% of failures during drug development processes adverse drug reactions, undetected hepatotoxicity, and idiosyncratic responses are still the leading cause of drug withdrawals from the global marketplace. For organ models that incorporate dynamic flow and biological complexity with sufficient throughput will maintain relevance in-vivo characteristics for drug study. Utilizing a collagen sandwich culture, enzymatic and secretory functions of primary human hepatocytes in such systems, the recapitulation of mass transport of small proteins within the liver sinusoid may be carried out. Generation of high-throughput biological replicates with mono- and multi-cell cultures, helps to culture primary human hepatocytes in re-circulating media flow, allowing for the introduction of exogenous soluble factors to investigate cellular responses and feedback. Retaining differentiated primary human hepatocytes phenotypes over a period of two weeks to accommodate chronic exposure studies helps in disease modeling. Common liver diseases such as nonalcoholic steatohepatitis and cholestasis may be characteristic of perturbations in fatty acid metabolism and ectopic accumulation of excess lipid in the liver. Addition of fatty acids into in vitro hepatocyte cultures may be commonly used to mimic hepatic steatosis, however their effects in chronic dosing, and feedback may be largely unknown. These hepatic functions may be studies using physiological relevant liver models.

With respect to the above description, it is to be realized that any of the above embodiments may readily be combined with any one or more embodiments also listed above. In particular, with respect to the above description, it is to be realized that the optimum dimensional relation ships for the parts of the present invention may include variations in size, materials, shape, form, function and manner of operation. The assembly and use of the present invention are deemed readily apparent and obvious to one skilled in the art.

The invention claimed is:

1. A method for a culture system to model fluid flow for maturing organs in a human physiological system, the method comprising:
using a fluidic plate with a plurality of wells; wherein the plurality of wells are connected by at least one of a plurality of fluidic channels;
inserting a fluid into at least one of the plurality of wells; and
tilting the fluidic plate to create flow in the fluid within the at least one of the plurality of wells; wherein tilting the fluidic plate so that each corner of the fluidic plate raises and lowers individually; wherein the tilting creates unidirectional flow through the plurality of wells connected by the plurality of fluidic channels;
wherein a unidirectional fluidic recirculation loop is formed in the fluidic channels connected between at least three wells of the plurality of wells caused by the tilting;
wherein the fluid in the culture system comprises at least one of a plurality of cells, organs, organoids, and cell media.

2. The method of claim 1, wherein at least one motor is used for the tilting of the fluidic plate; wherein the at least one motor is an actuator; wherein each one of the at least one motor raises and lowers a separate corner of the fluidic plate.

3. The method of claim 1, wherein the plurality of wells are connected by the plurality of the fluidic channels to form at least two recirculation loops.

4. The method of claim 3, wherein the fluid is trapped in the at least two recirculation loops to stimulate cells, organs, or organoids with fluidic shear created by the flow caused by the tilting.

5. The method of claim 4; wherein at least one of the plurality of fluidic channels is serpentine shaped.

6. The method of claim 3, wherein fluidic transfer occurs between the at least two recirculation loops through at least one side channel.

7. The method of claim 6, wherein the at least two recirculation loops are spaced apart a spatial distance, where the spatial distance is at least one of vertical distance and a horizontal distance; wherein the at least one side channel transverses the spatial distance to connect the at least two of the plurality of recirculation loops.

8. The method of claim 6, wherein the plurality of wells or the channels connected by the at least two recirculation loops are separated by at least one ramp channel or at least one filter.

9. The method of claim 6, wherein the fluid is loaded into the at least one recirculation loop, the at least one of the plurality of wells, or the at least one of the plurality of side channels; wherein the fluid disperses into at least one non-loaded area; wherein the non-loaded area includes the at least one recirculation loop, the at least one of the plurality of wells, and the at least one of the plurality of side channels.

10. The method of claim 1, the method further comprising:
applying a microfluidic lid to the fluidic plate;
connecting a plurality of containers to the microfluidic lid, wherein the plurality of containers hold a second fluid, wherein the second fluid is at least one of a reagent, a media, and an additional amount of the fluid;
refreshing the at least one of the plurality of wells by at least one of a plurality of pumps that transfer the second fluid from at least one of the plurality of containers to the microfluidic lid and into at least one of the plurality of wells.

11. The method of claim 1, the method further comprising:
placing the fluidic plate on a microscope for recirculation and imaging of the fluid; wherein the recirculation and imaging is at least one of a simultaneous process and a successive process.

12. The method of claim 1, the method further comprising:
inserting a plurality of cell inserts or transwell plates into the at least one of the plurality of wells; wherein the plurality of cell inserts or transwell plates have subwells connected by subwell channels; wherein at least one of the subwells and the subwell channels contains the fluid;
tilting the fluidic plate to create flow in the fluid within the subwells and the subwell channels for recirculation.

13. The method of claim 12, the method further comprising:
inserting at least one of a plurality of cell culture reagents into at least one of the plurality of wells, the subwells, and the subwell channels for storage; wherein the at least one of the plurality of wells, the subwells, and the subwell channels store at least one dose of the at least one of the plurality of cell culture reagents.

14. The method of claim 1, wherein the fluid is perfused with at least one of a plurality of programmed concentrations; wherein the plurality of programmed concentrations includes at least one of drugs, toxins, and reagents.

15. The method of claim 1, the method further comprising:
placing the fluidic plate on a base layer containing at least one field potential measurement sensor;
monitoring the fluid using the at least one field potential measurement sensor; wherein the at least one field potential measurement sensor measures at least one of a flow measurements, impedance measurements, and transepithelial-endothelial electrical resistance measurements;
transmitting data to a remote location via a wireless transmitter; wherein the remote location includes at least one of a computer, a tablet, a smartphone.

16. The method of claim 1, further comprises:
controlling an environment of the plurality of wells; wherein the environment comprises at least one of a plurality of gases including air, nitrogen, oxygen, and carbon-di-oxide; wherein the environment is controlled by at least one of a plurality of pumps connected to at least one source of the at least one of the plurality of gases.

* * * * *